United States Patent [19]

Falk et al.

[11] Patent Number: 5,792,753
[45] Date of Patent: Aug. 11, 1998

[54] COMPOSITIONS COMPRISING HYALURONIC ACID AND PROSTAGLANDIN-SYNTHESIS-INHIBITING DRUGS

[75] Inventors: Rudolf Edgar Falk; Samuel Simon Asculai, both of Toronto, Canada

[73] Assignee: Hyal Pharmaceutical Corporation, Mississauga, Canada

[21] Appl. No.: 18,508

[22] Filed: Feb. 17, 1993

Related U.S. Application Data

[63] Continuation-in-part of Ser. No. 675,908, Jul. 3, 1991, and Ser. No. 838,675, Feb. 21, 1992, Pat. No. 5,639,738, which is a continuation-in-part of Ser. No. 675,908, Jul. 3, 1991.

[51] Int. Cl.$^6$ .................... A61K 31/715; A61K 31/725
[52] U.S. Cl. .................... 15/54; 514/23; 514/62; 536/53; 536/55.2; 536/88; 536/123.1
[58] Field of Search .................... 514/23, 54, 62; 536/55.2, 88, 123.1, 53

[56] References Cited

U.S. PATENT DOCUMENTS

| | | |
|---|---|---|
| 2,583,096 | 1/1952 | Hadidian et al. . |
| 3,042,667 | 7/1962 | Flodin et al. . |
| 3,357,784 | 12/1967 | Kasper et al. . |
| 3,396,081 | 8/1968 | Billek et al. . |
| 3,436,454 | 4/1969 | Nouvel . |
| 3,792,164 | 2/1974 | Bechtold et al. . |
| 3,845,201 | 10/1974 | Haddad et al. . |
| 3,870,791 | 3/1975 | Haddad et al. . |
| 3,887,703 | 6/1975 | Manoussos et al. . |
| 4,003,991 | 1/1977 | Krohn et al. . |
| 4,045,558 | 8/1977 | Smith et al. . |
| 4,061,722 | 12/1977 | Bodor et al. . |
| 4,141,973 | 2/1979 | Balazs .................... 514/54 |
| 4,240,163 | 12/1980 | Galin . |
| 4,255,415 | 3/1981 | Chrai et al. . |
| 4,271,143 | 6/1981 | Schoenwald et al. . |
| 4,272,522 | 6/1981 | Balazs . |
| 4,280,954 | 7/1981 | Yannas et al. . |
| 4,303,676 | 12/1981 | Balazs .................... 514/773 |
| 4,328,803 | 5/1982 | Pape . |
| 4,470,975 | 9/1984 | Berger, deceased et al. . |
| 4,478,822 | 10/1984 | Haslam et al. . |
| 4,487,865 | 12/1984 | Balazs et al. . |
| 4,500,676 | 2/1985 | Balazs . |
| 4,517,295 | 5/1985 | Bracke . |
| 4,582,865 | 4/1986 | Balazs et al. .................... 524/29 |
| 4,629,623 | 12/1986 | Balazs et al. . |
| 4,636,524 | 1/1987 | Balazas et al. .................... 514/781 |
| 4,684,627 | 8/1987 | LeVeen et al. .................... 514/25 |
| 4,686,288 | 8/1987 | Lormeau et al. . |
| 4,711,780 | 12/1987 | Fahim .................... 424/641 |
| 4,713,448 | 12/1987 | Balazs et al. . |
| 4,716,224 | 12/1987 | Sakurai et al. . |
| 4,725,585 | 2/1988 | Wenge et al. .................... 514/54 |
| 4,736,024 | 4/1988 | Della Valle et al. .................... 536/55.3 |
| 4,746,504 | 5/1988 | Nimrod et al. . |
| 4,755,544 | 7/1988 | Makino et al. .................... 524/42 |
| 4,782,046 | 11/1988 | Brown et al. . |
| 4,784,990 | 11/1988 | Nimrod et al. . |
| 4,784,991 | 11/1988 | Nimrod et al. . |
| 4,795,741 | 1/1989 | Leshchiner et al. .................... 514/21 |
| 4,801,619 | 1/1989 | Lindblad .................... 514/42 |
| 4,804,537 | 2/1989 | Bergman et al. . |
| 4,808,576 | 2/1989 | Schultz et al. .................... 514/54 |
| 4,814,171 | 3/1989 | Tack et al. . |
| 4,814,176 | 3/1989 | Makino et al. .................... 424/457 |
| 4,840,941 | 6/1989 | Ueno et al. .................... 514/59 |
| 4,851,521 | 7/1989 | della Valle et al. .................... 536/55.1 |
| 4,853,224 | 8/1989 | Wong . |

(List continued on next page.)

FOREIGN PATENT DOCUMENTS

| | | |
|---|---|---|
| 30806/84 | 7/1984 | Australia . |
| B-72117/87 | 12/1987 | Australia . |
| 15456/88 | 9/1988 | Australia . |
| 29145/89 | 6/1989 | Australia . |
| 14534/88 | 11/1990 | Australia . |
| 17459/88 | 8/1991 | Australia . |
| 1087610 | 10/1980 | Canada . |
| 1205031 | 5/1986 | Canada . |
| 1240929 | 8/1988 | Canada . |
| 2006060 | 12/1989 | Canada . |
| 2004740 | 6/1990 | Canada . |
| 2031880 | 12/1990 | Canada . |
| 1317287 | 5/1993 | Canada . |

(List continued on next page.)

OTHER PUBLICATIONS

Sandra Blakeslee, "Solid cores of tumors keeping out best drugs", Jul. 8, 1989 edition of the Globe and Mail, Toronto, Ontario, p. D4.

Pam Harrison, "Toxic drug tamed but still potent" *Ontario Medicine*, vol. 8, No. 16 dated Aug. 21, 1989, p. 1.

*The Merck Index* Eleventh Edition, Centennial Edition, Hyaluronic Acid formulation, pp. 751 and 752, 1989.

Alan R. Liss, Inc., Modulation of Immunity in Cancer Patients by Prostaglandin Antagonists, *Immunity to Cancer II*, Braun et al. pp. 439–448, 1989.

(List continued on next page.)

*Primary Examiner*—Kathleen K. Fonda
*Attorney, Agent, or Firm*—Ivor M. Hughes; Neil H. Hughes; Marcelo K. Sarkis

[57] ABSTRACT

A topically administrable pharmaceutical composition is disclosed which comprises a therapeutically effective amount of a drug which inhibits prostaglandin synthesis, and an amount of a form of hyaluronic acid sufficient to transport the composition through the skin into the epidermis or dermis where the composition remains until discharged via the lymphatic system, wherein (a) the drug is 1–5% by weight of the composition, and
(b) the form of hyaluronic acid is 1–3% by weight of the composition, has a molecular weight greater than about 150,000 daltons and less than 750,000 daltons, and is selected from the group consisting of hyaluronic acid and salts thereof.

16 Claims, 12 Drawing Sheets

(7 or 12 Drawing(s) in Color)

5,792,753
Page 2

U.S. PATENT DOCUMENTS

| | | |
|---|---|---|
| 4,853,226 | 8/1989 | Machida et al. |
| 4,855,134 | 8/1989 | Yamahira et al. |
| 4,863,907 | 9/1989 | Sakurai et al. |
| 4,877,619 | 10/1989 | Richer. |
| 4,879,282 | 11/1989 | Saliba, Jr. |
| 4,912,093 | 3/1990 | Michaeli. |
| 4,913,898 | 4/1990 | Altobelli et al. |
| 4,937,254 | 6/1990 | Sheffield et al. ............ 424/497 |
| 4,937,270 | 6/1990 | Hamilton et al. |
| 4,944,941 | 7/1990 | Ammann. |
| 4,946,870 | 8/1990 | Partain, III et al. |
| 4,957,744 | 9/1990 | della Valle et al. ............ 424/401 |
| 4,963,666 | 10/1990 | Malson. |
| 4,965,353 | 10/1990 | della Valle et al. ............ 424/401 |
| 4,970,298 | 11/1990 | Silver et al. ............ 530/356 |
| 5,095,037 | 3/1992 | Iwamitsu et al. ............ 514/561 |
| 5,166,331 | 11/1992 | della Valle et al. ............ 536/55.1 |

FOREIGN PATENT DOCUMENTS

| | | |
|---|---|---|
| 769 287 | 3/1957 | European Pat. Off. |
| 0 138 572 | 4/1985 | European Pat. Off. |
| 0138216 | 4/1985 | European Pat. Off. |
| 0136782 | 10/1985 | European Pat. Off. |
| 0 179 442 | 4/1986 | European Pat. Off. |
| 0 197 718 | 10/1986 | European Pat. Off. |
| 0 208 623 | 1/1987 | European Pat. Off. |
| 0 216 453 | 4/1987 | European Pat. Off. |
| 0 244 178 | 4/1987 | European Pat. Off. |
| 0 224 987 | 6/1987 | European Pat. Off. |
| 0 240 098 | 10/1987 | European Pat. Off. |
| 0 265 116 | 4/1988 | European Pat. Off. |
| 0 270 317 | 6/1988 | European Pat. Off. |
| 0 285 357 | 10/1988 | European Pat. Off. |
| 0 287 210 | 10/1988 | European Pat. Off. |
| 0 295 092 | 12/1988 | European Pat. Off. |
| 0 296 740 | 12/1988 | European Pat. Off. |
| 0 312 208 | 4/1989 | European Pat. Off. |
| 0 341 745 | 5/1989 | European Pat. Off. |
| 0378852 | 12/1989 | European Pat. Off. |
| 0437622-A1 | 7/1991 | European Pat. Off. |
| 2364373 | 10/1975 | Germany. |
| 57-183707 | 12/1982 | Japan. |
| 61-000017 | 1/1986 | Japan. |
| 62-201825 | of 1987 | Japan. |
| 63/045223 | 2/1988 | Japan. |
| A-63-116678 | 11/1989 | Japan. |
| 27287 | 1/1990 | Japan. |
| 818336 | 8/1959 | United Kingdom. |
| 1283892 | 8/1972 | United Kingdom. |
| 2099826 | 12/1982 | United Kingdom. |
| WO 84/04453 | 11/1984 | WIPO. |
| WO 86/00912 | 2/1986 | WIPO. |
| WO 86/03125 | 6/1986 | WIPO. |
| WO 88/06840 | 9/1988 | WIPO. |
| WO 88/07060 | 9/1988 | WIPO. |
| WO 88/07853 | 10/1988 | WIPO. |
| WO 89/03205 | 4/1989 | WIPO. |
| WO 89/05645 | 6/1989 | WIPO. |
| WO 89/07932 | 9/1989 | WIPO. |
| WO 89/10941 | 11/1989 | WIPO. |
| WO 90/10020 | 9/1990 | WIPO. |
| WO 90/10031 | 9/1990 | WIPO. |
| WO 91/04058 | 4/1991 | WIPO. |

OTHER PUBLICATIONS

Goodwin, J.S. Prostaglandin E and Cancer Growth Potential for Immunotherapy with Prostaglandin Synthesis Inhibitors, *Augmentive Agents in Cancer Therapy*, Raven Press, New York, (1981).

Dr. Samuel Asculai. "*Inactivation of Herpes Simplex Viruses by Nonionic Surfactants*", Antimicrobial Agents and Chemotherapy, Apr. 1978, pp. 686–690.

Chemical Abstracts, vol. 76, No. 10; W. E. Sneader; "Possible Mechanism for action of DMSO on Percutaneous absorption", J. Pharm. Pharmcol. 1971, 23 (Supp).

Alaverdyan MI, Ter–Avetisyan AT. Effect of hyaluronidase, hyaluronic acid, and some other substances on postradiational experimental bacteriemai. *Bulletin of Experimental Biology and Medicine* 1967; 64(9):967–969.

Balazs EA, Gibbs DA. The rheological properties and biological function of hyaluronic acid. In: *Chemistry and Molecular Biology of the Intercellular Matrix. vol. III.* New York: Academic Press, 1970. pp. 1241–1253.

Balazs EA, Band P. Hyaluronic acid: Its structure and use. *Cosmetics & Toiletries*. Polymers in Cosmetics 1984; 99; 65–72.

Camber O, Lundgren P. Diffusion of some low molecular weight compounds in sodium hyaluronate. *Acta Pharmaceutica Suecica* 1985; 22(6):315–320.

Camber O, Edman P, Gurny R. Influence of sodium hyaluronate on the meiotic effect of pilocarpine effect in rabbits. *Current Eye Research* 1987: 6(6):779–784.

Chang S–C. Pro–drug and vehicle approaches to improve the therapeutic index of topically applied timolol in the pigmented rabbit. *Dissertation Abstracts International* 1988; 49(2) 367–B.

Cravioto, R.O. et al. Effects of Precipitates Formed by Insulin with Hyaluronic Acid and Mucoid From Vitreous Humor in Depressing Blood–Sugar Levels *Science* (1950): vol. 111:520–521.

Gieldanowski, Jerzy: Skowronska, Jadwiga Studies on immunosuppressive and anti–inflammatory effect of adriamycin. *Arch. Immunol. Ther. Exp.* (1980); 28 (3):439–446.

Hassan HG, Akerman B, Ranck H, Lindberg B, Lindquist B. Effects of adjuvants to local anaesthetics on their duration. *Acta Anaesthesiol. Scand.* 1985; 29:384–388.

Hurd ER Immunosuppresive and anti–inflammatory properties of cyclophosphamide, azathioprine and methotrexate. *Arthritis and Rheumatism* (1973 Jan.–Feb.); 16 (1):84–88.

Idson B. Polymers in skin cosmetics. *Cosmetics & Toiletries* 1988; 103:63–68.

Johansson A, Hassan H, Renck H. Effects of adjuvants to local anaesthetics on their duration. *Acta Anaesthesiol. Scand.* 1985; 29:736–738.

Kalbhen D.A. The inhibitory effects of steroidal and non–steroidal antirheumatic drugs on articular cartilage in osteoarthrosis and its counteraction by a biological GAG-peptide complex (Rumalon®). *Z Rheumatol* (1982); 41:202–211.

Katsu M., Abe T., Shimada S. Significance and clinical use of non–steroid anti–inflammatory drugs as substitutes for steroids in steroid dependence. *Nippon Rinsho* (1968 Jan); 26(1):89–95.

Kreis H, Chkoff N, Droz D, et al. Nonsteroid anti–inflammatory agents as a substitute treatment for steroids in ATGAM–treated cadaver kidney recipients. *Transplantation* (1984 Feb.); 37(2): 139–145.

McIlwraith W. Current concepts in equine degenerative joint disease. *Journal of the American Veterinary Medical Association* 1982; Feb. 1:239–250.

Mizushima, Y. Possibility of non–steroid anti–inflammatory drugs as a substitute for steroids–analysis of the present situation and demands for the future. *Nippon Rinsho* (Jan. 1986); 26(1): 61–65.

Nizolek DJH, White KK. Corticosteroid and hyaluronic acid treatments in equine degenerative joint disease: A review. *The Cornell Veterinarian* 1981; 71(4):355–375.

Pigman W, et al. Acide hyaluronique et facteurs de perméabilité tissulaire. *Bull. Soc. Chim. Biol.* 1963; 45(2–3):185–202.

Pruett RC, Schepens CL, Constable IJ, Swann DA. Hyaluronic acid vitreous substitute. In: *Vetreous Surgery and Advances in Fundus Diagnosis and Treatment*. Freeman H.M., et al., Editors. Appleton–Century–Crofts, 1977: Chapter 55, pp. 433–444.

Reim M, Teping C. Surgical procedures in the treatment of most severe eye burns. *Acta Ophthalmologica* 1989–Supplementum 192; 67:47–54.

Rydell NW, Balazs EA. Effect of intra–articular injection of hyaluronic acid on the clinical symptons of osteoarthritis and on granulation tissue formation. *Clinical Orthopaedics and Related Research* 1971; 80(Oct.):25–29.

Saba P, Galeone F, Salvadorini F, Guarguaglini M, Ombrato M. Investigation of the antihyperlipemic activity of an association of clofibrate and extractive mucopolysaccharide complex. *Current Therapeutic Research* 1978; 23(4): 455–463.

Stegman R, Miller D. Use of sodium hyaluronate in severe penetrating ocular trauma. *Acta Ophthalmol.* 1986; 18: 9–13.

Trabucchi E, Foschi D, Marazzi M, Radaelli E, Lucianetti A, Rizzitelli E, Baratti C, et al. Prevention of wound dehiscence in severely obese patients with jejuno–ileal by–pass: The role of hyaluronic acid. *Pharmatherapeutica* 1988; 5(4): 233–239.

Sertoli P, Merello A, Parodi M. L'acido jaluronico, per uso topico, nella cura delle ulcere trofocircolatorie degli arti inferiori. (Comunicazioni). *Giornale Italiano di Dermatologia* 1970; 45(8): 468–471.

Walther, M. The Prevention of Strine Cutis Distansae During Pregnancy. *Mineva Gynecolgia* (1981) vol. 33: 497–499.

Weirich, E.G., Longauer, J.K., Kirkwood, A.H. Dermatopharmacology of salicylic acid. III. Topical contra–inflammatory effect of salicylic acid and other drugs in animal experiments. *Dermatologica* (1976); 152(2): 87–89.

Kelley et al (1990) J. Dermatol. Surg. Oncol.

West et al (1989) Exp. Cell Res. 183:179–196.

Reynolds (ed.) "Martindale The Extra Phamacopoeia," The Pharmaceutical Press, London (1982), pp. 234–235.

Alho et al (1989) J. Cell Biol 108:1557–1565.

Abatangelo G, Martelli M, Vecchia P. Healing of hyaluronic acid–enriched wounds: Histological observations. *J. Surgical Research* 1983; 35: 410–416.

Abatangelo G, Corvito R, et al. Cell detachment mediated by hyaluronic acid. *Exp. Cell Res.* 1982; 137: 73–78.

Adams JB. Steroid hormones and breast cancer. *Dissertation Abstracts International* 1981; 42(4): 1425B.

Ahlgren T, Jarstrand C. Hyaluronic acid enhances phagocytosis of human monocytes in vitro. *J Clinical Immunology* 1984; 4(3): 246–249.

Alexander P. Ageing skin: Remedial measures. *Manuf. Chemist* 1985; Oct.: 35, 37, 39.

Altman RD, Kapila P, Dean DD, Howell DS. Future therapeutic trends in osteoarthritis. *Scand. J. Rheumatology* 1989; Suppl. 77: 37–42.

Ambroggio G, Barberis ML Trattamento di lesioni cutanee ad andamento cronico con acido ialuronico. *Minerva Chirurgica* 1969; 23(15): 815–818.

Amsterdam A, Shemesh M, Riesel R, Amir Y, Salomon Y. Intra–ovarian inhibitor of luteinizing hormone sensitive adenylate cyclase. *Israel Journal of Medical Sciences* 1977; 13(9):968–969.

Anastassiades T, Robertson W. Modulation of mitogen–dependent lymphocyte stimulation by hyaluroniccid. *J Rheum.* 1984; 11(6): 729–734.

Appel A, Horwitz AL, Dorfman A. Cell–free synthesis of hyaluronic acid in marfan syndrome. *J Biological Chemistry* 1979; 254(23): 12199–12203.

Arzeno G, Miller D. Effect of sodium hyaluronate on corneal wound healing. *Arch Ophthalmol* 1982; 100: 152.

Balazs EA, Band P. Hyaluronic acid: Its structure and use. *Cosmetics & Toiletries* .Polymers in Cosmetics 1984; 99: 65–72.

Balazs EA, Freeman MI, et al. Hyaluronic acid and replacement of vitreous and aqueous humor. *Modern Problems in Ophthalmology: Secondary Detachment of the Retina* 1971; 10: 3–21.

Barondes SH. Bifunctional properties of lectins: Lectins redefined. *TIBS* 1988; 13 (Dec.): 480–482.

Barron BA, et al. Comparison of the effects of viscoat and healon on postoperativ intraocular pressure. *Am. J. Ophthallmology* 1985; 100: 377–384.

Biggar WD, Sturgess JM. Role of lysozyme in the microbicidal activity of rat alveolar macrophages. *Infection and Immunity* 1977; 16(3): 974–982.

Billek G, Billek D. Hyaluronsaure –Die Gesch . . . eines kosmetischen wirkstoffs. [Summary in English] *Parfuemerie und Kosmetik* 1988; 69(12): 768–790 & 792–795.

Binkhorst CD. Advantages and disadvantages of intracamerular Na–Hyaluronate (Healon) in intraocular lens surgery. *Documenta Ophthalmologica* 1981; 50: 233–235.

Blumenkrantz N, Asboe–Hansen G. Reaction of cationic groups of chlorpromazine with anionic macromolecules: Complexes with DNA, RNA, hyaluronic acid and heparin. *Acta Pharmacol. et Toxiicol.* 1974; 34: 27–32.

Bowen BR, Nguyen T, Lasky LA. Characterization of a human homologue of the murine peripheral lymph node homing receptor. *J Cell Biology* 1989; 109(Jul.):421–427.

Boyce ST, Christianson DJ, Hansbrough JF. Structure of a collagen–GAG dermal skin substitute optimized for cultured human epidermal keratinocytes. *J. Biomedical Material Research* 1988; 22: 939–957.

Brandstetter W, Kiesewetter E, Wohlzogen FX. Influencing experimental pathological changes i rodents with hyaluronic acid. [Translation of: Beeinflussung experimentell–pathologischer veranderungen bei nagern durch hyaluronsaure.] *Archive for Experimental Pathology and Pharmacology / Archiv Fur Experimentelle Pathologie* 1957; 231(2): 186–198.

Brandt K. Modification of chemotaxis by synovial fluid hyaluronate. *Arthritis and Rheumatism* 1970; 13(3): 308–309.

Brown TA, Bouchard T, St. John T, Wayner E, Carter WG. Human keratinocytes express a new CD44 core protein (CD44E) as a heparan–sulfate intrinsic membrane proteoglycan with additional exons. *J Cell Biology* 1991; 113(1): 207–221.

Bruno RN. Osservazioni sull'impiego comparativo di sale sodico dell'acido ialuronico e dell'estratto di *Triticum vulgaris* in 20 casi di soggetti affetti da ulcere a deversa etiologia. [Summary in English] *Il Policlinico. Sezione Medica:* 1983; 90(4): 340–344.

Burk DT. Morphological effects of streptomyces hyaluronidase treatment on the ouitgrowht of the nasal processes in mouse embryos. *J Craniofacial Genetics* 1985; 5: 385–398.

Carbonetto S, Gruver MM, Turner DC. Nerve Fiber grwoth in culture on fibronectin, collagen, and glycosaminoglycan substrates. *J. Neuroscience* 1983; 3(11): 2324–2335.

Chang N-S. Hyaluronic acid and complement interactions. *Dissertation Abstracts International* 1985; 45(12): 3766–B.

Chen WYJ, Grant ME, Schor AM, Schor SL. Differences between adult and foetal fibroblasts in the regulation of hy: Correlation with m8igratory activity. *J Cell Science* 1989; 94: 577–584.

Cifonelli JA. The isolation and characterization of hyaluronic acid from Pasteurella multocida. *Carbohydrate Research* 1970; 14: 272–276.

Cifonelli JA, Dorfman A. The biosynthesis of hyaluronic acid by group A Streptococcus: The uridine nucleotides of groups A Streptococcus. *J. Biological Chemistry* 1957; 228: 547–557.

Cleary PP, Larkin A. Hyaluronic acid capsule: Strategy for oxygen resistance in group A streptocci. *J Bacteriology* 1979; 140(3): 1090–1097.

Cleland RL. Molecular weight distribution in hyaluronic acid. In: *Chemistry and Molecular Biology of the Intercellular Matrix*. Edited by EA Balazs. Boston: Academic Press, 1970:733–742.

Comper WD, Laurent TC. Physiological function of connective tissue polysaccharides. *Physiological Reviews* 1978 (Jan.); 58(1): 255–305.

Costantini A, Muzzio A, Agus GB. Plethysmographic patterns in scleroderma after percutaneous G.A.G. treatment. *Bolletinno Chimico Farmaceutico* 1986; 125(10): 111s–115s.

Cullis–Hill D, Ghosh P. The role of hyaluronic acid in joint stability: A hypothesis for hip dysplasisa and allied disorders. *Medical Hypothesis* 1987; 23: 171–185.

Culty M, Miyake K, Kincade PW, Silorski E, Butcher EC. The hyaluronate receptor is a member of the CD44 (H–CAM) family of cell surface glycoproteins. *J Cell Biology* 1990; 111(6, pt. 1): 2765–2774.

Curri SB. Influence of the hyaluronic acid on the restoration processes of the muscular–cutaneous planes. [Translation of: Influenza dell'acido jaluronico sui processi riparativi dei piani cutaneo–muscolari.] *Bulletin of the Italian Society for Experimental biology/Bollettino Della Societa Italiana Di Biologia Sperimentale* 1959; 35(23): 1762–1768.

Dahl IM. Biosynthesis of proteoglycans and hyaluronate in human fibroblast cultures established from normal and pathological corneas. *Exp. Eye Research* 1981; 32: 435–443.

Dahlgren C, Bjorksten B. Effect of hyaluronic acid on polymorphonuclear leucocyte cell surface properties. *Scand. J Haematol.* 1982; 28: 376–380.

Dasch W, von, Braun E, Nowack H. Transdermale salicylat–resorption und verhalten des corticosteroi plasmaspiegels nach epidermater applikation einer antiphlogistis wirksamen salbe. [Summary in English] *Arzneim.-Forsch.* 1983; 33(8): 1196–1199.

Davidson JF, Walker ID. Synthetic fibrinolytic agents. *Progress in Cardiovascular Diseases* 1979; XXI(5): 375–396.

De Buman M, Walther M, de Weck R. Wirksamkeit der Alphastria–Creme bei der Vorbeugung von Schwangerschaftsstreifen (Striae distensae). [Summary in English] *Gynak. Rdsch.* 1987; 27: 79–84.

Deguchi T, Ishii A, Tanaka M. Binding of aminoglycoside antibiotics to acidic mucopolysaccharides. *The Journal of Antibiotics* 1978; 31(2): 150–155.

Delmage JM, Powars DR, Jaynes PK, Allerton SE. The selective suppression of immunogenicity by hyaluronic acid. *Annals of Clinical and Laboratory Science* 1986; 16(1): 303–310.

Delpech A, Delpech B, Girard N, Boullie MC, Lauret P. Hyaluronectin in normal human skin and in basal cell carcinoma. *British J Dermatology* 1982; 106: 561–568.

Di Cicco LM, Mansbridge JN, Morhenn VB. Inhibition of attachment and growth of tumor cells on collagen by a monoclonal antibody. *In Vitro Cellular & Developmental Biology* 1987; 23(12): 805–814.

Doege KJ, Sasaki M, Kimura T, Yamada Y. Complete coding sequence and deduced primary structure of the human cartilage large aggregating proteoglycan, Aggrecan. *J Biological Chemistry* 1991; 266(2): 894–902.

Doillon CJ, Silver FH Collagen–based wound dressing: Effects of hyaluronic acid and fibronectin on wound healing. *Biomaterials* 1986; 7(Jan.): 3–8.

Drobnik J. Hyaluronan in drug delivery. *Advanced Drug Delivery Reviews* 1991; 7: 295–308.

Elling H. Immunofluorescence demostration of transdermal deposition of mucopolysaccharides into the skin. *Arzneim.-Forsch.* 1987; 37(7): 816–818.

Elling H. Penetration of mucopolysaccharides into the skin of diverse animal species. *Arzneim–Forsch.* 1986; 36(10): 1505–1507.

Fatini G, Gallenga G, Veltroni A. The treatment of burns with hyaluronic acid.[Translation of: Il trattamento delle ustioni con acido jaluronico.] *Hospitals of Italy Surgery / Ospedali D'Italia Chirurgia* 1968; 19(3): 283–287.

Faulstich H, Weckauf M. Cytolysis of red cells mediated by phallolysin, a toxin binding to N–Acetylgucosamine on the cell surface. *Hoppe–Seyler's Z. Physiol. Chem.* 1975; Bd. 356 (Jul.): 1187–1189.

Feige JJ, Pirollet F, Cochet C, Chambaz EM. Selective inhibition of a cyclic nucleotide–independent protein kinase (G–type casein Kinase) by naturally occurring glycasaminoglycans. *Febs Letters/Elsevier/Nd Biomedical Press* 1980; 21(1): 139–142.

Forrester JV, Lackie JM. Effect of Hyaluronic acid on neutrophil adhesion. *J Cell Sci.* 1981; 50: 329–344.

Fraser JRE, Murcoch WS, Curtain CC, Watt BJ. Proteins retained with hyaluronic acid during ultrafiltration of synovial fluid. *Connective Tissue Research* 1977; 5: 61–65.

Gandrille S, Aiach M, Lane DA, Vidaud D, et al. Important role of Arginine 129 in Heparin–binding site of Antithrombin III. *J Biological Chemistry* 1990; 265(31): 18997–19001.

Gaughan EM, Nixon AJ, Krook LP, Yeager AE, et al. Effects of sodium hyaluronate on tendon healing and adhesion formation in horses. *Am. J. Vet. Res.* 1991; 52(5): 764–773.

Gill WB, Jones KW, Ruggiero KJ. Protective effects of heparin and other sulfated glycosaminoglycans on crystal adhesion to injured urothelium. *J Urology* 1982; 127(1): 152–154.

Gingerich DA. Effect of exogenous hyaluroxperimentally induced equine osteoarthritis: Dosage titration studies. *Research in Veterinary Science* 1981; 30: 192–197.

Ginsburg I. The biochemistry of bacteriolysis: Paradoxes, facts and myths. *Microbiological Sciences* 1988; 5(5): 137–142.

Ginsburg I, Sela MN, Morag A, Ravid Z, Duchan Z, et al. Role of leukocyte factors and cationic polyelectrolytes in phagocytosis of group A streptococci and *Candida albicans* by neutrophils, macrophages, fibroblasts and epithelial cells: Modulation by anionic polyelectrolytes in relation to pathogenesis of chronic inflammation. *Inflammation* 1981; 5(4): 289–312.

Goetenck PF, Stirpe NS, Tsonis PA, Carlone D. The tandemly repeated sequences of cartilage link protein contain the sites for interaction with hyaluronic acid. *J Cell Biology* 1987; 105: 2403–2408.

Gorog P, Raake W. Antithrombotic effect of a mucopolysaccharide poly-sulfate after systemic, topical and percutaneous application. *Arzneim.-Frosch.* 1987; 37(3): 342–345.

Granger HJ, Laine SH, Laine GA. Osmotic pressure exerted by entangled polysaccharide chains. *Microcirculation, Endothelium, and Lymphatics* 1985; 2: 85–105.

Graue EL, Polack FM, Balazs EA. The protective effect of Na-hyaluronate to corneal endothelium. *Exp. Eye Research* 1980; 31: 119–127.

Gregoriadis G. Carrier potential of liposomes in biology and medicine (Part 1 of 2). *New England J Medicine* 1976; 295: 704–710.

Greiling H, et al. B–Elimination reaction in amino acid containing hyaluronic acid preparations. In: *Chemistry and Molecular Biology of the intercellular Matrix.* Edited by EA Balazs. New York: Academic Press, 1970: 759–762.

Gustafson SB, McIlwraith W, Jones RL. Comparison of the effect of polysulfated glycosamino–glycan, corticosteroids, and sodium hyaluronate in the potentiation of a subinfective dose of *Staphlyococcus aureus* in the midcarpal joint of horses. *Am. J. Vet. Res.* 1989; 50(12): 2014–2017.

Hakansson L, Vange P. The combined action of hyaluronic acid and fibronectin stimulates neutrohil migration. *Journal of Immunology* 1985; 135(4): 2735–2739.

Hakansson L, Hallgren R, Venge P. Regulation of granulocyte function by hyaluronic acid. *J. Clin. Invest.* 1980; 66: 298–305.

Hakansson L. Hyaluronic acid stimultes neutrophil function in vitro and in vivo. *Scandanavian J. Infectious Dis. Suppl.* 1980; 24: 54–57.

Hoshino O, Zehavi U, et al. The isolation and structure identification of a disaccharide containing manno–muramic acid from *Micrococcus lysodeikticus* cell wall. *Journal of Biological Chemistry* 1972; 247(2): 381–390.

Hughes EN, Colombatti A, Qugust JT. Murine cell surface glycoproteins. *J Biological Chemistry* 1983; 258(2): 1014–1021.

Idson B. Formulation for treatment of aging skin problems. *Drug and Cosmetic Industry* 1988; 142(Jan.): 36, 38, 84.

Idson B. "Natural" moisturizers for cosmetics. *Drug and Cosmetic Industry* 1985; 136(5)(May): 24–26.

Iozzo RV. Proteoglycans: Structure, function, and role in neoplasia. *Laboratory Investigation* 1985; 53(4): 373–396.

Irwin DHG. Sodium hyaluronate in equine traumatic arthritis. *J. of the South African Veterinary Association* 1980; 50(4):231–233.

Jacobs RR, McClain O, Neff J. Control of postlaminectomy scar formation: An experimental and clinical study. *Spine* 1980; 5(3):223–229.

Jacobson B. The biosynthesis of hyaluronic acid. In: *Chemistry and Molecular Biology of the Intracellular Matrix::vol. 2, Glycosamionglycans and Proteoglycans*, Edited by EA Balazs. New York: Academic Press, 1970.

Jarvelainen H, Ronnemaa T, Tammi M, et al. Type IIA hyperlipoproteinemic sera secrease the synthesis of hyaluronic acid by cultured human aortic smooth muscle cells. *Atherosclerosis* 1981; 39: 61–69.

Jeanloz RW. Mucopolysaccharides of higher animals. In: *The Chemistry and Biology of Compounds Containing Amino Sugars.* New York: Academic Press, 1969. pp. 589–625.

Joshi HN. In vitro characterization of membranes of hyaluronic acid and its esters. *Dissertation Abstracts International* 1993; 53(11): 5731–B.

Katona G. A clinical trial of glycosaminoglycan–peptide complex ("Rumalon") in patients with osteoarthritis of the knee. *Current Medical Research and Opinion* 1987; 10(9): 625–633.

Keller N. Alteration of the hydrodynamic properties of hyaluronate solutions by corticosterone. *Biochimica et Biophysica Acta* 1967; 148: 757–766.

Kendall FE, et al. A serologically inactive polysaccharide elaborated by mucoid strains of group A hemolytic Streptococcus. *J Biological Chemistry* 1937; 118: 61–69.

Kielty CM, Whittaker SP, Grant ME, Shuttleworth CA. Typ VI collagen microfibrils: Evidence for a structural association with hyaluronan. *The Journal of Cell Biology* 1992; 118(4): 979–990.

Kimata K, Hascall VC, Kimura JH. Mechanisms for dissociating proteoglycan aggregates. *J Biol Chemistry* 1982; 257(7): 3827–3832.

Kimoto E, Tanaka Y, Abe T. Interaction between acid mucopolysaccharides and basic noxious substances. *The Kurume Medical Journal* 1960; 7(1): 1–12.

Kirchberger MA, Martin DG, Leaf A, Sharp GW. The effect of aldosterone on glucose metabolism in toad bladder. *Biochimica et Biophysica Acta* 1968; 165: 22–31.

Kjems E, Lebech K. Isolation of hyaluronic acid from cultures of streptococci in a chemically defined medium. *Acta Path. Microbiol. Scand.* 1976 (Sect. B); 84: 162–164.

Kopp S, Benneberg B, Haraldson T, Carlsson GE. The short–term effect of intra–articular injections of sodium hyaluronate and corticosteroid on temporomandibular joint pain and dysfunction. *Oral Maxillofac. Surg.* 1985; 43:429–435.

Kopp S, Carlsson GE, Haraldson T, Wenneberg. Long–term effect of intra–articular injections of sodium hyaluronate and corticosteroid on temporamandibular joint arthritis. *Oral. Maxillofac. Surg.* 1987; 45:929–935.

Krusius T, Gehlsen KR, Ruoslahti E. A fibroblast chondroitin sulfate proteoglycan core protein contains lectin–like and grwoth factor–like sequences. *J. Biol. Chemistry* 1987; 262(27): 13120–13125.

Ksander GA, Vistnes LM. Collagen and glycosaminoglycans in capsules around silicone implants. *J. Surgical Research* 1981; 31:433–439.

Larsen NE, Balazs EA. Drug delivery systems using hyaluronan and its derivatives. *Advanced Drug Delivery Reviews* 1991; 7: 279–293.

Laurent TC. Structure of hyaluronic acid. In: *Chemistry and Molecular Biology of the Intercellular Matrix.. Vol. i, II, III.* Edited by EA Balazs. New York: Academic Press, 1970. pp. 703–773.

Laurent TC. The interaction between polysaccharides and other macromolecules. *Biochemical Journal* 1963; 89(2): 253–257.

Laurent TC, Pietruszkiewicz A. The effect of hyaluronic acid on the sedimentation rate of other substances. *Biochimica et Biophysica Acta* 1961; 49(2): 258–264.

Laurent UBG, Granath KA. The molecular weight of hyaluronate in the aqueous humour and vitreous body of rabbit and cattle eyes. *Experemental Eye Research* 1983; 36: 481–492.

Laurent UBG, Fraser JRE. Turnover of hyaluronate in the aqueous humour and vitreous body of the rabbit. *Experimental Eye Research* 1983; 36:493–504.

LeBoeuf RD, Gregg RR, et al. Effects of hyaluronic acid and other glycosaminoglycans on fibrin polymer formation. *Biochemistry* 1987; 26: 6052–6057.

Lee KH, Spencer MR. Studies on mechanism of action of salicylates V: Effect of salicylic acid on enzymes involved in mucopoly–saccharides synthesis. *J. Pharmaceutical Sciences* 1969; 58: 464–468.

LeVeen HH, Franklin E, Barberio JR. The Use of hyaluronic acid for fixation of skin grafts. *Surgery* 1951; 29(5): 743–747.

Lindahl U, Hook M. Glycosaminoglycans and their binding to biological macromolecules. *Annual Review of Biochemistry* 1978; 47: 385–417.

Little CB, Hilbert BJ, Wickstrom S, Hedlund BE. Quantitative microanalysis of equine synovial fluid glycosaminoglycan concentration. *Am. J. Vet. Res.* 1990; 51(10): 1534–1539.

Longas OM, et al. Sequential hydrolysis of hyaluronate by B–Glucuronidase and B–N–Acetylhexosaminadase. *Biol. Chem. J.* 1981; 197: 275–282.

Lowther DA. The Role of glutamine in the biosynthesis of hyaluronate by streptococcal suspensions. *Biochemical Journal* 1956; 62: 304–314.

Maguen E, Besburn AB, Macy JI. Combined use of sodium hyaluronate and tissue adhesive in penetrating deratoplasty of corneal perforations. *Ophthalmic Surgery* 1984 (Jan.); 15: 55–57.

Malark JA, Nixon AJ, Skinner KL, Mohammed H. Characteristics of digital flexor tendon sheath fluid from clinically normal horses. *Am. J. Vet. Res.* 1991; 52(8): 12921294.

Mapleson JL, Buchwald M. Effect of cycloheximide and dexamethasone phosphate on hyaluronic acid synthesis and secretion in cultured human skin fibroblasts. *J. Cellular Physiology* 1981; 109: 215–222.

Markovitz A, et al. The biosynthesis of hyaluronic acid by group A Streptococcus. *J. Biological Chemistry* 1959; 234(9): 2343–2350.

Maroudas NG, Lindenbaum ES. Polymer treatments reduce adhesion of comminuted stone in rat bladder. *British J Urology* 1987; 59: 519–522.

Martin DE, Reece M, Reese AC. Effect of plasma fibronectin, macrophages, and glycosaminoglycans on tumor cell growth. *Cancer Investigation* 1984; 2(5): 339–345.

Mazzone A, Baiguera R, Rossini S, et al. Pharmacological effect of yaluronic acid (HA) on phagocytes: Hypothesis for an HA–induced monocyte chemotatic factor for neutrophils. *Clinical Therapeutics* 1986; 8(5): 527–536.

McCulloch JA Chemonucleolysis: Experience with 2000 cases. *Clinical Orthopaedics and Related Research* 1980; 146 (Jan.–Feb.): 128–135.

McLean D. The capsulation of *Streptococci* and its relation to diffusion factor (hyaluronidase). *J Pathology & Bacteriology* 1941; 53: 13–27.

Mehta PP, Sagar S, Kakkar VV. Treatment of superficial thrombophlebitis: A randomized, double–blind trial of heparinoid cream. *British Medical Journal* 1975; 3: 614–616.

Mejersjo C. TMJ Osteroarthrosis. *J Craniomandibular Practice* 1987; 5(1): 73–78.

Mejersjo C, Kipp S. Effect of corticosteroid and sodium hyaluronate on induced joint lesions in the guinea–pig knee. *Int. J. Oral Maxillofac. Surg.* 1987; 16: 194–201.

Mejersjo C. Ph.d. Thesis: *Long–Term Development After Treatment of Mandibular Dysfunction and Osteroarthrosis: A Clinical–Radiographic Follow–up and an Animal Experimental Study*. Department of Stomatognathic Physiology, Faculty of Odontology, University of Goteborg, Goteborg, Sweden, 1984 (ISSN 0348–6672; ISBN 91–7222–758–3).

Mendler N, Schrock N. Osmotic properties of macromolecular solutions and gels: Physical Aspects and Physiological Relevance. In: *Hemodilution.: Theoretical Basis and Clinical Application*. Int. Symp. Rottach–Egern. Basel: Karger, 1972: 105–117.

Meyer K. Reflections on "mucopolysaccharides" and their protein complexes. In: *Chemistry and Molecular Biology of the Intercellular Matrix vol. 1*. Edited by EA Balazs. New York: Academic Press, 1970: pp. 5–24.

Meyer K, et al. The hydrolysis of the polysaccharide acids of vitreous humor, of umbilical cord, and of streptococcus by the autolytic enzyme of pneumococcus. *J. Biological Chemistry* 1937; 118: 71–78.

Miller D, Stegmann R. Use of Na–hyaluronate in auto–corneal transplantation in rabbits. *Opthalmic Surgery* 1980; 11(1): 19–21.

Miyake K, Underhill CB, Lesley J, Kincade PW. Hyaluronate can function as a cell adhesion molecule and CD44 participates in hyaluronate recognition. *J Exp. Med.* 1990; 172: 69–75.

Myers SL. Suppression of hyaluronic acid synthesis in synovial organ cultures by corticosteroid suspensions. *Arthritis and Rheumatism* 1985; 28(11): 1275–1282.

Nambisan B, Kurup PA. Ascorbic acid and glycosaminoglycan and lipid metabolism in guinea pigs fed normal and atherogenic diets. *Atherosclerosis* 1975; 22: 447–461.

Namiki O, Toyoshima H, Morisaki N. Therapeutic effect of intra–articular injection of high molecular weight hyaluronic acid on osteoarthritis of the knee. *International J Clinical Pharmacology, Therapy and Toxicology* 1982; 20(11): 501–507.

Neame PJ, Christner JE, Baker JR. Cartilage proteoglycan aggregates. *J Biol. Chemistry* 1987; 262(36): 17768–17778.

Neame PJ, Christner JE, Baker JR. The primary structure of link protein from rat chondrasarcoma proteoglycan aggregate. *J Biol. Chemistry* 1986; 261(8): 3519–3535.

Neame PJ, Perin J–P, Bonnet F, Christner JE, Jolles P, Baker JR. An amino acid sequence common to both cartilage proteoglycan and link protein. *J Biol. Chemistry* 1985; 260(23): 12402–12404.

Nehme D, Fingerhut B, Veenema RJ. Effect of a mucopolysaccharide cream on tissue metabolism. *International Surgery* 1973; 58(3): 171–173.

Nettelbladt O, Tengblad A, Hallgren R. High dose corticosteroids during bleomycin–induced alveolitis in the rat do not suppress the accummulation of hyaluronan (hyaluronic acid) in lung tissue. *Eur. Respir. J.* 1980; 3: 421–428.

Niemann H, Birch–Andersen A, Kjems E, Mansa B, Stirm S. Streptococcal bacteriophage 12/12–borne hyaluronidase and its characterizarization as a lyase (EC 4.2.99.1) by means of streptococcal hyaluronic acid and purified bacteriophage suspensions. *Acta Path. Microbiol. Scand.* 1976 (Sect. B); 84: 145–153.

Nitzan DW, Pruzanski W, Saito S, Ranadive N. Modulation of locomotor activity of polymorphonuclear cells by cationic substances and cationic lysosomal fractions from human neutrophils. *Inflammation* 1985; 9(4): 375–387.

O'Brien WF, Drake RS, Bibro MC. The use of ibuprofen and dexamethasone in the prevention of postoperative adhesion formation. *Obstetrics & Gynecology* 1982; 60(3): 373–378.

Ogson AG. The biological functions of the glycosaminoglycans. In: *Chemistry and Molecular Biology of the Intercelular Matrix. vol. III.* Edited by EA Balazs. New York: Academic Press, 1970. pp. 231–1240.

Olesen ES. Fibrinolytic activity produced in guinea–pig serum by some human body fluids and by hyaluronic acid. *Scandinavian Journal of clinical & Laboratory Investigation* 1961; 13(1): 37–43.

Otsuka K, Mori Y. Inhibitory effect of D–penicillamine on degrqadation of hexosamine–containing substances in the involution of carrageenin granuloma induced by calcium chelate ethylenediaminetetraacetate. *Chem. Pharm. Bull.* 1976; 24(2): 215–219.

Pal MK, Nath J. Separation of hyaluronate, chondroitin sulfate, and heparin by adsorption–desorption technique. *Analytical Biochemistry* 1974; 57: 395–402.

Passarini B, Tosti A, Fanti PA, Varotti C. Effetto dell'acido ialuronico sul processo reparativo delle ulcere trofiche. [Summary in English] *Giornale Italiano di Dermatologia e Venereologia* 1982; 117: XXVII–XXX.

Pigman W, et al. Preparation and stability of hyaluronic acid. *Biochim. Biophys. Acta* 1961; 53: 254–262.

Pinkus H, Perry ET. The influence of hyaluronic acid and other substances on tensile strength of healing wounds. *J. Investigative Dermatology* 1953; 21: 365–374.

Polefka TG. The passive permeability properties and cell surface characteristics of the novikoff hepatoma ascites cell. *Dissertation Abstracts International* 1980; 41(4): 1216B.

Popovici GG, Haulica I, Botez E. The action of some antibiotics on tissular diffusibility. *Revue Roumaine de Physiologie* 1971; 8(6): 503–509.

Pruzanski W, Ranadive NS, Saito s. Modulation of phagocytosis and intracellular bactericidal activity of polymorphonuclear and mononuclear cells by cationic proteins from human granulocytes. *Inflammation* 1984; 8(4): 445–457.

Repaske R, Repaske AC, Mayer RD. Carbon dioxide control of lag period and grwoth of Streptococcus sanguis. *J. Bacteriology* 1974; 117(2): 652–659.

Rosner IA, Boja BA, Malemud CJ, et al. Intraarticular hyaluronic acid injection and synovial prostaglandins in experimental immune synovitis. *J. Rheumatology* 1983; 10:71–78.

Rydell NW, Butler J, Balazs EA. Hyaluronic acid in synovial fluid. VI Effect of intra–articular injection of hyaluronic acid on the clinical symptoms of arthritis in track horses. *Acta Veterinaria Scandinavica* 1970; 11(2): 139–155.

Saar(n)i H, Jalkanen M, Hopsu–Havu VK. Effect of five anti–inflammatory steroids on collagen and glycoaminoglycan synthesis in vitro. *British Journal of Dermatology* 1980; 103: 167–173.

Saar(n)i H, Tulamo R–M, Konttinen YT, Sorsa T. Methylprednisolone acetate induced release of cartilage proteoglycans: Determination by high performance liquid chromatolgraphy. *Annals of the Rheumatic Diseases* 1992; 51(2): 214–219.

Saar(n)i H, Hopsu–Havu VK. The decrease of hyaluronate synthesis by anti–inflammatory steroids in vitro. *British Journal of Dermatology* 1978; 98: 445–449.

Saar(n)i H, Konttinen YT, Tulamo R–M, Antti–Poika I, Honkanen V. Concentration and degree of polymerization of hyaluronate in equine synovial fluid. *Am. J. Vet. Res.* 1989; 50(12): 2060–2063.

Saba HI. Hemophilia and allied conditions. *Current Therapy* 1978; 280–288.

Salter MKC. Optical Studies of Acridine orange–glycosaminoglycan complexes in aqueous solution. *Dissertation Abstracts International* 1977; 12(Part 1): 6159B–6160B.

Schecter B, Neumann A, Wilchek M, Arnon R. Soluble polymers as carriers of cis–platinum. *J. Controlled Release* 1989; 10: 75–87.

Schmut O, Hofmann H. Preparation of gels from hyualuronate solutions. *Graefe's Arch. Clin. Exp. Ophthalmol.* 1982; 218: 311–314.

Schmut O, Hofmann H. A method for the purification of bovine vitreous body hyaluronic acid. *Biochimica et Biophysica Acta* 1981; 673: 192–196.

Schmut O, Hofmann H. Studies on the generation of hydrogen peroxide during some non–enzyme reactions changing the hyaluronic acid molecule. *Biochimica et Biophysica Acta* 1975; 411: 231–235.

Shanley DJ, Cossu G, Boettiger D, Holtzer H, Pacifici M. Transformation by Rous Sarcoma Virus induces similar patterns of glycosaminoglycan synthesis in chick embryo skin febroblasts and bertebral chondroblasts. *J. Biol. Chemistry* 1983; 258(2): 810–816.

Shannon BT, Love SH, Roh BH, Schroff RW. Quantitation of glycosaminoglycans of rabbit lung during delayed–type hypersensitivity reactions and granuloma formation. *Inflammation* 1981; 5(4): 323–334.

Shannon BT, Love SH, Myrvik QN. Participation of hyaluronic acid in the macrophage disappearance reaction. *Immunological Communications* 1980; 9(4): 357–370.

Shepherd MG, Sullivan PA. The control of morphogenesis in Candida albicans. *J Dent. Res.* 1984; 63(3): 435–440.

Shimada E, Matsumura G. Molecular weight of hyaluronic acid from rabbit skin. *J. Biochemistry* 1977; 81: 79–91.

Singh Ch, Mistra J. Some properties of deoxycholate and dodecyl sulphate in relation to macroionic complexes and their biochemical implications. *Arzneim.–Forsch.* 1978; 28(8): 1320–1327.

Sneader WE, Florence AT, McColl E. A possible mechanism for the action of dimethyl sulphoxide on percutaneous absorption. *J. Pharmacy & Pharmacology* 1971; 23 (Suppl.): 252s.

Sparer RV. Controlled Release of Drugs from Glycosaminoglycan Drug Complexes. *Dissertation Abstracts International* 1983; 43(9): 2921B.

Stacey M, Barker SA. Hyaluronic acid. In: Carbohydrates of Living Tissues. By: Stacey M, Barker SA. London: D. Van Nostrand Co. Ltd., 1962: 37–58.

Stangel JJ, Nisbet II JD, Settles H. Formation and prevention of postoperative abdominal adhesions. *J Reproductive Medicine* 1984; 29(3):43–156.

Stegman R, Miller D. Extracapsular cataract extraction with hyaluronate sodium. *Annals of Opthalmology* 1982; Sep.:813–815.

Stenfors L–E. Treatment of tympanic membrane perforations with hyaluronan in an open pilot study of unselected patients. *Acta Otolaryngol (Stockh)* 1987; Suppl. 442:81–87.

Stoolmiller AC, Dorfman A. The biosynthesis of hyaluronic acid in group A Streptococci. In: *Chemistry and Molecular Biology of the Intercellular Matrix*. Edited by EA Balazs. Boston: Academic Press, 1970. pp. 783–794.

Stuttgen G, Panse P, Bauer E. Permeation of the human skin by heparin and mucopolysaccharide polysulfuric acid ester. *Arzneim.–Forsch.* 1990; 40(4): 484–489.

Sugahara et al. Biosynthesis of HA by Streptococcus. *J. Biological Chemistry* 1979; 254(14):6252–6261.

Suzuki, Sakaru. (Dep't. of Chemistry, Faculty of Science, Nagoya University.) Symposium III Interaction between cell Stromata and Cancer: Interaction between cells and Stromata in the Course of Cancer Cell Metastasis. [English Translation] *Japanese Journal of Cancer and Chemotherapy* 1984; 11(3): 557–780.

Swann DA, Radin EL, Nazimiec M, Weisse PA, Curran N, et al. Role of hyaluronic acid in joint lubrication. *Ann. Rheum. Dis.* 1974; 33: 318–326.

Swann DA. On the state of hyaluronic acid in a connective tissue matrix. In: *Chemistry and Molecular Biology of the intercellular Matrix.*. Edited by EA Balazs. New York: Academic Press, 1970: 743–748.

Swann DA. Studies on hyaluronic acid: The preparation and properties of Rooster Comb hyaluronic acid. *Biochem. Biophs. Acta.* 1968; 156: 17–30.

Thomas SC, Jones LC, Hungerford DS. Hyaluronic acid and its effect on postoperative adhesions in the rabbit flexor tendon: A preliminary look. *Clinical Orthopaedics and Related Research* 1986; 206: 281–289.

Tonn SJ, Gander JE. Biosynthesis of polysaccharides by prokaryotes. *Ann. Rev. Microbiol.* 1979; 33: 169–199.

Treadway WJ, et al. The role of hyaluronic acid flux on modulation of neutrophil function. *Arthritis and Rheumatism* 1981; 24(4) (Suppl): 218.

Trimble WS, Johnson PW, Hozumi N, Roder JC. Inducible cellular transformation by a metallothionein–ras hybrid oncogene leads to natural killer cell susceptibility. *Nature* 1986; 321: 782–784.

Tulamo R–M. Comparison of high–performance liquid chromatography with a radiometric assay for determination of the effect of intra–articular administration of corticosteroid and saline solution on synovial fluid hyaluronate concentration in horses. *Am. J. Vet. Res.* 1991; 52(12): 1940–1944.

Tulamo R–M, Saar(n)i H, Konttinen YT. Determination of concentration of hyaluronate in equine serum. *Am. J. Vet. Res.* 1990; 51(5): 740–742.

Turley EA, Austen K, Vandeligt, Clary C. Hyaluronan and a cell–associated Hyaluronan binding protein regulate the locomotion of Ras–transformed cells. *The Journal of Cell Biology* 1991; 112(5): 1041–1047.

Turley E, Tretiak M, Tanguay K. Effect of glycosaminoglycans and enzymes on the integrity of human placental amnion as a barrier to cell invasion. *JNCI* 1987; 78: 787–795.

Turner TW, Gale AE. Urticaria. *Australian Family Physician* 1978; 12: 1497–1501.

Underhill CB, Green SJ, Comoglio PM, Tarone G. The hyaluronate receptor is identical to a glycoprotein of Mr 85,000 (gp85) as shown by a monoclonal antibody that interferes with binding activity. *J. Biol. Chem.* 1987; 262(27): 13142–13146.

Uzuka M, et al. The mechanism of estrogen–induced increase in hyaluronic acid biosynthesis, with special reference to estrogen receptor in the mouse–skin. *Biochimica et Biophysica Acta* 1980; 627: 199–206.

Vaheri A. Heparin and related polyionic substances as virus inhibitors. *Acta Pathologica et Microbiologica Scandinavica. Supplementum* 174, 1964: 1–98.

van de Rijn I, van de, Kessler RE. Growth characteristics of Group A Streptococci in a new chemically defined medium. *Infection and Immunity* 1980; 27(2): 444–448.

Verstraeten TC, Wilcox DK, Friberg TR, Reel C. Effects of silicone oil and hyaluronic acid on cultured human retinal pigment epithelium. *Investigative Ophthalmology & Visual Science* 1990; 31(9): 1761–1766.

Vuorio E, Takala I, et al.. Effects of sodium aurothiomalate on hyaluronic acid synthesis in normal and rheumatoid synovial fibroblast cultures. *Scandinavian Journal of Rheumatology* 1979; 8: 173–176.

Wasteson A, Westermark B, Lindahl U, Ponten J. Aggregation of feline lymphoma cells by hyaluronic acid. *Int. J Cancer* 1973; 12: 169–178.

Welter DA, Hodge LD. A scanning electron microscopic technique for three–dimensional visualization of the spatial arrangement of metaphase, anaphase and telophase chromatids. *Scanning Electron Microscopy* 1985; II: 879–888.

Whitnack E, Bisno AL, Beachey EH. Hyaluronate capsule prevents attachment of group A streptococci to mouse peritoneal macrophages. *Infection and Immunity* 1981; 31(3): 985–991.

Wigrin A, Falk J, Wik O. The healing of cartilage injuries under the influence of joint immobilization and repeated hyaluronic acid injections. *Acta Orthop. Scand.* 1978; 49: 121–133.

Wolf RE, et al. Growth–rate–dependent alteration of 6–phospho–gluconate dehydrogenase and glucose 6–phosphate dehydrogenase levels in *Escherichia coli* K–12. *J. Bacteriology* 1979; 139(3): 1093–1096.

Wu TC, Trask LM, Phee RE. Comparison of media and culture techniques for detection of *Streptococcus pneumoniae* in respiratory secretions. *J Clinical Microbiology* 1980; 12(6): 772–775.

Yaron M, Yaron I, Herzberg M. Levamisole in rheumatoid arthritis [letter]. *Lancet* 1976; Feb. 14 : 369.

Yuzawa K. Experimental studies on the healing and restoration of gliding function of the injured digital flexor tendon. [Summary in English] *J. Jpn. Orthop. Ass.* 1985; 59: 1107–1118.

Zakut–Houri R, Oren M, Bienz B, Lavie V, Hazum S, Givol D. A single gene and a pseudogene for the cellular tumour antigen p.53. *Nature* 1983; 306: 594–597.

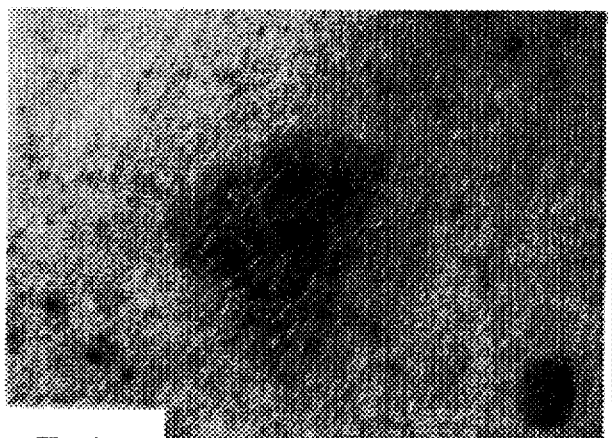
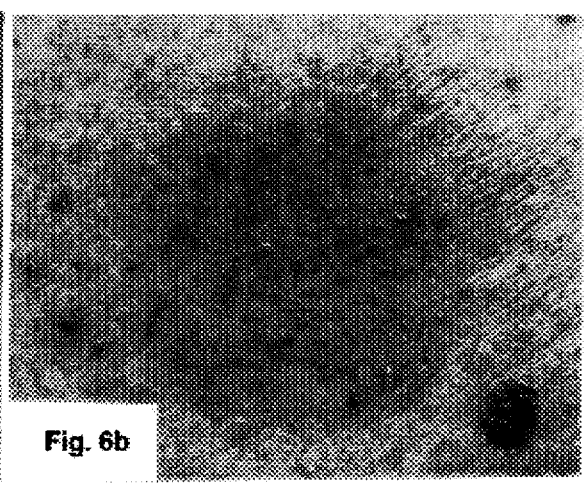
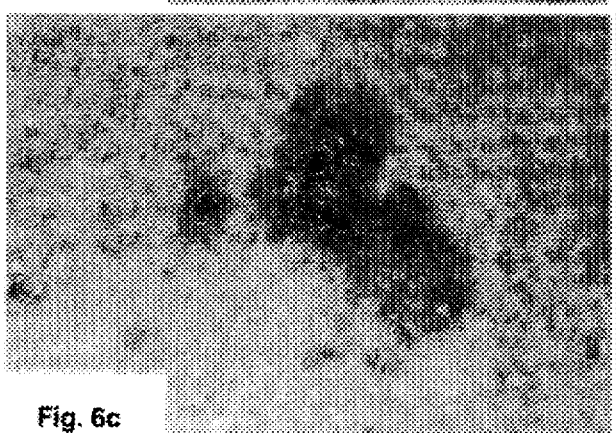
Fig. 6a
Fig. 6b
Fig. 6c
Fig. 6d

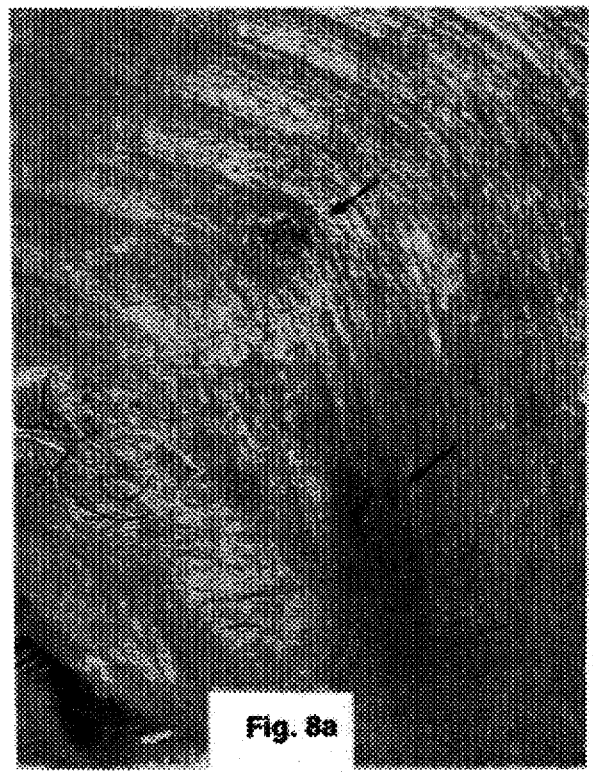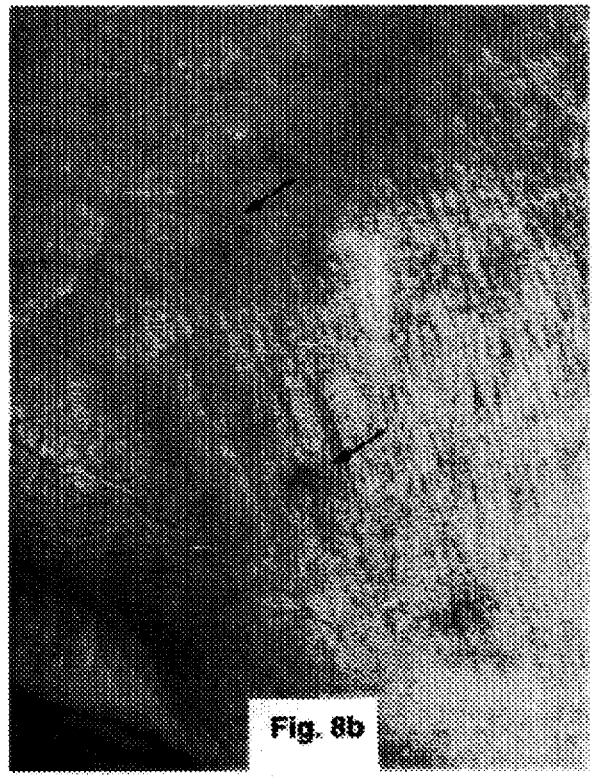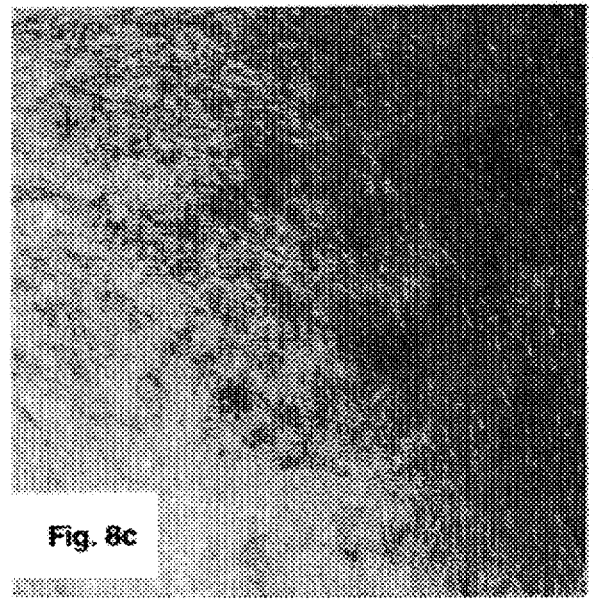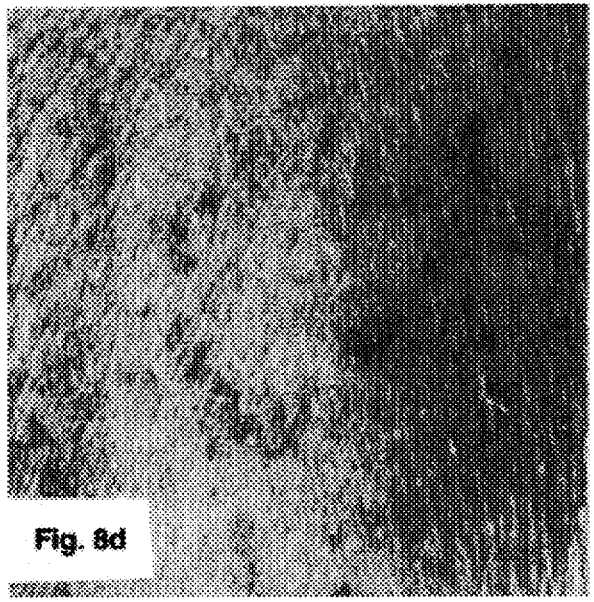

5,792,753

1

COMPOSITIONS COMPRISING HYALURONIC ACID AND PROSTAGLANDIN-SYNTHESIS-INHIBITING DRUGS

This application is a continuation-in-part of Ser. No. 07/675,908, filed Jul. 3, 1991. This application is also a continuation-in-part of Ser. No. 07/838,675, filed Feb. 21, 1992, now U.S. Pat. No. 5,639,738, which is a continuation in part of Ser. No. 07/675,908, filed Jul. 3, 1991.

FIELD OF INVENTION

This invention relates to the treatment of disease and conditions of the skin and exposed tissue. In some embodiments this invention finds application to the treatment of a disease or condition of the skin and exposed tissue including basal cell carcinoma, squamous cell tumours, metastatic cancer of the breast to the skin, primary and metastatic melanoma in the skin, malignancies and tumours in the skin, genital warts (condyloma acuminata), cervical cancer, HPV (Human Papilloma Virus) including HPV (Human Papilloma Virus) on the cervix, psoriasis (both plaque-type psoriasis and nail bed psoriasis), corns on the feet, actinic keratoses lesions, "liver" spots, fungal lesions, and other such types of lesions, and hair loss on the head of a pregnant women.

This invention also relates to compositions and formulations suitable for use in such treatments, the use of such formulations in such treatments, methods of such treatment, and the delivery of drugs for such treatments.

BACKGROUND OF THE INVENTION

Basal cell carcinoma is presently treated by surgery. Each lesion, together with all surrounding and underlying tissue (dermis, epidermis, and subdermis), is cut out. In some instances, surgery, while necessary for the patient's welfare, puts the patient at risk in some other respect (for example, the removal of a lesion on a patient's temple (resection) may jeopardize the patient's health). Squamous cell tumours are also treated the same way as are other forms of cancer in the skin and exposed tissue. Furthermore, other conditions and diseases of the skin and exposed tissue are treated in the same way or in ways that cause discomfort to the patient, for example melanoma, genital warts, cervical cancer, HPV (Human Papilloma Virus).

Actinic keratoses lesion is dealt with similarly. Liquid nitrogen is also used to remove the lesion.

These diseases and conditions are usually found in the epidermis (at least for the most part, extending into the dermis and upwards through the Stratum Corneum).

Hyaluronic acid is a naturally occurring glycosaminoglycan. Its molecular weight may vary from 50,000 daltons upwards, and it forms highly viscous solutions. As regards the actual molecular weight of hyaluronic acid in natural biological contexts, this is still a matter of much uncertainty; when the molecular weight of hyaluronic acid is to be determined, different values are obtained depending on the assay method employed, and on the source, the isolation method etc. The acid occurs in animal tissue, e.g. spinal fluid, ocular fluid, synovial fluid, cockscombs, skin, and also in some streptococci. Various grades of hyaluronic acid have been obtained. A preparation with an allegedly high degree of purity and alleged to be entirely free from side effects, is a non-inflammatory form described in U.S. Pat. No. 4,141,973; this preparation is said to have a molecular weight exceeding 750,000 dalton, preferably exceeding 1,200,000

2 dalton and is suggested for therapeutic use in various articular conditions. Applicants believe that hyaluronic acid claimed in this patent is sold under the trade mark Healon.

U.S. Pat. No. 4,801,619 relates to hyaluronic acid, having a molecular weight of about $3 \times 10^6$ dalton or more, administered intra-articularly which is prone to decrease the proteoglycan content of synovial fluid to almost normal levels. According to this patent, this indicates a positive effect on the proteoglycan metabolism of a joint. According to the patent, this is applicable both to inflammatory conditions and to degeneration caused by treatment with symptomatics, such as corticosteroid preparations. It is thus clear that a sufficiently high molecular weight of the hyaluronic acid is alleged to counteract side effects that might be caused by corticosteroids or other symptomatics producing similar effects. When corticosteroids are applied, the amount of hyaluronic acid in the synovial cavity will, according to the patent, increase substantially and, according to the inventors, their hyaluronic acid preparations have a very positive effect on such clinical symptoms as pain, swelling, and lameness.

The patent states that the objectives of the invention are attained by intra-articular administration (injection) of an effective amount of hyaluronic acid with a mean molecular weight exceeding $3 \times 10^6$ dalton, preferably exceeding $4 \times 10^6$ dalton; usually the molecular weight will not exceed $7 \times 10^6$ dalton. The dosage of hyaluronic acid administered is stated to be preferably within the range of 5 mg–80 mg. The amount of solution given at each administration is generally less than 60 ml, e.g. less than 20 ml. of an aqueous solution of the acid or its salt. It is convenient to administer the acid dissolved in water (<2% w/w, buffered to physiological pH), for instance in the form of a water-soluble sodium salt. The exact amount will depend on the particular joint to be treated.

The Merck Index Specifies that Hyaluronic Acid has a Molecular Weight within the range of 50,000 to $8 \times 10^6$ depending on source, methods of preparation, and methods of determination. The Merck Publication teaches hyaluronic acid as a surgical aid (ophthalmological).

U.S. Pat. No. 4,808,576 purports to teach that hyaluronic acid, an agent well known for reducing the sequelae of trauma in mammalian joint tissue when injected directly into the traumatized joint tissue, will be carried to such traumatized tissue by the mammal's natural processes if applied at a site remote from the traumatized tissue. Thus, hyaluronic acid in any therapeutically acceptable form can, according to the Patent, be administered by the typical remote routes including intravenous, intramuscular, subcutaneous, and topical.

This, the patent alleges, makes the utilization of hyaluronic acid much more convenient and attractive. For instance, the treatment of arthritis in horse or human joints with hyaluronic acid, according to the patent, no longer requires more difficult intra-articular injections.

U.S. Pat. No. 4,725,585 relates to a method of enhancing or regulating the host defence of a mammal by administering to a mammal a therapeutically effective amount of hyaluronic acid.

At column 1, lines 43–46, the patent provides that the invention was based on the unexpected discovery that administration of hyaluronic acid to mammals results in a considerable increase in the defence.

The hyaluronic acid employed in the patent was Healon (t.m) provided by Pharmacia AB, Uppsala, Sweden (Pharmacia AB is also entitled to the benefit of U.S. Pat. No.

4,141,973). The patent provides at column 4, line 19 that because a patient's infections had been hard to treat, instead of just hyaluronic acid being administered to the patient to increase the patient's defence, the patient was given hyaluronic acid and an antibiotic. While one reading the patent may conclude that the antibiotic was given in combination with hyaluronic acid, in fact because the hyaluronic acid was administered subcutaneously and because the patient was a heart patient, one skilled in the art would understand that any antibiotic administered, while possibly administered simultaneously with the administration of the hyaluronic acid, was definitely administered separately intravenously (probably) or intramuscularly (less probably). Thus, the hyaluronic acid administered, according to the teachings of this patent, was administered in order to prevent possible development of infections (increase the host's defence) and not for any other reason.

U.S. Pat. No. 4,636,524 discloses cross-linked gels of hyaluronic acid, alone and mixed with other hydrophilic polymers and containing various substances or covalently bonded low molecular weight substances and processes for preparing them. These products are alleged to be useful in numerous applications including cosmetic formulations and as drug delivery systems.

The patent further states that as hyaluronic acid is known to be a biologically tolerable polymer in the sense that it does not cause any immune or other kind of response when introduced into a human body, the cross-linked hyaluronic acid gels can be used for various medical applications. The cross-linked gels modified with other polymers or low molecular weight substances, it is alleged, can be used as drug delivery devices. For example, the inventors are alleged to have found that heparin introduced in a cross-linked hyaluronic acid gel retained its antithrombogenic activity.

The inventors also allege that they have also found that cross-linked gels of hyaluronic acid can slow down the release of a low molecular weight substance dispersed therein but not covalently attached to the gel macromolecular matrix.

U.S. Pat. No. 4,736,024 purports to teach new medicaments for topical use containing:

(i) an active pharmacological substance or a mixture of pharmacological substances, either active or suitable for topical administration and (ii) a topical vehicle which comprises hyaluronic acid or a molecular fraction of hyaluronic acid or a salt of the same with an alkaline metal, an alkaline earth metal, magnesium, aluminium, ammonium, or a pharmacological substance optionally together with additional conventional excipients for pharmaceutical preparations for topical use.

Applicants are also aware of published Japanese Patent Document 61000017, dated 86/01/06, whose English abstract of disclosure states that the Japanese Patent Document relates to the use of hyaluronic acid or cross-linked hyaluronic acid or their salts as the active ingredient for inhibiting carcinoma metastasis.

According to the purported abstract of the patent, more that 1.0% of hyaluronic acid is dissolved in alkaline aq. soln. and pref. more than 50% of $H_2O$ sol. org. solvent. eq. alcohol, acetone, dioxane, against total soln. is added. Preferably the pH is 12–14. Then a multifunctional epoxy cpd. is added and reacted at 10–60 deg. C, pref. at 20–40- deg. C for 24 hrs. Cross-linking ratio of crosslinked hyaluronic acid or its salt is regulated by changing mol ratio of hyaluronic acid or its salt and multifunctional epoxy cpd. Pref. hyaluronic acid used has intrinsic viscosity 0.2–30, m.w. 4000–2000000. The hyaluronic acid is allegedly used in several dosage forms. The clinical dose for an adult is alleged to be normally, as hyaluronic acid or cross-linked hyaluronic acid, 25 mg–5 g/day (p.o.) and 10 mg–2.5 g/l dose (inj). The abstract alleges that the advantage is that the hyaluronic acid has no side effects as may other anti-cancer drugs and has an analgesic and a tissue restoration effect.

European Patent Application 0295092 purports to teach a vehicle together with fragments of hyaluronic acid for delivering of the fragments of hyaluronic acid into the skin to reach the dermal layer of the skin to increase the development of blood vessels for stimulating hair growth or regrowth. The preferred fragments of hyaluronic acid are polysaccharides containing from 7 to 25 monosaccharide units. The patent provides that it is apparent that the larger the fragments of hyaluronic acid, the greater the difficulty there is in delivering the fragments to the dermal layer of the skin, unless there is also present in the composition a means for enhancing the activity of said fragments.

The combination may thus include a means for enhancing the activity of the fragments of hyaluronic acid, especially to improve their penetration through the skin following topical application. Some activity enhancers, it is alleged, also function as vehicles for the fragments of the hyaluronic acid.

Some activity enhancers are also alleged to possess the ability to stimulate or increase hair growth. Minoxidil is asserted among others to be such an activity enhancer. Thus both the fragments of hyaluronic acid and minoxidil are alleged to stimulate hair growth both delivered by a vehicle.

European Patent Application 0179442 asserts that where free radicals are formed in considerable quantities, hyaluronic acid is broken down or degraded before the hyaluronic acid has given the desired effect.

Canadian Letters Patent 1,240,929 teaches the combination of chondroitin sulfate compound and a hyaluronate to protect both human and animal cell layers and tissue subject to exposure to trauma.

European Patent Application 0208623 purports to teach hyaluronic acid as an augmentation of the activity of certain proteases. It also purports to teach the use of hyaluronic acids for treating connective tissue diseases, including malignant tumours and cardiovascular disorders.

European Patent Application 270317 purports to teach the combination of an antiviral agent lacking inhibitory action and a compound [for example, hyaluronic acid] possessing cell fusion inhibitory activity and/or virus-adsorption inhibitory activity for treating disease carried by a virus.

U.S. Pat. No. 4,840,941 purports to teach the use of an effective amount of hyaluronic acid as the active agent for the treatment of retroviruses in association with a pharmaceutically acceptable carrier, diluent, or excipient.

U.S. Pat. No. 4851,521 and European Patent Application 0265116 both describe hyaluronic acid fractions, the making thereof and cross-linked esters of hyaluronic. U.S. Pat. No. 4,851,521 describes esters of hyaluronic acid incorporated into pharmaceutical preparations as the active ingredient and as vehicle for ophthamological medicines for topical use (See column 11, lines 35 to 42; and column 12, lines 62 to column 13, line 3) and in suppositories for a systemic effect due to the effect of transcutaneous absorption, such as in suppositories.

The patent provides at column 13, lines 5 to 31:

"The vehicling action of the hyaluronic esters also applies to associated medicaments of the type mentioned above in which the active substance acts not only topically or by nasal or rectal absorption, for example by nasal sprays or preparations for inhalation for the oral cavity or the pharynx, but also by oral or parenteral route, for example by intramusclar, subcutaneous or intravenous route, as it favors absorption of the drug into the application site. The new medicaments can therefore be applied, apart from in the fields already mentioned, in practically all sectors of medicine, such as internal medicine, for example in pathologies of the cardiovascular system, in infections of the respiratory system, the digestive system, the renal system, in diseases of an endocrinological nature, in oncology, in psychiatry etc., and may also be classified therefore from the point of view of their specific action, being perhaps anesthetics, analgesics, anti-inflammatories, wound healers, antimicrobics, adrenergic agonists and antagonists, cytostatics, antirheumatics, antihypertensives, diuretics, sexual hormones, immunostimulants and immunosuppressants, for example, one of the drugs having the activity already described for the therapeutically active alcohols to be used as esterifying component according to the present invention, or for the therapeutically active bases used for the salification of the free carboxylic groups."

There have been extensive studies to determine the defect in immune function that allows a tumour cell to develop. It was postulated that the immune system's major role was that of immunological surveillance to destroy abnormal cells. The concept of surveillance, while somewhat simplistic, remains an accepted concept for the elaborate mechanism of immune recognition and function that is present in the higher species—mammals.

It has then been postulated that tumours develop because of local or generalized immune suppression. However, if general immune suppression occurs, it is only certain types of neoplastic disorders that develop, mainly those of the lympho-reticular system. This observation is generally correct and represents a major challenge to the immune surveillance theory unless a specific reason can be shown as to why the individual cancer cell can develop plus individually evade the immune system.

It was demonstrated experimentally in 1974 that defects of macrophage function may exist in neoplastic disease.

The initial experiments found suppressor cells to be part of the immune system; these were either of the T-cell type of the macrophage cell system. There was presence demonstrated in neoplasia, chronic bacterial infection, recovery from massive injury and chronic fungal infection.

There has been repeated demonstration in experimental animals that the macrophage cell function is altered in neoplastic disease. The macrophages in the animal's systems appeared "blocked" in their function. Generally when removed from the in vivo situation, washed in saline and cultured, they perform normally. This block has been shown to be related to the excessive production of prostaglandin by neoplastic tissue or by the macrophage itself. Similarly, the N.K. cells (which are said to be primitive or immature macrophages and which may be involved in cancer defence) are also blocked.

In the basic research efforts in the latter '70s and the early '80's, there existed considerable confusion as to what role immunotherapy should take in cancer. Activation or "hyping" of macrophages was thought to be important. However, in an examination of peritoneal macrophages obtained from patients with neoplastic disease, there was definite evidence that these macrophages were already activated yet were co-existing with cancer cells and not causing their destruction.

It has recently been shown that the malfunction of macrophages or the putitive block is due to excessive prostaglandin and that this can be altered in tissue culture by corticosteroids, ASA, and the non-steroidal anti-inflammatory drugs, i.e. indomethacin and naproxen (Naprosyn™). Again, it was repeatedly demonstrated that in animal tumours these substances could alter the response to neoplastic cells and that various combinations of these substances employed with immune enhancing agents could produce very credible success in eliminating experimental tumours. Researchers combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastro-intestinal, neurological, and other areas. Thus, the basis of the present approach is that, under general circumstances, with the use of these agents in human disease in sufficient amounts, the drug will penetrate to any pathological tissue to alter therapeutically local prostaglandin production. While intravenous preparations of Indomethacin (and now of other agents) exist, using these drugs alone produces prohibitive side effects in human subjects. Therefore, only insufficient amounts can be brought into the body to effect more than occasional responses in neoplasm.

However, the majority of the evidence is present to indicate and therefore, it can be postulated that the basis for neoplastic development and how the initial cell "sneaks by" the immune surveillance mechanism relates to its production of prostaglandin. One need postulate only one mutation to alter the amount of prostaglandin synthesis produced by cells when they become "malignant" to establish a mechanism of blocking out the initial cell in any immune reaction, i.e. the macrophage. It therefore became essential to develop a combination of NSAIDs for clinical use to produce a major improvement in response in neoplastic disease and other conditions where excessive prostaglandin synthesis represents the basis of the pathogenesis of this disease state, i.e. arthritis and various others of the so-called connective tissue inflammatory disorders and/or auto-aggressive diseases.

U.S. Pat. No. 4,711,780 teaches a pharmaceutical composition comprising Vitamin C, a zinc salt, and a sulfur amino acid for treating surface epithelium for epithelium regeneration. Hyaluronic acid may be added for applications in the reproductive tract to block the passage of toxins into the blood system.

U.S. Pat. No. 4,937,254 (Ethicon) teaches combinations of hyaluronic acid and salts thereof with NSAIDS for the prevention of adhesions after surgery.

Because of the side effects of the use of non-steroidal anti-inflammatory drugs (major toxicity in terms of gastrointestinal, neurological, and other areas), use thereof should also be restricted (if possible) to the area of use without delivery to other areas which are not in need of treatment. Thus, if useful amounts of the non-steroidal anti-inflammatory drugs or for that matter any drugs could be delivered to a site in need thereof without carriage of substantial amounts away from the site to be treated, thereby accumulating an amount of the drug at the site to be treated for a prolonged period of time, then the use of the drug for example a non-steroidal anti-inflammatory drug at a site may have many other useful applications.

SUMMARY OF THE INVENTION

Applicants have now developed compositions, (combinations and formulations) which are topically applied to the skin and/or exposed tissue of a human and which are quickly transported in dosage amounts percutaneously (intracutaneously) at a site in need of treatment, (site of pathology and/or trauma) best targeting the epidermis and subsequently remaining (accumulating) at the site for a prolonged period of time. The compositions subsequently clear through the lymphatics thereby bringing dosage amounts of the compositions to the lymphatics for the treatment of disease and conditions in the lymphatics.

These compositions, (combinations and formulations) employ, combine, or incorporate (as the case may be) a plurality of effective non-toxic dosage amounts, each dosage amount comprising an effective non-toxic dosage amount of a drug for example a drug which inhibits prostaglandin synthesis for example an NSAID and an effective non-toxic dosage amount of a form of hyaluronic acid (preferably hyaluronic acid or salt thereof) for the transport of the drug to the site of the pathology and/or trauma. Suitable dosage amounts of the composition may be removed from a container (for example a tube or jar) and administered (for example, applied).

Thus according to one aspect of the invention these pharmaceutical compositions (combinations and formulations) comprise a plurality of effective non-toxic dosage amounts for administration to the skin and/or exposed tissue of a human in need of treatment, each such dosage amount comprising a therapeutically effective non-toxic (to the patient) dosage amount of a drug to treat a disease and/or condition for example a drug which inhibits prostaglandin synthesis, preferably being a non-steroidal anti-inflammatory drug (NSAID), for example, diclofenac, indomethacin, naproxen, and (±) tromethamine salt of ketorolac (sold under the trademark Toradol™) and an effective non-toxic dosage amount (for example in excess of 5 mg per cm² (square centimeter) of skin or exposed tissue to which the dosage amount of the composition is to be applied) of hyaluronic acid and/or salts thereof (for example the sodium salt) and/or homologues, analogues, derivatives, complexes, esters, fragments, and/or sub units of hyaluronic acid (preferably hyaluronic acid and/or salts thereof) to transport (to facilitate or cause the transport of) the drug to the site of the pathology and/or trauma of the disease or condition. These compositions may be applied topically to treat diseases and conditions of the skin and/or exposed tissue at the site of the trauma and/or pathology, (for example, basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, malignancies and/or tumours in the skin, genital warts (condyloma acuminata), cervical cancer, and HPV (Human Papilloma Virus) including HPV of the cervix, psoriasis (both plaque-type psoriasis and nail bed psoriasis), corns on the feet and hair loss on the head of pregnant women). The results of the treatment with suitable dosage amounts taken from these compositions (combinations and formulations) have been in some instances quite dramatic—difficult situations have been successfully treated and resolved.

Furthermore, application of the dosage amounts of the compositions, combinations and formulations are, systemic independent (there is a lack of a blood level of the drug for example NSAID), are quick to penetrate into the skin to the site of the trauma and/or pathology because the effective dosage amount of the form of hyaluronic acid transports (facilitates or causes the transport of) the drug (for example NSAID) particularly to the epidermis where the composition, combination or formulation accumulates and remains for prolonged periods. The compositions subsequently clear through the lymphatics and are available for the treatment of disease and conditions of the lymphatics.

In this regard effective amounts of the form of hyaluronic acid exceeds in the order of about 5 mg per square cm. (cm²) of the area of for example the skin and/or exposed tissue to which the dosage amounts of the composition is to be applied.

Thus, according to another aspect of the invention, Applicants have provided topically applicable percutaneous (intracutaneous) penetrating (best targeting the epidermis) systemic independent acting (not acting essentially through the blood) pharmaceutical compositions (combinations and formulations) comprising a plurality of dosage amounts each comprising, together with pharmaceutical excipients suitable for topical application, a therapeutically effective (to treat and to assist to resolve diseases and conditions of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, malignancies and/or tumours in the skin primary and metastatic melanoma in the skin, genital warts (condyloma acuminata), cervical cancer, and HPV (Human Papilloma Virus) including HPV of the cervix, psoriasis (both plaque-type psoriasis and nail bed psoriasis), corns on the feet and hair loss on the head of pregnant women), non-toxic (to the patient) dosage amount of a drug for example which inhibits prostaglandin synthesis, preferably a non-steroidal anti-inflammatory drug (NSAID), for example, diclofenac, indomethacin, naproxen, and (±) tromethamine salt of ketorolac (sold under the trademark Toradol™) and an effective non-toxic amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) to transport (facilitate or cause the transport of) the drug (for example NSAID's) rapidly to the site in the skin (for example epidermis) and/or exposed tissue of the disease or condition into the tissue to remain there for a prolonged period of time to assist to treat and assist to resolve the disease or condition for example by blocking prostaglandin synthesis.

Effective dosage amounts of the form of hyaluronic acid to facilitate or cause the transport of the drug into the skin and/or exposed tissue by the form of hyaluronic acid exceeds about 5 mg.–10 mg. in the dosage amount administered (applied and rubbed in) for each 1 cm² of skin and/or exposed tissue area of the disease or condition (for example basal cell carcinoma) to which the dosage amount is applied. The dosage amount applicable will depend upon the surface area of the skin and/or exposed tissue in which the condition or disease exists. Thus if the disease or condition occupies about 0.5 cm², in excess of about 2½ mg of the form of hyaluronic acid would be used (applied and rubbed in). In the same way if the area is 2 cm², the amount of the form of hyaluronic acid preferably exceeds about 10–20 mg of the dosage amount of the formulation or composition applied. Preferred forms of the hyaluronic acid (for example hyaluronic acid and the sodium salt thereof) have molecular weights less than about 750,000 daltons (for example about 150,000 to about 225,000 daltons) to transport the medicine in the skin and/or exposed tissue. While higher molecular weights of the hyaluronic acid and forms thereof may be used to penetrate the skin and/or exposed tissue and transport the medicines or drugs, where the molecular weight of the hyaluronic acid chosen for use is very large, it is preferred that the form of hyaluronic acid is autoclaved, to break down the hyaluronic acid to fragments of lesser molecular weight or if feasible diluted to permit administration and ensure no coagulation on or in the skin. Where the molecular weight of the form of hyaluronic acid being employed is large, the concentration of the form of the hyaluronic acid in the composition may for example be reduced (for example to less than about 3%) dependent on the molecular weight.

The blockage of prostaglandin synthesis by the transported drug (for example NSAIDS) then unblocks the macrophages and permits the macrophages of the patient proximate the lesion (for example, the basal cell carcinoma) to destroy the lesion or condition. Treatment by dosage amounts of the composition (formulation and/or combination) eliminates the condition without recurrence, even where the lesion has recurred a number of times after unsuccessful treatments according to the prior art.

Other non-steroidal anti-inflammatory drugs (NSAIDS) may be used such as other propionic acid derivatives, Ibuprofen, acetylsalicylic acid, piroxicam and flunixin.

When dosage amounts of such compositions, combinations and formulations are applied to the site of the disease or condition for example the basal cell carcinoma of the patient suffering from the basal cell carcinoma, over a period of time (for example, for a period of 2-4 weeks 3 times daily) the basal cell carcinoma is completely resolved and disappears.

Thus according to another aspect of the invention there is provided a pharmaceutical composition from which dosage amounts may be taken for application to the skin and/or exposed tissue, the pharmaceutical composition comprising in a form for application to a human a plurality of dosage amounts of medicine and/or therapeutic agent to treat a disease or condition in a human and a plurality of dosage amounts of hyaluronic acid and/or salts and/or homologues, analogues, derivatives, complexes, esters, fragments, and/or sub-units of hyaluronic acid such that when dosage amounts of the pharmaceutical composition are taken from the composition, the amount of the medicine and/or therapeutic agent comprises an effective non-toxic dosage amount of the medicine to treat the disease or condition in the skin and/or exposed tissue in a human and the amount of the form of hyaluronic acid in the dosage amount is present in an effective amount to transport (facilitate or cause the transport of) the medicine and/or therapeutic agent intradermally (percutaneously, intercutaneously, intracutaneously) into the skin (preferably to the epidermis and dermis) and/or exposed tissue of a human to the site of a pathology and/or trauma. The effective amount of the form of hyaluronic acid has a molecular weight and concentration to transport the medicine (drug) and/or therapeutic agent to the site of trauma and/or pathology in the skin and/or exposed tissue. In this regard the preferred amount of the form of hyaluronic acid in each dosage amount exceeds 5 mg./cm$^2$ and preferably the molecular weight is less than about 750,000 daltons, (in one embodiment about 150,000 to about 225,000 daltons) in some embodiments with a concentration of between about 1 and 3%, preferably concentrations of between about 2 to about 3% by weight. Where forms of hyaluronic acid are used having greater molecular weights, they are preferably cleaved and/or diluted to smaller concentrations, to facilitate or cause the transport of the medicine and/or therapeutic agent.

According to another aspect of the invention there is provided a pharmaceutical composition (for example a gel or cream) from which dosage amounts may be taken and applied to the skin to treat a disease or condition in humans, for example as discussed above, the pharmaceutical composition comprising:

(1) a medicinal and/or therapeutic agent suitable for treating a disease or condition in the skin and/or exposed tissue in humans, for example a drug which inhibits prostaglandin synthesis (for example an NSAID); and (2) hyaluronic acid and/or salts thereof and/or homologues, analogues, derivatives, complexes, esters, fragments, and sub-units of hyaluronic acid, in a form suitable for administration to the skin and/or exposed tissue in humans; characterized in that an effective non-toxic dosage amount comprising components (1) and (2) taken and administered from said composition (i) is available in the skin and/or exposed tissue upon administration to treat said disease or condition in humans by penetration at the site to be treated to the site of trauma and/or pathology, and (ii) comprises an effective non-toxic dosage amount of component (2) effective to transport (facilitate or cause the transport of) component (1) immediately upon administration percutaneously into the skin (preferably the epidermis) to the site to be treated for example the site of trauma and/or pathology where it remains for a prolonged time, accumulating there and from which it is discharged via the lymphatic system.

Therefore according to another aspect of the invention a pharmaceutical composition is provided comprising:

(1) a medicinal and/or therapeutic agent which for example inhibits prostaglandin synthesis in a therapeutically effective amount to treat a disease or condition of the skin and/or exposed tissue;

and (2) hyaluronic acid and/or salts thereof and/or homologues, analogues, derivatives, complexes, esters, fragments, and subunits of hyaluronic acid, characterized in that said composition (a) is in a dosage form (for example a gel or cream) which is suitable for administration to the skin and/or exposed tissue;

and (b) is in such an amount and in such form that (i) component (1) is in an effective dosage amount to treat said disease or condition by penetration at the site of the skin and/or exposed tissue to be treated for example the basal cell carcinoma and other lesions; and (ii) component (2) is immediately available to transport (facilitate or cause the transport of) component (1) to the site of trauma and/or pathology to be treated, percutaneously into the skin (or exposed tissue) where the composition resides and accumulates for a prolonged period, and which component (2) is in an effective non-toxic dosage amount to transport (facilitate or cause the transport of) component (1) upon administration, percutaneously into the skin or exposed tissue to the site of the trauma and/or pathology. Preferably the form of hyaluronic acid in the composition comprises hyaluronic acid and/or salts thereof. An effective amount of the form of hyaluronic acid exceeds about 5–10 mg per square centimeter (cm$^2$) of skin and/or exposed tissue to which it is to be applied.

According to another aspect of the invention there is provided the use of:

(1) a medicinal and/or therapeutic agent for example which inhibits prostaglandin synthesis, and (2) hyaluronic acid and/or salts thereof and/or homologues, analogues, derivatives, complexes, esters, fragments, and subunits of hyaluronic acid, in the manufacture of a pharmaceutical composition for treating a disease or a condition (for example those discussed above) of the skin and/or exposed tissue in a therapy wherein dosage amounts taken from the composition each comprise:

(1) a therapeutically effective amount of said medicinal and/or therapeutic agent and (2) a therapeutically effective amount of the hyaluronic acid and/or salts thereof and/or homologues, analogues, derivatives, complexes, esters, fragments, and sub-units of hyaluronic acid, the pharmaceutical composition being characterized in that for each dosage amount taken from the pharmaceutical composition, the amount of component (2) is immediately available to transport component (1) percutaneously to the site of trauma and/or pathology for example into the epidermis where the composition accumulates and remains for a prolonged period, at the site of the skin or exposed tissue to be treated, and component (2) is in an effective non-toxic amount to transport (facilitate or cause the transport of) component (1) into the skin or exposed tissue (for example into the epidermis). Preferably component (2) is hyaluronic acid and/or salts thereof and preferably the dosage amount of component (2) in the amount of the composition taken from the composition (to be taken from the composition) and applied to the skin or exposed tissue is a dose amount greater than about 5–10 mg per cm$^2$ of skin and/or exposed tissue to which the dosage amount is to be applied.

The pharmaceutical composition will normally include pharmaceutically compatible excipients to provide a form for ease of administration to the skin and/or exposed tissue for transport into the epidermis. For example a suitable dosage amount of a gel may be squeezed from a tube as a ribbon of gel "X" cm long (which dosage amount (in the form of the ribbon "X" cm long) contains the effective non-toxic dosage amounts of the drug and form of hyaluronic acid. Or a dosage amount of cream packaged in a jar may be scooped from the jar by a measuring device or by "two fingers" in a suitable amount (for example in a spoon containing a premeasured volume or an amount about half the "length of the fingers"). Each of the dosage amounts selected comprises the effective amounts of drug (for example NSAID) and effective amount of the form of hyaluronic acid (for example hyaluronic acid and/or salts thereof). In this way the patient may "squeeze" or "scoop" or "what have you" the appropriate dosage amount and apply (rub in) the dosage amount onto the skin and/or exposed tissue for transport into the epidermis.

Thus, according to another aspect of the invention, a method of treating a disease and/or condition of the skin or exposed tissue, for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, malignancies and/or tumours in the skin, genital warts (condyloma acuminata), cervical cancer, HPV (Human Papilloma Virus) including HPV of the cervix, psoriasis (both plaque-type psoriasis and nail bed psoriasis), corns on the feet and hair loss on the head of pregnant women, in a human is provided comprising administering topically to human skin and/or exposed tissue an effective non-toxic dosage amount of a composition comprising, together with pharmaceutical excipients suitable for topical application to the skin and/or exposed tissue, for example in the form of a gel or cream (to give the composition definition and form so that specific dosage amounts are easily selected or taken for administration (for example squeezed from a tube or scooped from a jar and rubbed into the skin or exposed tissue), a therapeutically effective (to treat and to assist to resolve the disease or condition for example basal cell carcinoma or other lesion), non-toxic (to the patient) dosage amount of a drug for example which inhibits prostaglandin synthesis, for example a non-steroidal anti-inflammatory drug (NSAID), for example, diclofenac, indomethacin, naproxen, and (±) tromethamine salt of ketorolac (sold under the trademark Toradol™) and an effective non-toxic dosage amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) to transport (facilitate or cause the transport of) the drug (for example NSAID) into the skin or exposed tissue to the site of the disease or condition to be treated percutaneously, (to the site of trauma and/or pathology), for example into the epidermis, where the form of hyaluronic acid and medicine accumulates and remains for a prolonged period of time thereby for example blocking prostaglandin synthesis in the skin or exposed tissue. The form of hyaluronic acid is then cleared through the lymphatics (lymphatics system).

Thus, according to another aspect of the invention, the treatment may employ the use of the composition, formulation or combination for the treatment of the diseases and conditions aforesaid as for example by applying dosage amounts of the composition, formulation or combination a number of times daily (for example, 3 times daily) for a period of time, for example, 2–4 weeks to clear the disease, lesion or condition. Each dosage amount applied will depend upon the size of the lesion or condition on the skin or exposed tissue. For example, a suitable dosage amount may include 5–10 mg. of the form of hyaluronic acid per 1 cm$^2$ skin area or exposed tissue area.

One such formulation may comprise 3% (by weight) diclofenac in a 2½ % (by weight) hyaluronic acid (sodium hyaluronate—molecular weight 661,600) gel formulation, with the excipients being glycerine (5%), benzyl alcohol (3%) (acting in part as a solubilizer and preservative), and sterile water (the balance) in a 50 gm. tube of the composition (a plurality of dosage amounts) whose tube O.D. (outer diameter) of the opening through which the gel formulation is discharged from the tube is 8 mm and whose I.D. (inner diameter) of the opening is 4 mm. Therefore a ribbon 2–3 cm in length, squeezed from a tube gives about 5 mg-7½ mg of hyaluronic acid for application to a skin or exposed tissue surface area of 1-1½ cm$^2$ with an effective dosage amount of diclofenac. While greater amounts squeezed from the tube, may be applied, the application of substantial excessive dosage amounts to the skin and/or exposed tissue may saturate the skin or exposed tissue and thus the epidermis. (There is therefore no more room for the composition to pass between the cells and therefore further applications at that time will not provide additional benefit). Where pain relief is also required additional dosage amounts, for example in excess of about 10 mg. of the hyaluronic acid taken from the same pharmaceutical composition applied per/cm$^2$ of surface area of the skin or exposed tissue may be required to be applied.

Another formulation may comprise 3% (by weight) diclofenac in a 2½ % (by weight) hyaluronic acid (sodium hyaluronate—molecular weight 679,000) gel formulation (also in a tube) with excipients being benzyl alcohol (1%) (a preservative), methoxypolyethylene glycol 350 (20% by weight) (a solubilizer), and sterile water (the balance).

While the above compositions, combinations and formulations are proposed, provided there is sufficient amounts of the form of the hyaluronic acid (for example, sodium hyaluronate) in the dosage amounts applied to the skin and/or exposed tissue to facilitate or cause the percutaneous (intracutaneous) transport of the drug for example which inhibits prostaglandin synthesis, preferably an NSAID (for example, diclofenac) to block prostaglandin synthesis, then the formulations may be of any suitable form, for example, a 1% lotion of hyaluronic acid with NSAID, or a cream or gel or any other suitable form.

Therefore according to another aspect of the invention, there is provided containers (for example tubes and jars) containing compositions comprising a plurality of dosage amounts of the drug and form of hyaluronic acid, each dosage amount comprising an effective non-toxic dosage amount of the drug and an effective non-toxic dosage amount of the form of hyaluronic acid (preferably sodium hyaluronate having molecular weight less than about 750,000 daltons) to transport the drug into the skin and/or exposed tissue. In some embodiments, means are provided to assist the removal from the container of an effective dosage amount of the composition in the container for use to apply to the skin or exposed tissue at the site of trauma and/or pathology to treat the disease and/or condition (for example mouth opening of a tube to control the amount discharged from the tube).

Furthermore, because there is little concern with respect to the toxicity or adverse effects of the use of, for example, the NSAIDs with the hyaluronic acid in the compositions of this invention the NSAID may be combined as needed (after solubilizing (if required) of the NSAID in a suitable solubilizer) with the form of the hyaluronic acid.

Therefore according to another aspect of the invention, percutaneous (intercutanous) delivery of a therapeutically effective dosage amount of a drug (in a composition, combination or formulation) and which drug for example inhibits prostaglandin synthesis, preferably being a non-steroidal drug (NSAID) is provided. In this regard the drug is transported to the site of, on, or in the skin and/or exposed tissue of trauma and/or pathology to treat the disease or condition for example the basal cell carcinoma or actinic keratoses lesion in a mammal (human). The delivery may comprise topically administering (to the skin or exposed tissue site of for example the basal cell carcinoma or other lesion) a therapeutically effective non-toxic (to the patient) dosage amount of a composition comprising a drug for example which inhibits prostaglandin synthesis, preferably an NSAID (non-steroidal anti-inflammatory drug), for example, diclofenac, indomethacin, naproxen, and (±) tromethamine salt of ketorolac (sold under the trademark Toradol™), and an effective non-toxic amount of hyaluronic acid and/or salts thereof and/or homologues, analogues, derivatives, complexes, esters, fragments, and sub-units of hyaluronic acid, preferably hyaluronic acid and salts thereof, sufficient to transport, (facilitate or cause the transport of), the drug for example NSAID percutaneously (to for example the epidermis) to the site of the trauma and/or pathology in for example the epidermis, for example the basal cell carcinoma (or other lesion), to be treated for example to block the synthesis of prostaglandins.

Delivery may be also accomplished by the same amount of the form of hyaluronic acid, of other drugs percutaneously (intercutaneously) to the skin and exposed tissue by application and rubbing in of an effective non-toxic dosage amount of the formulation or composition comprising an effective non-toxic dosage amount of the drug and an effective non-toxic dosage amount of the form of hyaluronic acid for the transport of the drug percutaneously into the skin or exposed tissue to the epidermis where the dosage amount of the composition is accumulated and remains for a prolonged period of time before the form of hyaluronic acid is cleared through the lymphatics. In this regard the drug may be novantrone (an anti-cancer drug) for administration to a tumour or malignancy in the skin. The novantrone may comprise 10 mg in the dosage amount of the composition and the form of hyaluronic acid may be in excess of about 5 mg of sodium hyaluronic per $cm^2$ of the skin or exposed tissue (about 2.5% of the composition) for the percutaneous transport of the novantrone.

Thus, according to another aspect of the invention, use of a composition, combination or formulation is provided to treat a disease or condition for example basal cell carcinoma (or other lesion), by the application of the composition, combination or formulation, the amount of the composition, combination and formulation administered comprising together with pharmaceutical excipients suitable for topical application, a therapeutically effective (to treat and assist to resolve a disease or condition for example, basal cell carcinoma), non-toxic (to the patient) amount of a drug for example which inhibits prostaglandin synthesis preferably a non-steroidal anti-inflammatory drug (NSAID), for example, diclofenac, indomethacin, naproxen, and (±) tromethamine salt of ketorolac (sold under the trademark Toradol™) administered together with, or carried in, an effective dosage amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) effective to transport the drug for example the NSAID (to facilitate or cause the transport of the drug for example NSAID) percutaneously into the skin especially the epidermis at the site of the disease or condition for example basal cell carcinoma (or other lesion) to be treated, thereby, if an NSAID, blocking prostaglandin synthesis to enable the macrophages (and N.K. cells) to resolve the disease or condition for example basal cell carcinoma or other lesion.

Applicants postulate that the hyaluronic acid and/or salts thereof and/or the homologues, analogues, derivatives, complexes, esters, fragments, and/or sub units of hyaluronic acid facilitate or cause the transport of the drug for example which blocks prostaglandin synthesis (preferably an NSAID) to the site of prostaglandin synthesis to block prostaglandin synthesis.

Applicants' compositions and dosage amounts of their compositions and the use of their compositions and dosage amounts of their compositions, at the same time, abate pain that the patient is experiencing at the paccinian nerve bundles (superficial nerve bundles) at the site of the trauma and/or pathology on/in the exposed tissue and/or skin.

Thus, according to another aspect of the invention, a method of abating pain in the skin and/or exposed tissue for example suffering a disease or condition (for example those discussed above), and a composition from which dosage amounts may be taken and applied (rubbed in) which is useful for abating such pain are provided, the method comprising administering (rubbing on) an effective dosage amount of the composition to the skin and/or exposed tissue, and the composition comprises a plurality of dosage amounts, each comprising an effective non-toxic dosage amount of an NSAID and an effective non-toxic dosage amount of the hyaluronic acid and/or salts thereof and/or homologues, analogues, derivatives, complexes, esters, fragments, and/or subunits of hyaluronic acid (preferably hyaluronic acid and salts thereof), for example amounts exceeding 10–20 mg. per square cm ($cm^2$) of skin or exposed tissue to which it is applied, for percutaneous transport of the NSAID by the form of hyaluronic acid into the epidermis proximate the paccinian nerve bundles (superficial nerve bundles at the end of the nerves) to abate pain. Thus, according to another aspect of the invention, compositions are provided for use to relieve pain from which dosage amounts of the composition comprising dosage amounts of the NSAID and form of hyaluronic acid are taken.

By way of example and to illustrate the facilitation of the delivery or transport of a chemical to a site in a human, when ethyl alcohol is injected directly into a tumour and sonographic (ultrasound) assessment is made, it is not dispersed throughout the tumour. When the ethyl alcohol to be administered into a tumour is carried by hyaluronic acid and/or salts thereof, sonographic assessment of the tumour demonstrates the dispersion of the ethyl alcohol throughout the tumour.

While Applicants postulate that the hyaluronic acid facilitate or causes the transport and delivery, Applicants' invention may be used as described irrespective of the actual method of operation of the hyaluronic acid and/or salts thereof and/or the homologues, analogues, derivatives, complexes, esters, fragments and sub-units of hyaluronic acid.

The combination of hyaluronic acid and salts thereof and other forms with drugs for example that inhibit prostaglandin synthesis, for example NSAIDs, alters their distribution and performance in the skin and/or exposed tissue particularly the epidermis (the combinations and formulations being systemic independent), and produces an unusual targeting for underperfused skin and/or pathological tissue in the skin (site of trauma and/or pathology). The application may be made as required with the amount depending upon the condition of the skin or exposed tissue.

As a major amount of soluble indomethacin may be incorporated into the formulation, or composition, the indomethacin may be solubilized using n-methyl glucamine at a dilution of 5 mg/ml of n-methyl glucamine (NMG). This substance is then passed through a 22 micron Milipore filter to produce sterility. This material is non-toxic at 16 fold the therapeutic dose in animals (with hyaluronic acid) and for this reason was considered appropriate to be used in human conditions. Thus, Indocid™ solubilized in NMG may be administered with hyaluronic acid topically for percutaneous penetration at, for example, varying doses. The solution of indomethacin and NMG may be mixed with, for example, "LifeCore™" hyaluronic acid in dosage amounts discussed above. This produces an appropriate mixture and can be administered safely.

When the NSAID, for example indomethacin (dissolved in n-methyl glucamine) or other NSAID, is applied topically in an effective dosage amount from a composition or formulation also including the effective dosage amount of the form of hyaluronic acid, no major toxic side effects occur, such as gastro-intestinal distress, neurological abnormalities, depression, etc., even at elevated amounts of indomethacin (if necessary). (This may be in part because of the clearing of the hyaluronic acid through the lymphatic system from the site). In addition, the responses that have been observed are dramatic when the drug for example NSAID (for example diclofenac) is combined with hyaluronic acid, demonstrating clearly that the combination is now "targeting" to the site of pathology or trauma, or pathological tissue. Furthermore, patients using the formulations and combinations of drug (for example NSAID)— hyaluronic acid (sodium hyaluronate) (for example, diclofenac or indomethacin and hyaluronic acid), experience dramatic relief of pain immediately.

Thus, Applicants believe that the use of the NSAID, for example with hyaluronic acid (sodium hyaluronate), deblocks the macrophages (and N.K. cells (Natural Killer Cells) thought to be immature macrophages) by preventing enzymatic production of prostaglandin which blocks macrophage (and N.K. cell) functioning. The hyaluronic acid (and salt and other forms) not only enhances the activity of the drug (NSAID) but also reduces any side effects and toxicity that is associated with the use of the prostaglandin synthesis inhibitors. When effective dosage amounts of compositions, formulations and combinations containing effective dosage amounts of the drugs for example, (NSAIDs (for example, diclofenac)) and effective dosage amounts of, for example, hyaluronic acid or the sodium salt thereof, are applied to for example the tumour lesion (for example basal cell carcinoma) or other condition (for example, actinic keratoses lesion) for a period of time (for example, 3 times daily for 2–4 weeks), the carcinoma and lesions, as the case may be, disappear.

Applicants also postulate that when the combination or formulation is applied to the disease or condition (for example, basal cell carcinoma or actinic keratoses), the hyaluronic acid passes between the cells (in the stratum corneum and epidermis to the dermis depending on amounts) to the areas of trauma and/or pathology deficient in hyaluronic acid (or forms thereof), transporting, taking, drawing, carrying or pulling the NSAID with it to the sites of prostaglandin synthesis, penetrating to inhibit prostaglandin synthesis until the space between the cells is saturated. The NSAID now being proximate the Paccinian nerve bundle (superficial nerve bundles at the end of the nerves) gives pain relief. The macrophages (which had been previously blocked) are unblocked and act to destroy the disease or condition for example basal cell carcinoma, actinic keratoses lesion, or other disease or lesion. Furthermore, the effective non-toxic dosage amount of the composition, combination or formulation, comprising the effective dosage amount of the form of hyaluronic acid and the effective dosage amount of NSAID passing through the stratum corneum to the epidermis and to the dermis (if a sufficient amount of the form of hyaluronic acid is present), passes into the skin, accumulating and staying longer in the skin at the site of the trauma and/or pathology. Therefore, after having had an immediate effect at the site of trauma and/or pathology (for example, relieving pain and acting on the basal cell carcinoma, actinic keratoses and other disease, condition or lesion), the NSAID-hyaluronic acid combination continues to accumulate at the site in need of treatment and thereafter clears through the lymphatic system.

Thus according to another aspect of Applicant's invention, Applicants' compositions, formulations and combinations quickly penetrate on application through the stratum corneum into the epidermis (to the dermis) by the form of hyaluronic acid transporting the NSAID, to the site of trauma and/or pathology where the amounts applied accumulate and remain for a prolonged time for treatment.

Fifteen (15) minutes after application of one of Applicants' formulations, about three times the amount of Applicants' formulation has penetrated into the skin (particularly the epidermis) than formulations and combinations not containing hyaluronic acid or effective dosage amounts of hyaluronic acid, but containing the same drug. Furthermore, the drug and hyaluronic acid accumulate and remain at the site in need of treatment for a longer period of time.

Thus according to another aspect of the invention, non-toxic effective dosage amounts of forms of hyaluronic acid (preferably sodium hyaluronate) and effective non-toxic dosage amounts of a drug may be administered in compositions to sites of trauma or pathology, on/in the skin and/or exposed tissue (for example the epidermis) by the application of the effective non-toxic dosage amount of the composition comprising an effective non-toxic dosage amount of a drug (for example an NSAID) and an effective non-toxic dosage amount of a form of hyaluronic acid (for example sodium hyaluronate) to the skin or exposed tissue whereby the forms hyaluronic acid transport the drug percutaneously to the site of trauma and/or pathology where the composition accumulates and remains for a prolonged period of time thereby retaining the drug at the site of trauma and/or pathology (for example the epidermis) for the treatment of the condition or disease and the reduction of pain.

Thus according to another aspect of the invention, Applicants have provided compositions (formulations and combinations) (including pharmaceutical excipients suitable for topical application) from which effective non-toxic (to the patient) dosage amounts of a drug (for example an NSAID) to treat and to assist to resolve diseases and conditions of the skin and/or exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, malignancies and/or tumours of the skin, gential warts, cervical cancer, and HPV (Human Papilloma Virus) including HPV of the cervix, psoriasis (both plaque-type psoriasis and nail bed psoriasis), corns on the feet and hair loss on the head of pregnant women), and effective non-toxic dosage amounts of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to transport (to facilitate or cause the transport of) the drug, for example NSAID, are taken for application, to a site in the skin (for example epidermis) or exposed tissue having a disease or condition for percutaneous transport into the skin and/or exposed tissue to accumulate and remain there for a prolonged period of time to for example block prostaglandin synthesis. Thus an effective dosage amount of the composition or formulation or combination penetrates quickly into the skin, for example by the hyaluronic acid transporting the NSAID or causing the NSAID to be transported for example to the epidermis of the skin, accumulates there and remains there for a prolonged period of time, thereby accumulating the drug and forms of hyaluronic acid in the skin (particularly the epidermis).

Thus according to another aspect of the invention, a method of accumulating a drug and a form of hyaluronic acid in skin and/or exposed tissue is provided comprising topically administering a therapeutically effective non-toxic dosage amount of a composition comprising pharmaceutical excipients suitable for topical applications, an effective non-toxic (to the patient) dosage amount of a drug for example which inhibits prostaglandin synthesis, preferably a non-steroidal anti-inflammatory drug (NSAID), for example, diclofenac, indomethacin, naproxen, and (±) tromethamine salt of ketorolac (sold under the trademark Toradol™) (to treat and to assist to resolve the disease and conditions of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, malignancies and/or tumours of the skin, primary and metastatic melanoma in the skin, genital warts cervical cancer, and HPV (Human Papilloma Virus) including HPV of the cervix, psoriasis (both plaque-type psoriasis and nail bed psoriasis), corns on the feet and hair loss on the head of pregnant women), and an effective non-toxic dosage amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) effective to transport (to facilitate or cause the transport of) the drug (for example NSAID) percutaneously to the site in the skin (for example epidermis) or exposed tissue of the disease or condition to accumulate and remain there for a prolonged period of time for example to block prostaglandin synthesis.

According to another aspect of the invention, a method of quickly delivering a drug to the skin or exposed tissue, particularly the epidermis, and maintaining the drug therein for a prolonged period of time is provided, the method comprising topically administering (for example rubbing in) an effective non-toxic dosage amount of a composition comprising pharmaceutical excipients suitable for topical application, a therapeutically effective (to treat and assist to resolve the disease and/or condition of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, malignancies and/or tumours of the skin, genital warts, cervical cancer, and HPV (Human Papilloma Virus) including HPV of the cervix, psoriasis (both plaque-type psoriasis and nail bed psoriasis), corns on the feet and hair loss on the head of pregnant women)), non-toxic (to the patient) dosage amount of a drug for example which inhibits prostaglandin synthesis, preferably a non-steroidal anti-inflammatory drug (NSAID), for example, diclofenac, indomethacin, naproxen, and (±) tromethamine salt of ketorolac (sold under the trademark Toradol™) and an effective non-toxic dosage amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to transport (to facilitate or cause the transport of) the drug for example the NSAID percutaneously to the site of the trauma and/or pathology in the skin (for example epidermis) or exposed tissue, for remaining there for a prolonged period of time (for example in the epidermis and dermis) to for example block prostaglandin synthesis. Suitable amounts of the form of hyaluronic acid may comprise in excess of 5 mg. per cm$^2$ in a form which transports the drug (for example molecular weights of the form of hyaluronic acid being less than about 750,000 Daltons or if at substantially greater molecular weights, diluted (to reduce) the concentration or autoclaved or cleaved if required to reduce the size of the molecules.

According to another aspect of the invention, a method of controlling the unloading of a drug from the skin or exposed tissue into the lymphatic system comprises delivering (transporting) an amount of drug into the skin or exposed tissue by an effective non-toxic dosage amount of a form of hyaluronic acid and/or salts thereof and/or homologues, analogues, derivatives, complexes, esters, fragments, and/or sub-units of hyaluronic acid to the skin (epidermis) or exposed tissue to control the unloading of the drug into the lymphatic system (for example by the application of greater than 5 mg./cm$^2$) of the form of hyaluronic acid.

Thus according to another aspect of the invention a composition is provided which when administered to a human by preferably administration to the skin and/or exposed tissue of a human, unloads its contents into the lymphatic system, the composition comprising an effective non-toxic dosage amount of a drug (for example an NSAID or an anti-cancer drug (Novantrone) and an effective non-toxic amount of hyaluronic acid and/or salts thereof and/or homologues, analogues, derivatives, complexes, esters, fragments and/or sub-units of hyaluronic acid (for example at least about 5–10 mg/cm$^2$ of skin or exposed tissue). Thus the composition is made up of a plurality of such dosage forms (for example a cream or lotion or gel).

Thus according to another aspect of the invention, a new composition for treating diseases via the lymphatic system is provided comprising a plurality of effective non-toxic dosage amounts of the composition, each dosage amount comprising hyaluronic acid and/or salts thereof and/or homologues, analogues, derivatives, complexes, esters, fragments and/or sub-units of hyaluronic acid for passing into the lymphatic system and a therapeutic effective amount of medicine for treatment of a disease (which disease may be in the lymphatic system).

According to another aspect of the invention, the composition may be for application to the skin or exposed tissue.

According to another aspect of the invention, a composition is provided from which effective dosage amounts may be taken and administered, each effective dosage amount of the composition comprising an effective non-toxic dosage amount of hyaluronic acid and/or salts thereof and/or homologues, analogues, derivatives, complexes, esters, fragments and/or sub-units for transporting a therapeutically effective non-toxic dosage amount of a medicine and/or therapeutic agent (for example an NSAID) in the composition into the skin and/or exposed tissue when applied thereto to an area of pathology and/or trauma then into the lymphatic system, the dosage amount being essentially systemic independent such that substantial amounts do not enter the blood system prior to clearing (passing) into the lymphatic system. Preferably the amount of the form of hyaluronic acid in each dosage amount administered is greater than about 5–10 mg./cm$^2$ and the molecular weight is less than about 750,000 daltons.

BRIEF DESCRIPTION OF THE FIGURES

The file of this patent contains at least one drawing executed in color. Copies of this patent with color drawings will be provided by the Patent and Trademark Office upon request and payment of the necessary fee.

FIGS. 6a–6d show the response of basal cell carcinoma in an 82 year old male patient to treatment with NSAIDs and HA gel.

FIGS. 8a–8d show the response of basal cell carcinoma in an 86 year old male patient to treatment with NSAIDs and HA gel.

DESCRIPTION OF EMBODIMENTS

Figure 1:
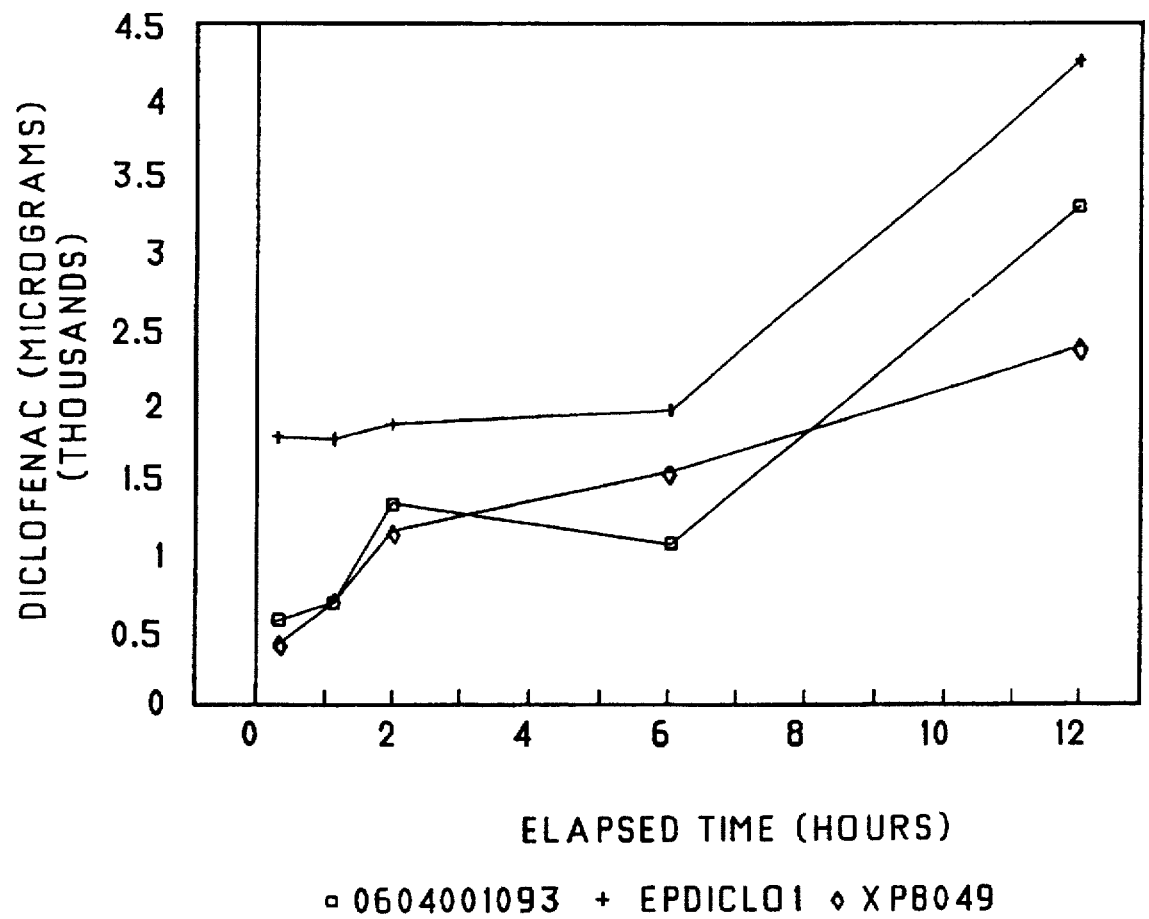
FIG. 1 illustrates the presence of diclofenac in the top skin portion after administration of the several compositions.

We have compared the penetration and retention of one of our combinations (formulations) with a control and Voltarol Emulgel in the skin as follows:

(A) OUR FORMULATION
1% DICLOFENAC IN 3.0% HA GEL 50 g/tube
EPDICLO1
LOT XPB 044 Quantity 1500 ml

| FORMULA | Supplier | Lot | Amount | Percent |
|---|---|---|---|---|
| Sterile Water | Baxter | AW45F1 | 1397 ml | — |
| Glycerin | Life | 1043 | 45 g (36 ml) | 3% |
| Benzyl Alcohol | Caledon | 02517 | 22.5 g (22 ml) | 1.5% |
| Liquid Wax DICDD | Brooks | 191-175 | 45 g | 3% |
| Diclofenac Sodium | Prosintex | 9113003 | 15 g | 1% |
| Sodium Hyaluronate Mol. Wt. 661,600 | Skymart | HG-1103 | 45 g | 3% |

PROCEDURE

Set up stirring apparatus using a 3 liter stainless steel beaker

Add Water, Glycerin, Benzyl Alcohol and Liquid Wax DICDD, stir and mix for 10 minutes Add Diclofenac Sodium and stir for 30 minutes to dissolve Add Sodium Hyaluronate and stir for 90 minutes

FILLED

In a 50 ml aluminum collapsible tube, inside of tube lacquered with a phanolic resin, outside of tube white regular enamel coating;

9 mm white polypropylene screw on cap with pierce tip

| | Gels | Batch No.s |
|---|---|---|
| (B) | Voltarol Emulgel | 060400 10 93 |
| (C) | 1% Diclofenac Gel | XPB049 (Control) |

(C) CONTROL
  1% DICLOFENAC IN CARAPOL GEL, 50 g Jar
  LOT XPB 049 Quantity 100 ml

| FORMULA | Supplier | Lot | Amount | Percent |
|---|---|---|---|---|
| Sterile Water | Baxter | AW45N5 | 93 ml | — |
| Glycerin | BDH | 2579 | 3 g | 3% |
| Benzyl Alcohol | BDH | 23797 | 1.5 g | 1.5% |
| Liquid Wax DICDD | Brooks | L-1424 | 3 g | 3% |
| Diclofenac Sodium | Prosintex | 9113003 | 1 g | 1% |
| Carbopol 934 | A&C Chemicals | 910304 | 1 g | 1% |

PROCEDURE

Set up stirring apparatus using a 400 ml stainless steel beaker

Add Water, Glycerin, Benzyl Alcohol, Liquid Wax DICDD, and stir to mix thoroughly for 10 minutes Add Diclofenac Sodium and stir for 20 minutes to dissolve Very slowly add Carbopol 934, avoid getting lumps
Samples

| Cell | Sample | Quantity of gel applied (mg) |
|---|---|---|
| A | 060400 10 93 | 192 |
| B | 060400 10 93 | 192 |
| C | EPDICLO1* | 192 |
| D | EPDICLO1* | 192 |
| E | XPB049 | 192 |
| F | XPB049 | 192 |

*-Our Formulation

Skin Type

One piece of skin (Female, 37 years, smoker, breast skin) was used for one sample from each batch. A second piece of skin (no further details available) was used for the second sample from each batch. The skin was stored deep frozen (−20° C.) until thawed for this experiment. Full thickness skin was used for this experiment.

Experimental Conditions

Skin permeation cells were prepared containing an exposed skin surface area of 9.6 cm$^2$ and a constantly stirred receptor fluid beneath the skin consisting of 135 ml of ethanol:phosphate buffered saline (25:75 v/v).

Each cell was allowed to equilibrate for 1 hour at 37° C. after which the gel was spread evenly over the skin surface at a concentration of 20 mg/cm$^2$). See table above. The cell was then maintained at 37° C. with an air temperature above the skin of 35° C.

24 hours after application of the gel the experiment was stopped and a portion of the receptor fluid removed. The skin was removed from the cell and any gel remaining on the surface carefully wiped off with dry paper towel followed by paper towel moistened with water. The skin was cut with a scalpel to obtain thin top and thicker lower sections of skin.

This was done in order to obtain layers of skin which approximated the epidermal and dermal layers. Each skin section was weighed and the residual diclofenac extracted with 10 ml of fresh receptor fluid using an ultra turrax homogeniser. The homogenates were centrifuged and a portion of the resultant supernatant solutions removed.

The receptor fluid and skin extracts from each cell were assayed for diclofenac content by using a validated reverse phase high performance liquid chromatography (HPLC) method.

Results
Distribution of Diclofenac 24 hours after application of Diclofenac Gel

| Sample | Receptor μg | Top Skin portion | | | Bottom skin portion | | |
|---|---|---|---|---|---|---|---|
| | | Skin Weight (g) | μg | μg/g | Skin Weight | μg | μg/g |
| (Voltarol Emugel) | | | | | | | |
| 060400 10 93 | 447 | 0.1363 | 101 | 742 | 1.2449 | 217 | 174 |
| 060400 10 93 | 764 | 0.2445 | 141 | 577 | 1.2351 | 202 | 164 |
| Mean | 606 | | | 660 | | | 169 |
| (Our Formulation) | | | | | | | |
| EPDICLO1 | 247 | 0.1535 | 133 | 867 | 1.4663 | 148 | 101 |
| EPDICLO1 | 292 | 0.1647 | 145 | 879 | 1.0022 | 86 | 86 |
| Mean | 269 | | | 873 | | | 93 |
| (Control) | | | | | | | |
| XPB049 | 184 | 0.1275 | 35 | 272 | 1.1324 | 58 | 51 |
| XPB049 | 147 | 0.2068 | 82 | 396 | 1.0893 | 68 | 63 |
| Mean | 165 | | | 334 | | | 57 |

Figure 2:
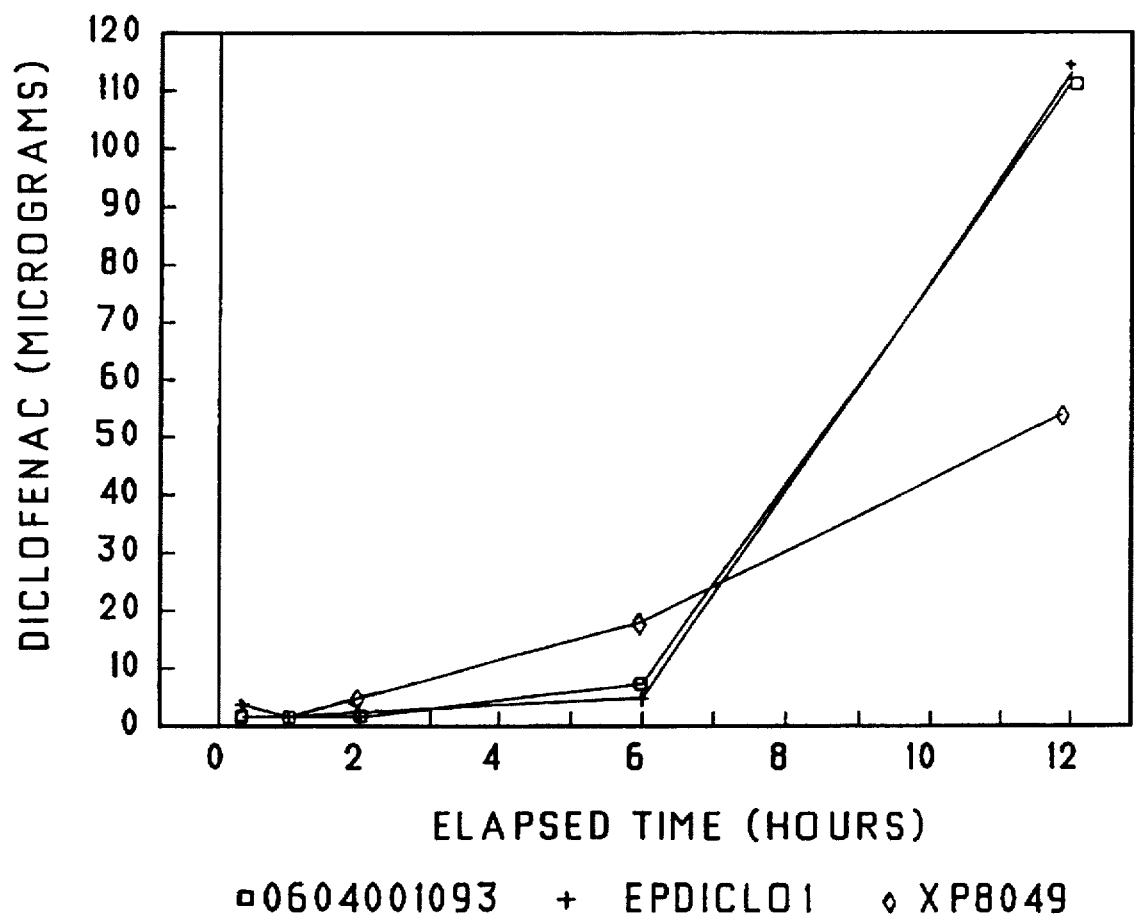
FIG. 2 illustrates the presence of diclofenac in the bottom skin portion after administration of the several compositions.
Figure 3:
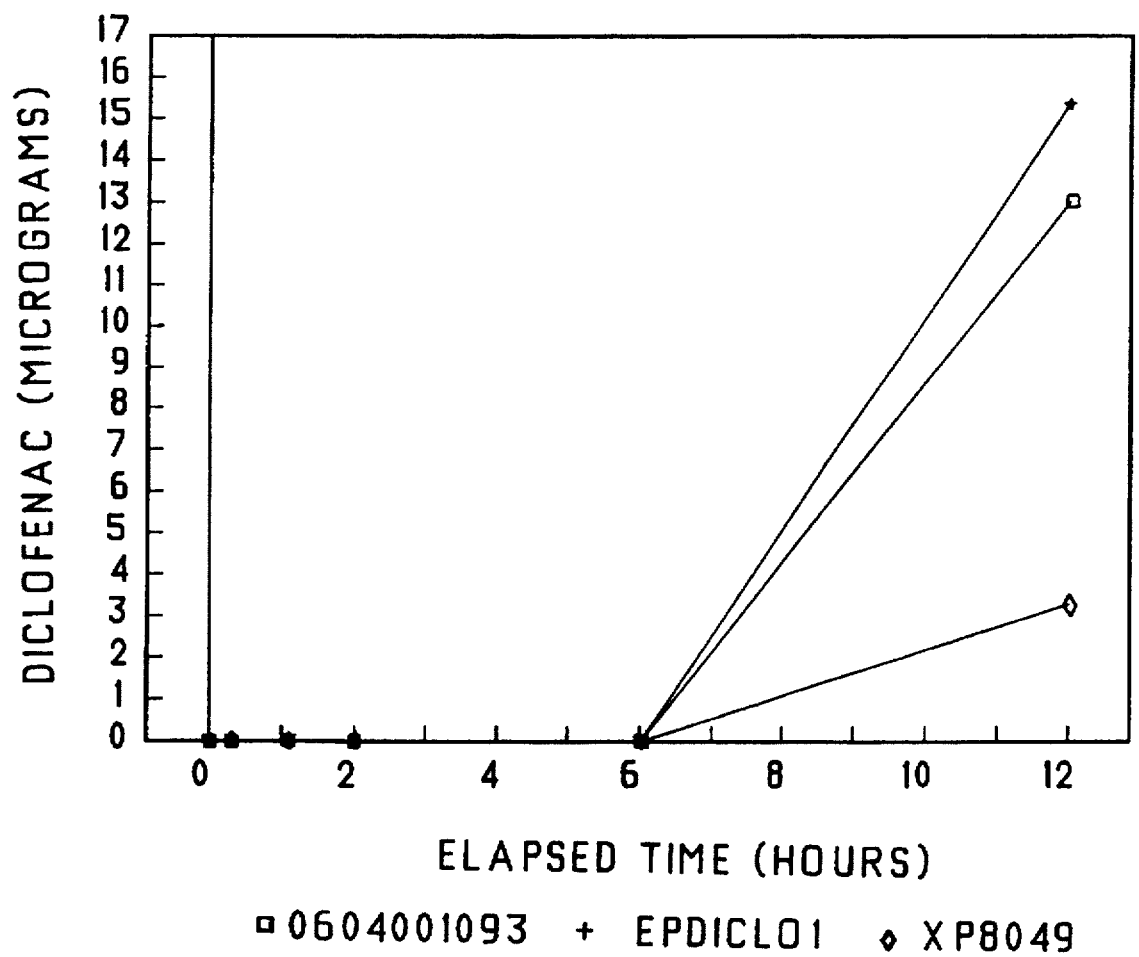
FIG. 3 illustrates the presence of diclofenac in the receptor solution after the elapse of a predetermined time.

Thus having regard to the above and FIGS. 1, 2 and 3, it is clear that the sodium hyaluronate takes the diclofenac into the skin to the epidermis level (See FIG. 1) more rapidly than the Voltarol Emugel or non-hyaluronic acid diclofenac containing control formulation, accumulates it there and retains it there longer. The other formulations permit the NSAID, diclofenac, to pass through the bottom skin portion (dermis) quicker, thereby clearing it from the epidermis and dermis, quicker. Furthermore, more of Applicants' formulation is in the epidermis and in the dermis even after 12 hours.

It is also clear that Applicants' formulations clear into the lymphatic system not through the blood system. Yet the prior art topical formulations have always tried "to drive" the formulations through the skin into the blood for treatment of the disease or condition in the area (i.e. systemic action).

Thus, our composition, formulation and combination, (and dosage amounts thereof) penetrate quickly and rapidly at the site of treatment through the upper skin into the epidermis, where the paccinian bundles are located and the NSAID and the form of hyaluronic acid are accumulated and are retained longer, where needed (for example for the treatment of basal cell carcinoma).

Further, the NSAIDs are retained in the area to be treated with the form of hyaluronic acid. In doing so, they preclude prostaglandin synthesis, in effect, deactivating the synthesis or inhibiting the synthesis, of prostaglandins, permitting the macrophages' scavenger cell activity to eliminate the tumour and lesion. Additionally, a rapid onset of pain relief (analgesic effect) is provided (depending on the amount of NSAID and form of hyaluronic acid) usually where in excess of about 10 mg of the form of hyaluronic acid (preferably hyaluronic acid and salts thereof) is administered per cm$^2$ of surface area comprises the dosage amount administered. However, there are no blood levels of the NSAID in the immediate area of treatment. The forms of hyaluronic acid are thus cleared via the lymphatic system. Then the lymphatics pass the forms of hyaluronic acid, Applicants believe, to the blood system. Thus, the NSAIDs and forms of hyaluronic acid stay at the site to be treated for well in excess of 12–24 hours, a protracted stay.

Thus, over the period of treatment (for example, applications of effective non-toxic dosage amounts of compositions containing for example effective non-toxic dosage amounts of the NSAIDS and effective non-toxic dosage amounts of the sodium hyaluronate, 3 times a day for 2–4 weeks, transport the NSAIDS to to the epidermis to inhibit prostaglandin synthesis to enable the macrophages to "scavenge" the tumour cells and eliminate them. The end result is the successful treatment of the disease or condition at the site of trauma and/or pathology of the skin or exposed tissue, for example, the resolution of, the basal cell carcinoma, the precancerous, often recurrent, actinic keratoses lesions, fungal lesions, "liver" spots and like lesions (found for the most part in the epidermis), squamous cell tumours, metastatic cancer of the breast to the skin, malignancies and/or tumours in the skin, primary and metastatic melanoma in the skin, genital warts cervical cancer, and HPV (Human Papilloma Virus) including HPV of the cervix, psoriasis (both plaque-type psoriasis and nail bed psoriasis), corns on the feet and hair loss on the head of pregnant women, with complete disappearance of the disease or condition as the case may be, by topical therapy without resorting to surgery.

One of the formulations which we have employed successfully is a gel formulation comprising 3% diclofenac in 2.5% sodium hyaluronate formulated as follows:

Formulation 1 (3000 ml.)

| Formula | Supplier | (LOT) | Amount | Percent |
|---|---|---|---|---|
| Glycerine | Life | 1043 | 150 g (119 ml) | 5 |
| Benzyl Alcohol | Caledon | 02517 | 90 g (86 ml) | 3 |
| Diclofenac Sodium | Prosintex | 9113003 | 90 grams | 3 |
| Sodium Hyaluronate (MW 661,660) | Skymark | HG1003 | 75 grams | 2.5 |
| Sterile water balance | Baxter | AW4455 | 2795 ml. | |

Procedure set up stirring apparatus using a 4 liter stainless steel beaker add water, Glycerine, and Benzyl Alcohol; stir to mix add Diclofenac Sodium and stir for 30 minutes then add the Sodium Hyaluronate and stir for 90 minutes initially, stir at a high torque but avoid splashing; as the gel thickens, stir at a lower torque.

The gel is then packaged in a tube or jar or other suitable container for use. Identification of suitable dosage amounts and how they are taken from the container may be provided with the container—for example squeeze "X" cm. of ribbon from the tube; fill spoon or spatula accompanying jar; (the spoon or spatula containing a predetermined dosage amount) then apply and rub into site of trauma and/or pathology (the dosage amount indicated will be such amount of the composition which comprises in excess of about 5 mg. of sodium hyaluronate per cm² (square centimeter) of skin or exposed tissue to which the dosage amount is to be applied. The amount of Diclofenac Sodium was determined in the same manner (having regard to the dosage amount required).

Another such formulation is:

Formulation 2

| Formula | Supplier | (LOT) | Amount | Percent |
|---|---|---|---|---|
| Methoxypolyethylene Glycol 350 | Sigma | 34F-0266 | 300 g. | 20 |
| Benzyl Alcohol | BDH | 23797 | 15 g. | 1 |
| Diclofenac Sodium | Prosintex | 9123012 | 45 g. | 3 |

-continued

| Formula | Supplier | (LOT) | Amount | Percent |
|---|---|---|---|---|
| Sodium Hyaluronate (MW 679,000) | Skymart | HG 1004 | 37.5 g. | 2.5 |
| Sterile Water balance | Baxter | AW45R6 | 1200 ml. | |

Procedure set up stirring apparatus using a 3 liter stainless steel beaker add water, Methoxypolyethylene Glycol 350, and Benzyl Alcohol and stir for 20 minutes to mix add Diclofenac Sodium and stir for 30 minutes to dissolve add Hyaluronate Sodium slowly and stir initially at a high speed, but avoid splashing after addition, stir at a slower speed for 90 minutes; the slower speed reduces the formation of air bubbles the result is a clear, transparent, viscous gel which is put into a container. Once again instructions are given for administration and if applicable measuring devices (to provide a premeasured dosage amount) accompany the container.

Still other formulations are:

Formulation 3

3% Diclofenac in 2.5% HA Gel

| Formula | Supplier | LOT | Amount | Percent |
|---|---|---|---|---|
| Sterile Water | Baxter | AW45K6 | 1200 ml | — |
| Methoxypolyethylene Glycol 350 | Sigma | 34F-0266 | 300 G (273 ml) | 20% |
| Benzyl Alcohol | BDH | 23797 | 15 G (14 ml) | 1% |
| Diclofenac Sodium | Prosintex | 9123012 | 45 g | 3% |
| Sodium Hyaluronate MW 679,000 | Skymart | HG 1004 | 37.5 g | 2.5% |

Procedure

Set up stirring apparatus using a 2 liter stainless steel beaker,

Add water, Methoxypolyethylene Glycol 350, and Benzyl Alcohol and stir for 20 minutes to mix, Add Diclofenoc Sodium and stir for 30 minutes to dissolve.

Add Hyaluronate Sodium slowly and stir initially at a high speed, but avoid splashing.

After addition, stir at a slower speed for 90 minutes, the slower speed reduces the formation of air bubbles, The result is a clear transparent, viscous gel which is poured into jars and tubes. Once again instructions accompany the container and where applicable appropriate devices for providing a premeasured amount of the composition accompany the container.

Formulation 4

5% IBUPROFEN IN 3.0% HA GEL, 50 ml JAR

| Formula | Supplier | LOT | Amount | Percent |
|---|---|---|---|---|
| Sterile Water | Baxter | AW45R6 | 196 ml | — |
| Meglumine | Falk | 15684 | 11 g | 5.5% |
| Ibuprofen | BDH | 19/241 | 10 g | 5% |
| Benzy Alcohol | BDH | 23797 | 2 g | 1% |

-continued

| Formula | Supplier | LOT | Amount | Percent |
|---|---|---|---|---|
| Glycerin | BDH | 2579 | 2 g | 1% |
| Hyaluronate Sodium Mol Wt 661,600 | Skymart | HG 1003 | 6 g | 3% |

PROCEDURE

Set up stirring apparatus using a 300 ml stainless steel beaker.

Add Sterile Water and Meglumine, and stir for 10 minutes.

Add Ibuprofen and stir for 15 minutes.

Add Benzyl Alcohol, followed by Glycerin and stir for 15 minutes.

Finally, add Hyaluronate Sodium slowly and stir initially at a high torque to mix, but avoid splashing.

As the gel thickens, stir at a slow speed for 90 minutes.

Formulation 5

2% PIROXICAM IN 2.5% HA GEL

| Formula | Supplier | LOT | Amount | Percent |
|---|---|---|---|---|
| Sterile Water | Baxter | AW45R6 | 200 ml | — |
| Meglumine | Falk | 15684 | 8 g | 4% |
| Piroxicam | AMSA | 1-010 | 4 g | 2% |
| Hyaluronate Sodium MW 661,600 | Skymart | HG 1003 | 5 g | 2.5% |

PROCEDURE

Set up stirring apparatus using a 300 ml stainless steel beaker.

Add 200 ml of sterile water.

Add 8 grams of Meglumine and dissolve.

Very slowly add 4 grams of Piroxicam and stir for 20 minutes.

Slowly add 5 grams of Hyaluronate Sodium and stir at high speed.

Stir for 90 minutes at a slower speed

COMMENTS

A clear yellowish transparent gel

Formulation 6

5% IBUPROFEN CREAM, 50 ml JAR

OILY PHASE

| Formula | Supplier | LOT | Amount | Percent |
|---|---|---|---|---|
| Liquid wax DICDD | Brooks | L-1424 | 450 g | 15% |
| Brookswax D | Brooks | P-490 | 480 g | 16% |
| Glycerin | BDH | 109109/2578 | 150 g (119 ml) | 5% |
| AQUEOUS PHASE | | | | |
| Sterile Water | Baxter | AW45F1 | 1950 ml | — |
| Meglumine | Falk | 15684 | 150 g | 5% |
| Ibuprofen MW 200,00 | BKH | 19/241 | 150 g | 5% |
| Sodium Hyaluronate | Skymart | 001 | 45 g | 1.5% |
| Preservative Suttocide A | Sutton | SH-107 | 9 g | 0.3% |

PROCEDURE

A—Add all the ingredients of the oily phase A into a 4 liter stainless steel beaker, melt at 55° C., finally heat to 75% when Aqueous Phase B is ready B—Into a 3 liter stainless steel beaker, add 1950 ml water, set up, the stirring apparatus, add the Meglumine, stir to dissolve for 10 minutes.

Slowly add Ibuprofen, stir to dissolve for 20 minutes.

Very slowly add Sodium Hyaluronate and stir for one hour to dissolve all the Sodium Hyaluronate.

Finally, heat to 75° C., with stirring for a total time of 30 minutes.

POUR B INTO A, both at a temperature of 75° C., slowly

Remove the heat source and stir with a strong vortex for one hour.

When the temperature has cooled down to 45° C. add preservative Suttocide A.

Continue stirring at a slower speed until the temperature is 35° C.,

At 35° C. remove the propeller, pour into 50 ml jars.

Formulation 7

1% DICLOFENAC IN 3% HA Gel, 50 ml jar

Quantity 3000 ml

| Formula | Supplier | LOT | Amount | Percent |
|---|---|---|---|---|
| Sterile Water | Baxter | AW45R6 | 2796 ml | —% |
| Glycerin | BDH | 2579 | 50 g (71 ml) | 3% |
| Benzyl Alcohol | BDH | 23797 | 45 g (43 ml) | 1.5% |
| Liquid wax DICDD | Brooks | 191-175 | 90 g | 3% |
| Diclofenac Sodium | Prosintex | 9113003 | 30 g | 1% |
| Hyaluronate Sodium MW 679,000 | Skymout | HG 1004 | 90 g | 3% |

PROCEDURE

Set up stirring apparatus using a 4 liter stainless steel beaker.

Add water, Glycerin, Benzyl Alcohol and Liquid wax DICDD and stir to mix thoroughly for 10 minutes Add Diclofenac Sodium and stir for 30 minutes to dissolve.

Slowly add Hyaluronate Sodium, stirring at a high torque initially during addition.

After addition stir at a slower speed for 90 minutes.

A white opaque viscous gel is formed.

Formulation 8

1% DICLOFENAC IN 3.0% HA Gel, 50 ml tube

Quantity 1500 ml

| Formula | Supplier | LOT | Amount | Percent |
|---|---|---|---|---|
| Sterile Water | Baxter | AW45F1 | 1397 ml | —% |
| Glycerin | Life | 1043 | 45 g (36 ml) | 3% |
| Benzyl Alcohol | Caledon | 02517 | 22.5 g (22 ml) | 1.5% |
| Liquid wax DICDD | Brooks | 191-175 | 45 g | 3% |
| Diclofenac Sodium | Prosintex | 9113003 | 15 g | 1% |
| Sodium Hyaluronate Mol. Wt. 661,600 | Skymart | HG 1003 | 45 g | 3% |

PROCEDURE

Set up stirring apparatus using a 3 liter stainless steel beaker.

Add water, Glycerin, Benzyl Alcohol and Liquiwax DICDD, stir to mix for 10 minutes.

Add Diclofenac Sodium and stir for 30 minutes to dissolve.

Add Sodium Hyaluronate and stir for 90 minutes.

Formulation 9
HYANALGESE CREAM (L)
50 ml tube
Quantity 3000 ml

| FORMULA | SUPPLIER | LOT | AMOUNT | PERCENT |
| --- | --- | --- | --- | --- |
| A. Oily Phase | | | | |
| Liquid Wax DICDD | Brooks/Amisol | | 450 g | 15.0% |
| Brookswax D | Brooks/Amisol | | 480 g | 16.0% |
| Glycerine | Amisol | | 150 g | 5.0% |
| B. Aqueous Phase | | | | |
| Sterile Water | Baxter | AW4YA8 | 1950 ml | —% |
| Meglumine | Falk | | 150 g | 5.0% |
| Sodium Hyaluronate MW 207,000 | Skymart | PO1 | 45 g | 1.5% |
| Ibuprofen | BDH | | 150 g | 5.0% |
| Suttocide A | Sutton | | 9.0 g | 0.3% |

PROCEDURE

A.—Add all the ingredients of the oily phase into a 4 liter stainless steel beaker, melt at 55° C., finally heat to 75° C. when aqueous phase is ready (at 75° C.) to pour in.

B.—Into another 4 liter stainless steel beaker, add 1950 ml water.

Set up the stirring apparatus and add the Meglumine

Stir to dissolve with high torque, then slowly add Ibuprofen

When the Ibuprofen is dissolved, slowly add Sodium Hyaluronate

Stir cold for one hour to dissolve all the ingredients

Finally heat to 75° C. and stir thoroughly throughout a 30 minute period

MIX B INTO A

Slowly pour B into A (both at 75° C.) with stirring

Immediately remove the hot plate (heat) and stir

Stir with a strong vortex for one hour

When the temperature is 45° C., add the preservative Suttocide A

Stir for about an hour to cool to 35° C.

At 35° C. remove the propeller and pour into 50 ml tubes

Pour 50 grams of the cream into each tube

1% BANAMINE IN 2.5% HA GEL (L) XPB 041 Quantity 3000 ml

| FORMULA | SUPPLIER | LOT | AMOUNT | PERCENT |
| --- | --- | --- | --- | --- |
| Sterile Water | Baxter | AW4SA2 | 2400 ml | —% |
| Sodium Hyaluronite MW 661,600 | Skymart | HE1003 | 75 g | 2.5% |
| *Banamine, 100 ml vial | Scheing | O CNXB13 | 300 ml | 1% |
| Banamine, 100 ml vial | Scheing | O CNXB12 | 300 ml | 1% |
| | | | 3000 ml | |

(50 mg/ml) 600 = 30,000 mg
= 30 grams Flunixin in 600 ml

*Banamine contains Flunixin Meglumine (50 mg Flunixin per ml) or 83 mg Flunixin Meglumine

PROCEDURE

Set up stirring apparatus using a 4 liter stainless steel beaker

Add water, stir with a strong vortex, then add sodium Hyoluronate slowly

Then immediately add the Banamine, stir the mixture for 4 hours.

One form of hyaluronic acid and/or salts thereof (for example sodium salt) and homologues, analogues, derivatives, complexes, esters, fragments, and sub-units of hyaluronic acid, preferably hyaluronic acid and salts and thereof, suitable for use with Applicant's invention is a fraction supplied by Hyal Pharmaceuticals Limited. One such fraction is a 15 ml vial of Sodium hyaluronate 20 mg/ml (300 mg/vial-Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and sub-units of hyaluronic acid, preferably hyaluronic acid and salts thereof, may comprise hyaluronic acid and/or salts thereof having the following characteristics:

a purified, substantially pyrogen-free fraction of hyaluronic acid obtained from a natural source having at least one characteristic selected from the group (and preferably all characteristics) consisting of the following:

i) a molecular weight within the range of 150,000–225,000;

ii) less than about 1.25% sulphated mucopolysaccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25; and xii) a pH within the range of 7.3–7.9. Preferably, the hyaluronic acid is mixed with water and the fraction of hyaluronic acid has a mean average molecular weight within the range of 150,000–225,000. More preferably, the fraction of hyaluronic acid comprises at least one characteristic selected from the group (and preferably all characteristics) consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

x) a UV extinction coefficient at 257 nm of less than about 0.23;

xi) a UV extinction coefficient at 280 nm of less than 0.19; and xii) a pH within the range of 7.5–7.7

Applicants also propose to use sodium hyaluronate produced and supplied by LifeCore™ Biomedical, Inc., having the following specifications:

| Characteristics | Specification |
| --- | --- |
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, maximum ppm | |
| As  Cd  Cr  Co  Cu  Fe  Pb  Hg  Ni | |
| 2.0  5.0  5.0  10.0  10.0  25.0  10.0  10.0  5.0 | |
| Microbial Bioburden | None observed |
| Endotoxin | <0.07 EU/mg NaHy |
| Biological Safety Testing | Passes Rabbit Ocular Toxicity Test |

Another form of sodium hyaluronate is sold under the name Hyaluronan HA-M5070 by Skymart Enterprises, Inc. having the following specifications:

Specifications' Test Results

| Lot No. | HG1004 |
| --- | --- |
| pH | 6.12 |
| Chondroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69% |
| Intrinsic Viscosity | 12.75 dl/s (XW: 679,000) |
| Nitrogen | 3.14% |
| Assay | 104.1% |
| Microbiological Counts | 80/g |
| E. coli | Negative |
| Mold and Yeast | Not more than 50/g |

Other forms of hyaluronic acid and/or its salts, and homologues, derivatives, complexes, esters, fragments and sub units of hyaluronic acid may be chosen from other suppliers, for example those described in prior art documents provided the form of hyaluronic acid chosen is suitable for transport of the medicine.

The following references teach hyaluronic acid, sources thereof, and processes for the manufacture and recovery thereof which may be suitable.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 $cm^3/g$., and preferably greater than about 2000 $cm^3/g$.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree—$cm^2$/mole (of disaccharide) measured at 220 nanometers;

(f) no significant cellular infiltration of the vitreous and anterior chamber, no flare in the aqueous humour, no haze or flare in the vitreous, and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

In order to determine the blood levels in patients using formulations made according to embodiments of the invention, a study of the pharmacokinetic profiles of two topical diclofenac formulations after repeat dosing were undertaken.

One such product was the product Voltarol Emulgel marketed in the United Kingdom by Geigy. The other was a Diclofenac preparation in Hyaluronic Acid.

This was an open, repeat dose, crossover comparison using a randomized balanced block in six healthy volunteers.

The study consisted of administration with one, two week period in between periods, each period lasting fourteen days. The test articles applied were for the first six days of each period and the seventh day was study day during which the final application is made and blood samples taken.

The approximate duration of the study including pre and post study screening was six weeks.

Doses

Diclofenac (3.0%) with Hyaluronic Acid (2.5%)

Dose: Approximately 2 g, three times daily

Route: Topical (W1) Voltarol Emulgel, Diclofenac diethylammonium salt 1.16 g aqueous gel (Geigy)

Dose: Approximately 2 g, three times daily

Route: Topical (W1)

ADMINISTRATION: to suitable patients

Subjects applied one of the designated test articles topically to the calves and massaged into the skin, in a dose of approximately 2 g per application three times a day for six consecutive days. The size of a 2 g dose was prepared by comparison with a silicone example given to each subject.

On the seventh day, the cream was applied once, in the same manner as before, under the supervision of the staff of the Clinical Investigation Unit.

After a washout period of one week the procedure was repeated with the alternate test article.

The following were the results of the tests:

(H=hyaluronic acid formulation)

(V=Voltarol Emulgel)

PERIOD 1

All concentrations ng ml–1

| | TIME POINT (hours) | | | | | | | | | | | |
|---|---|---|---|---|---|---|---|---|---|---|---|---|
| SUBJECT | 0 | 0.25 | 0.5 | 1 | 2 | 3 | 4 | 5 | 6 | 8 | 10 | 12 |
| H-1 | 10.3 | 7.1 | 6.4 | ND | ND | 5.4 | 6.5 | 5.1 | ND | ND | ND | ND |
| H-2 | ND | 5.1 | ND | 5.1 | ND | ND | ND | ND | ND | 5.1 | ND | ND |
| ND | ND | ND | 5.5 | 5.2 | ND | ND | ND | ND | ND | ND | ND | V-3 |
| ND | ND | ND | ND | ND | ND | ND | ND | ND | ND | ND | ND | H-4 |
| ND | ND | ND | ND | ND | ND | ND | ND | ND | ND | ND | ND | V-5 |
| ND | ND | ND | ND | ND | ND | ND | 8.4 | ND | ND | ND | ND | V-6 |

ND = NONE DETECTED (>5.0 ng ml$^{-1}$)

PERIOD II
All concentrations ng ml−1

| | TIME POINT (hours) | | | | | | | | | | | |
|---|---|---|---|---|---|---|---|---|---|---|---|---|
| SUBJECT | 0 | 0.25 | 0.5 | 1 | 2 | 3 | 4 | 5 | 6 | 8 | 10 | 12 |
| V-1 | ND | ND | ND | ND | ND | ND | ND | ND | ND | ND | ND | ND |
| V-2 | ND | ND | ND | ND | ND | ND | ND | ND | ND | ND | ND | ND |
| H-3 | ND | ND | ND | ND | ND | ND | ND | ND | ND | ND | ND | ND |
| V-4 | ND | ND | ND | ND | ND | ND | ND | ND | ND | ND | ND | ND |
| H-5 | ND | ND | ND | ND | ND | ND | ND | ND | ND | ND | ND | ND |
| H-6 | ND | ND | ND | ND | ND | ND | ND | ND | ND | ND | ND | ND |

ND = NONE DETECTED (>5.0 ng ml$^{-1}$)

Other tests were undertaken to determine blood levels comparing Proflex (a formulation containing Ibuprofen) and the following formulation containing hyaluronic acid and Ibuprofen.

HYANALGESE CREAM (L)xPB 022

50 ml tube
Quantity 3000 ml

| FORMULA | SUPPLIER | LOT | AMOUNT | PERCENT |
|---|---|---|---|---|
| A. Oily Phase | | | | |
| Liquid Wax DICDD | Brooks/Amisol | | 450 g | 15.0% |
| Brookswax D | Brooks/Amisol | | 480 g | 16.0% |
| Glycerine | Amisol | | 150 g | 5.0% |

| FORMULA | SUPPLIER | LOT | AMOUNT | PERCENT |
|---|---|---|---|---|
| B. Aqueous Phase | | | | |
| Sterile Water | Baxter | AW4YA8 | 1950 ml | —% |
| Meglumine | Falk | | 150 g | 5.0% |
| Sodium Hyaluronate MW 207,000 | Skymart | PO1 | 45 g | 1.5% |
| Ibuprofen | BDH | | 150 g | 5.0% |
| Suttocide A | Sutton | | 9.0 g | 0.3% |

The following were the results (A) PROFLEX

| SUBJECT | Time after administration (Hours) | | | | | | | | | | | | |
|---|---|---|---|---|---|---|---|---|---|---|---|---|---|
| Number | PD | 0 | 0.25 | 0.5 | 1 | 2 | 3 | 4 | 5 | 6 | 8 | 10 | 12 |
| 1 | ND | 0.41 | 0.37 | 0.37 | 0.32 | 0.30 | 0.27 | 0.27 | 0.24 | 0.37 | 0.31 | 0.31 | 0.16 |
| 2 | ND | 0.12 | 0.12 | 0.08 | 0.11 | 0.12 | 0.12 | 0.07 | 0.08 | 0.09 | 0.08 | ND | 0.06 |
| 3 | ND | 0.09 | 0.08 | 0.07 | ND | ND | ND | ND | ND | ND | ND | ND | ND |
| 4 | ND | 0.12 | 0.14 | 0.16 | 0.11 | 0.11 | 0.25 | 0.24 | 0.17 | 0.13 | 0.16 | 0.11 | 0.13 |
| 5 | ND | 0.14 | 0.19 | 0.19 | 0.15 | 0.16 | 0.16 | 0.14 | 0.12 | 0.11 | 0.13 | 0.10 | 0.07 |
| 6 | ND | 0.11 | 0.09 | 0.09 | 0.06 | 0.07 | 0.05 | 0.05 | 0.05 | ND | ND | ND | ND |
| Mean | 0.00 | 0.17 | 0.17 | 0.16 | 0.13 | 0.13 | 0.14 | 0.13 | 0.11 | 0.12 | 0.11 | 0.09 | 0.07 |
| S.D. | 0.00 | 0.12 | 0.10 | 0.11 | 0.10 | 0.10 | 0.10 | 0.10 | 0.08 | 0.13 | 0.11 | 0.12 | 0.06 |

(B) HYALURONIC ACID AND IBUPROFEN

| SUBJECT | | Time after administration (Hours) | | | | | | | | | | | |
|---|---|---|---|---|---|---|---|---|---|---|---|---|
| Number | PD | 0 | 0.25 | 0.5 | 1 | 2 | 3 | 4 | 5 | 6 | 8 | 10 | 12 |
| 1 | ND | 0.11 | 0.11 | 0.12 | 0.08 | 0.08 | 0.09 | 0.11 | 0.12 | 0.08 | 0.11 | 0.16 | 0.14 |
| 2 | ND | 0.22 | 0.21 | 0.26 | 0.17 | 0.24 | 0.24 | 0.25 | 0.23 | 0.19 | 0.19 | 0.20 | 0.14 |
| 3 | ND | 0.17 | 0.10 | 0.12 | 0.09 | 0.08 | 0.07 | 0.06 | ND | 0.06 | 0.26 | 0.09 | 0.05 |
| 4 | ND | ND | ND | ND | ND | ND | ND | ND | ND | ND | ND | ND | ND |
| 5 | ND | 0.17 | 0.16 | 0.16 | 0.12 | 0.09 | 0.10 | 0.11 | 0.10 | 0.09 | 0.10 | 0.07 | ND |
| 6 | ND | 0.07 | 0.07 | 0.09 | ND | ND | ND | ND | ND | ND | ND | ND | ND |
| Mean | 0.00 | 0.12 | 0.11 | 0.13 | 0.08 | 0.08 | 0.08 | 0.09 | 0.08 | 0.07 | 0.11 | 0.09 | 0.06 |
| S.D. | 0.00 | 0.08 | 0.07 | 0.08 | 0.06 | 0.08 | 0.08 | 0.09 | 0.09 | 0.07 | 0.10 | 0.08 | 0.07 |

ND None detected <0.05 µg/ml

The above clearly indicates that the blood levels are much less using hyaluronic acid to administer the NSAID.

PRELIMINARY REPORT

A trial was conducted using a gel composition (Number 109) comprising 3% Diclofenac in 2.5% Hyaluronic Acid as previously described and a composition containing Diclofenac sodium salt 3% but not including any form of hyaluronic acid. (Number 112) The trial was conducted with 60 patients who were randomly assigned to test preparations number 109 or 112. The trial has not been completed as yet but so far 31 patients have finished the protocol. Patients were diagnosed:

4 Rheumatoid arthritis of the knee

8 Myofascial trigger points in the M. trapezius area

12 Periarthropathies of knee without effusion

7 Periarthropathies with effusion in the knee joint

The 31 patients were aged 22–75 years (27 females, 4 males). All patients were hospitalized. Patients entering the trial were thoroughly examined and type of extraarticular or articular rheumatism assessed.

On day 1 baseline pain was assessed on the 10 cm visual analogue scale (VAS) and pain measurement of the quantititative pain sensitivity using a pressure tolerance meter (PTM) were performed. Then test gel—approximately 2.g—was massaged on to the skin of maximum pain. Gels were applied 3 times daily.

0.5, 1, 1.5, and 2 hours after morning application measurements of pain sensitivity were carried out and values recorded.

This procedure was countinued on day 2, 3 and 4; measurements (VAS and PTM) of pain severity were done on day 1, 2 and 4.

Prior of the beginning of the study and at the end on day 4, physician's global assessment, assessment of swelling, tenderness and limitation of movement were recorded.

As the study is ongoing statistical evaluation is not yet available. For further details see Table 1.

TABLE 1

| | Composition 109, n = 16 | Composition 112, n - 15 |
|---|---|---|
| Reaction | | |
| Good Alleviation of pain | 13 | 8 |
| Moderate Alleviation of pain | 2 | 2 |
| No Alleviation of pain | 1 | 5 |

From the data recorded we have concluded that the patients to whom composition 109 was administered did better in terms of earlier and longer lasting analgesic effect (up to 4 hours) than the 112 composition especially in patients with myofascial trigger points and with periarthropathies of the knee joints without effusions. Neither composition 109 nor composition 112 treated patients showed any effect on swelling if any swelling exist at all. Systemic side effects have not been observed; one patient to whom composition 112 was administered showed reddening of the skin on the site of application.

Any intake of system NSAIDS, corticosteroids and other analgesics was not allowed one week before and during the trial.

EXAMPLES

The following examples are offered to illustrate uses of Applicants' invention.

Example 1

A male patient had a number of lesions (basal cell carcinoma), including one on his forehead which was a combination of major "horny epithelium" and some degree of ulceration. After continuous treatment with Formulation 1 (several times per day for several weeks of dosage amounts squeezed from tubes as ribbons of composition), the lesions showed epithelialization, no hemorrhagic areas, and no initiated areas (as they were in the past without our treatment). The "horny epithelium" and ulceration of the forehead lesion were also gone. The patient had a complete successful response with the formulation. All basal cell carcinoma lesions had been resolved and disappeared. There has been no recurrence.

Example 2

60 year old male tennis player had sore elbow and basal cell carcinoma on forearm proximate sore elbow. Patient tried Formulation 1 to abate pain in tennis elbow. (Dr. Falk was not treating this patient for anything at the time, did not know of the basal cell proximate the elbow and merely offered the formulation for pain relief of the elbow instructing the patient to squeeze a ribbon of the composition and apply and rub into the sore elbow). However, the formulation "spilled" over onto the Patient's basal cell carcinoma. Patient was planning to have basal cell carcinoma removed surgically by another doctor, but when the patient returned to see the doctor, the basal cell carcinoma was disappearing (because of spill-over of Formulation 1). Dr. Falk was then advised and treatment was now undertaken by Dr. Falk with direct application of Formulation 1 to the lesion 3 times a day for two additional weeks. After two weeks, the basal cell carcinoma disappeared. There has been no recurrence.

Example 3

Male, mid to late 40's had severe basal cell carcinoma on left temple. Doctors recommended its removal by surgery.

However, the surgery would have been risky because of the lesion's proximity to facial nerves.

Patient saw Dr. Falk who gave him Formulation 2 to be applied in dosage amounts 3 times daily.

After 14 days, 75% of the lesion was gone. Surgery was postponed and the treatment was continued. Application of dosage amounts of Formulation 2 was continued for an additional two weeks. At the end of the 2-week period, the lesion was completely resolved and disappeared without any surgery being required. There has been no recurrence.

Example 4

Male, early 40's, had recurrent actinic keratoses lesion on his right temple. Early attempts at removal by third parties involved the application of liquid nitrogen (twice) without final resolution. The lesion kept recurring. The patient was sent to Dr. Falk who treated the lesion with Formulation 1 with applications of dosage amounts 3 times daily for 7 days. After 7 days, the lesion was completely resolved with no subsequent recurrence.

Example 5

A male patient suffering from kyphosis suffered from constant back pain. Taking analgesics orally and rubbing back preparations onto his back did little to alleviate the back pain. When NSAIDs in hyaluronic acid (sodium hyaluronate) were applied directly to the back, the back pain eased and disappeared.

With indomethacin (dissolved in N-methyl glucamine) and naproxen both dissolved in hyaluronic acid, the patient experienced some side effects. However, with Toradol™ (the [±] form tromethamine salt of ketorolac—a prostaglandin biosynthesis inhibitor and analgesic and anti-inflammatory, the back pain eased and disappeared for some time and there were no side effects. The compositions were applied generously onto the sites of back pain.

Example 6

A male patient with basal cell carcinoma was first treated by an oncologist who attempted to surgically excise the lesion (without success) and then irradiated the lesion again without success. The patient then attended before Dr. Falk who applied Applicant's formulation (diclofenac with sodium hyaluronate and excipients). Application was made three times daily for about a month and the lesion disappeared. Some excoriation anterior and slightly superior developed over the last two weeks but was cleared by the application of hyaluronic acid by itself.

This resolution clearly indicates that even with prior applications of unsuccessful therapies (surgery and irradiation), Applicant's formulations can be used successfully.

Example 7

In another patient, a drug (methotrexate) was carried in hyaluronic acid and applied topically to a patient with psoriasis. The formulation was absorbed and the psoriasis cleared.

Example 8

A patient with dermal (skin) metastases in a fibratic scar form and metastatic cancer in the form of musculoskeletal involvement in her thorax.

On topical application of our formulation comprising diclofenac (Voltaren) in hyaluronic acid (sodium hyaluronate), her pain decreased dramatically and her skin and boney involvements steadily improved.

TOPICAL DICLOFENAC ACID 3% IN HYALURONIC ACID GEL (2.5%) BASE

A practitioner reviewed the effectiveness of topical Diclofenac Acid 3% in hyaluronic acid gel (2.5%) base in acute traumatic injuries of no longer than 3 days duration. The cases were all in the spectrum of ages between 18 and 65. Normal exclusion criteria were followed regarding exclusion of pregnancy, aspirin or N.S.A.I.D., allergies or active peptic ulceration.

As an overall, the following impressions were gained from 30 cases:

1. The topical H.D.(composition comprising sodium hyaluronate and diclofenac) had an obvious analgesic action with onset occurring rapidly within one hour; this is a phenomenon not obviously seen with other non-steroidals that we have used.
2. There was a very definite patient acceptance of the gel as a form of treatment, being logical, easy to apply, without local or systemic side effects, rapid absorption with no staining of clothing.
3. The anti-inflammatory action was equivalent on a "guestimate" based on experience of similar injuries to oral N.S.A.I.D.s, without the threat or risk of side effects.

In summary, compared with other topical N.S.A.I.D.s the analgesic effect is distinct, the anti-inflammatory is equal to oral N.S.A.I.D.s and the patients' acceptance is far superior to any other diclofenac or piroxicam topical that the practitioner evaluated.

Following the practitioner's basic preamble regarding the parallelism of topical N.S.A.I.D.s and topical steroids,the practitioner has used the former in contact dermatitis, insect bites and U.V. erothema, all with very positive effects, again pointing direction to trials of a double blind nature in these fields.

CHRONIC CONDITIONS-EVALUATIONS
2.5% HYALURONIC ACID WITH 3% DICLOFENIC ACID (HD)

| Patients Initials (M) or (F) | Date Of Birth | File No. | Diagnosis | Comments on Outcome | Positive (P) Negative (N) Unable to Comment (U) |
|---|---|---|---|---|---|
| LA (M) | 11.04.56 | | Hyper-aesthesia | Severe discomfort following extensive surgery to dorsal spine with insertion of rods in 1989. Even contact with clothes produced significant discomfort. Initially treated with EMLA with only transient anaesthetic results, however even after 3 days treatment with Hyal diclofenac acid noticed marked decrease in supersensitivity which has continued for at least 4 weeks while still using gel. | P Example of peripheral action on super-sensitization of nerve ending queried. |
| KB (F) | 08.06.58 | | Chronic chondromalacia perhaps dating back to 1976. | Treated right knee which was worse initially and was amazed at the response, then started to treat left knee that was not so painful, again with positive response. Here we have a built-in control | P |
| DB (F) | | | Chronic neurogenic ankle with associated dysaesthesia. | Initially felt some improvement which was not continued although initially quite positive-query placebo reaction. | N |
| DC (F) | 07.11.51 | | Chronic back pain-query due to facet syndrome or trigger points, really diagnosis uncertain. | | N |
| CC | 16.01.25 | | Chronic capsulitis right hip right knee | Definite effect over knee where application to get distance short. No obvious effect over hip. | P |
| AG (F) | 07.11.56 | | Myositis in rhomboids muscles following motor vehicle accident | Initially given placebo in error, only marginal or minimal effect, if any. Found active to be effective while being used, did not cure condition which needed trigger point therapy. | P |
| CH (F) | 22.08.61 | | Chronic relapsing tendonitis right elbow | No significant effect, nor has aggressive therapy since including injection with cortisone and numerous opinions. | N |
| SH (F) | 16.07.55 | | Tendonitis and myositis | Control of tendonitis while using preparation. Is now back at work. | P |
| DM (M) | 17.06.47 | | Neuronitis | This patient has a very unusual pain in his left groin following nerve injury, with the use of preparation noticed decrease in pain sensation while on medication. Hyperaesthesia altered although pain (which may be phantom) still present. | U |
| PJ | 15.06.45 | | Capsulitis of right wrist | Symptoms improved 50% while using Hyal diclofenac acid, however, on discontinuation pain reappeared. Exact etiology uncertain. | U |

-continued

CHRONIC CONDITIONS-EVALUATIONS
2.5% HYALURONIC ACID WITH 3% DICLOFENIC ACID (HD)

| Patients Initials (M) or (F) | Date Of Birth | File No. | Diagnosis | Comments on Outcome | Positive (P) Negative (N) Unable to Comment (U) |
|---|---|---|---|---|---|
| DJ (F) | | | Dorsal myositis | Control while using gel equal and with less effects than tiger balm. Controlled symptoms while using medication. Exact diagnosis as to cause of myositis uncertain. | P |
| DK (F) | 27.08.38 | | Severe capsulitis left shoulder | This patient has had capsulitis left shoulder for many years and treated with only transient relief with cortisone injections, poor relief with topical piroxicam. Was started on topical diclofenac acid and noticed relief of pain in 20 minutes continuing for 4-6 hours; See letter March 11/92. At present is using H.D. regularly, has found it to be useful in other areas of chronic pain. Is President North American Chronic Pain Association, has good insight into medication and placebos etc. Has two D.C.S. implants. | P Extremely rewarding case |
| JL (M) | 10.12.45 | | Chronic myositis secondary to query facet syndrome | Pain has failed to respond to many aggressive ments. | N |
| RMC (F) | 13.06.57 | | Neuronitis following facet rhizotomy with resulting pain in her back | It is a difficult case with considerable overlay, she obtained some relief with H.D., would estimate 30-40% Interestingly hyperanaesthesia was decreased. | U |
| RM (F) | 20.09.52 | | Chronic capsulitis- | Using H.D. significant improvement in pain while used, on stopping treatment recurrence of pain needed intra-articular cortisone. | P |
| GM (F) | | | Sub acute tendonitis right ankle | Rapid resolution of pain within one day and positive return of function. | P |
| PM (F) | 20.09.46 | | Acute on chronic osteo- first metatarsal phalyngeal joints | Rapid analgesic response with rapid settlement. | P |
| DN (F) | 10.03.44 | | Chronic fasciaitis of feet | Excellent response to application of H.D. with occlusion. Had failed to respond to oral N.S.A.I.D.s and physiotherapy. Query positive result due to short application target distance in a vascular tissue. | P |
| BP (F) | 04.03.20 | | Severe chronic arthritis of the knee. Unable to take oral N.S.A.I.D.s | Initially one knee treated with such good results both knees treated, see letter. Not only did pain decrease but marked swelling around knees. Significant relief of pain and increase in movement as a result of this and perhaps reduction of swelling. | P Side effects- non/Incidental resolution of area of thrombophlebitis below area |

CHRONIC CONDITIONS-EVALUATIONS
2.5% HYALURONIC ACID WITH 3% DICLOFENIC ACID (HD)

| Patients Initials (M) or (F) | Date Of Birth | File No. | Diagnosis | Comments on Outcome | Positive (P) Negative (N) Unable to Comment (U) |
|---|---|---|---|---|---|
| | | | | Interestingly has severe superficial varicose veins developed thrombophlebitis around right knee and the area treated by chance showed far less redness and tenderness than the thrombophlebitis below this area. | of treatment |
| SP (M) | 06.11.48 | | Idiopathic diffuse capsuilitis of hands | Has had similar episodes with poor response to many treatments including N.S.A.I.D.s per os | U |
| WS | 04.06.45 | | Chronic neuronitis due to injury to lateral cutaneous nerve of thigh | Has been exposed to numberous treatments including tow attempts of surgery without effect. There is decrease in hyperaesthesia but no change in pain. | U |
| MS (F) | 04.06.28 | | Chronic capsuilitis | Failed to respond to number of treatments, good background resolution of pain, however, still had acute pain with certain movements. | P |
| IS (F) | 15.01.49 | | Chronic capsulitis | Had failed to respond to numerous treatments including oral and topical N.S.A.I.D.s Using H.D there was equivalent control of pain as with other therapies which lasted while medication was used. Referred for surgical opinion. | P |
| GS (F) | 26.03.47 | | Chronic tendosinovitis tion. | Oral diclofenac acid discontinued due to gastritis and also history of ulceration. Control using H.D. equal to or better than oral N.S.A.I.D.s. | P |
| VK (F) | 01.01.39 | | Chronic tendonitis. | Good relief of pain and tenderness while using H.D. however on discontinuation of gel symptoms returned, treated with intramuscular steroids. | P for pain N for resolution |
| GH (M) | 03.11.21 | | Acute on chronic osteoarthritis left hand | In view of age and general parous medical condition, ideal for topical. Red been previously on topical piroxicam for left shoulder capsulitis. | P Commented or better absorption compared to topical piroxicam |
| JA (M) | 06.02.58 | | Severe posttraumatic and surgical osteoarthritis of left leg-with staples Poor result to oral N.S.A.I.D.s also gastric irritation. | Produced good superficial analgesia especially where staples were irritating subcutaneous tissue, little effect on deeper, severe osteoarthritic pain of knee. This pain was of considerable severity, needing narcotics. | P |
| IM (M) | 30.11.51 | | Chronic superficial myositis | Severe rhomboid inflammation right side, treated with H.D., very definite improvement in pain and tenderness. | P |

CHRONIC CONDITIONS-EVALUATIONS
2.5% HYALURONIC ACID WITH 3% DICLOFENIC ACID (HD)

| Patients Initials (M) or (F) | Date Of Birth | File No. | Diagnosis | Comments on Outcome | Positive (P) Negative (N) Unable to Comment (U) |
|---|---|---|---|---|---|
| TK (F) | 23.04.70 | | Acute on chronic capsulitis due to sports injury right hand. | Excellent rapid analgesic followed by anti-inflammatory response in young women who could not take oral N.S.A.D.s due to past gastritis. | |
| AD (F) | 03.01.49 | | Chronic diffuse pain thought to be myositis | Poor response to H.D. After intensive investigation and numerous consultations and treatment, pain still undiagnosed and unresponsive. | N |
| NH (F) | 25.03.25 | | Subacute capsulitis right ankle | Excellent response analgesic and anti-inflammatory-wise within a few days. Marked clinical improvement. In view of this patient's parous general medical condition and hypertension, not. suitable for oral NSAIDs. | P |
| MD | 18.04.34 | | Subacute rheumatoid arthritis | Had failed to respond to oral N.S.A.I.D.s, which caused gastritis, tried topical piroxicam with negative effects. Negative response to H.D. | N |
| MW (F) | 07.05.46 | | Heberden's nodes, painful, swollen causing difficulty in movement | Very slow positive outcome, initially improvement in pain followed by reduction in swelling. Etiology of this condition is unknown, partly genetic. Would have been interesting to treat alternate digits, plus or minus thermographic confirmation. | P |
| LP (F) | 20.07.23 | | Acute on sub-acute osteo arthritis of the hands with Heberden's nodes | Initially treated with Idarac; poor response overall, some improvement in generalised arthritis of hands but none on Heberden's nodes. Pain flared on stoppiny Idarac due to gastritis. Started on H.D., especially favourable results with subsidence of tenderness of nodes and settling of arthritis. Interestingly enough, no flare up on discontinuation after one month | P |
| JG (F) | 24.11.50 | | Post facet rhizotomy hyper- aesthesia, with marked pain and hyper- aesthesia between scapulae | Had failed to respond to oral N.S.A.I.D.s and E.M.L.A. Application of H.D. improved the surface pain significantly but had no effect on the deeper pain. My impression was that the deeper pain was due to section of the facet and beyond the reach of the topical medication. There is little doubt that the skin sensitivity was decreased | U |
| SW (F) | 10.09.39 | | Knee pain due to chondro | Upset in past due to oral N.S.A.I.D.s., also hypertension made one loathe to | P (Effective while |

CHRONIC CONDITIONS-EVALUATIONS
2.5% HYALURONIC ACID WITH 3% DICLOFENIC ACID (HD)

-continued

| Patients Initials (M) or (F) | Date Of Birth | File No. | Diagnosis | Comments on Outcome | Positive (P) Negative (N) Unable to Comment (U) |
|---|---|---|---|---|---|
| | | | malacia | use this medication with serum levels. Good analgesic and anti-inflammatory action, however on discontinuation pain flared. Seen for arthroscopic surgery with relief of pain. | being used) Condition only cured by surgery |

*Two types of pain-response in only one

1. Interestingly in the whole series, there was not one case of local side effects and as expected from past studies, no general or systemic. Since this report was prepared we have had one case of mild folliculitis which responded to discontinuation of treatment, will rechallenge.
2. A number of patients commented that they felt the gel improved the texture and softness of their skin, and commented that it was messy or stained their clothes.
3. In one case of topical thrombophlebitis where the inflamed vein crossed the area of treatment, the vein in the area of treatment improved while that outside at a distance did not. Again, similar to using oral N.S.A.I.D.s. ***.

Figure 9A:
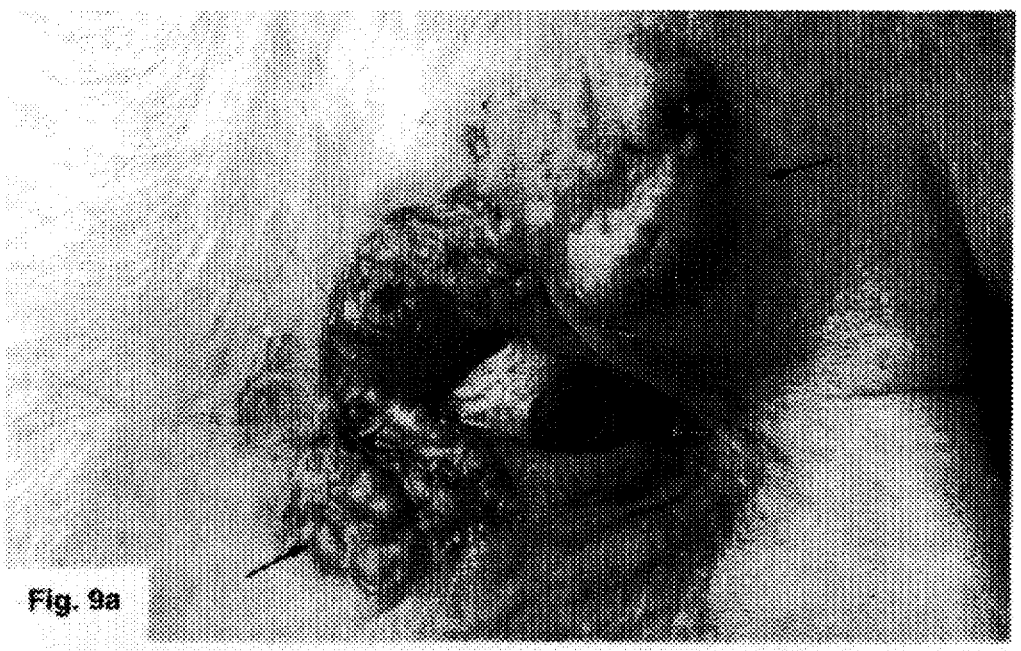
FIGS. 9a–9c show the response of basal cell carcinoma in a 70 year old female patient to treatment with NSAIDs and HA gel.
Figure 9B:
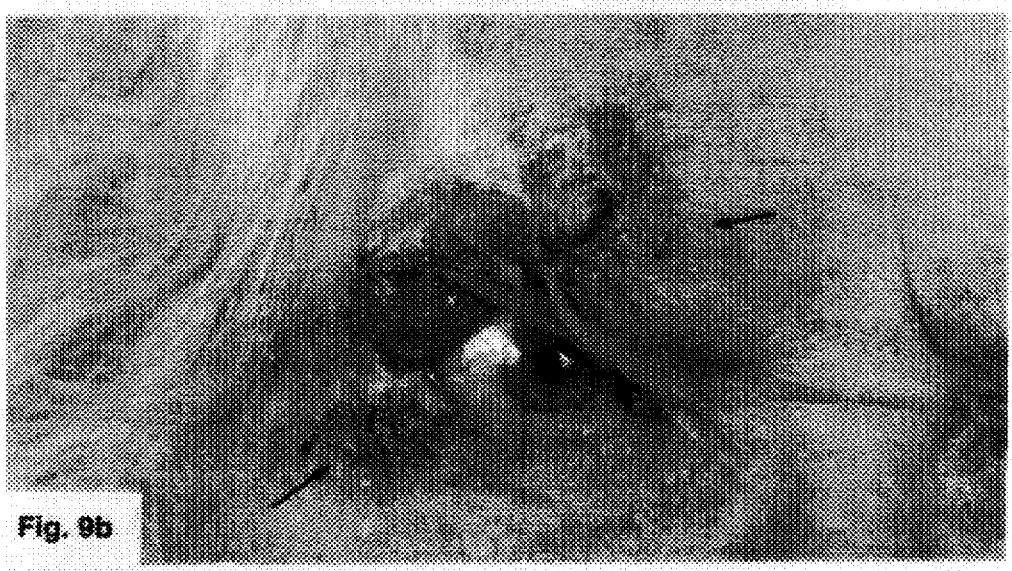
Figure 9C:
Figure 10A:
FIGS. 10a and 10b show the response of p815 tumors in mice (strain DBA$_2$) to treatment with novantrone and HA gel.
Figure 10B:
Figure 11:
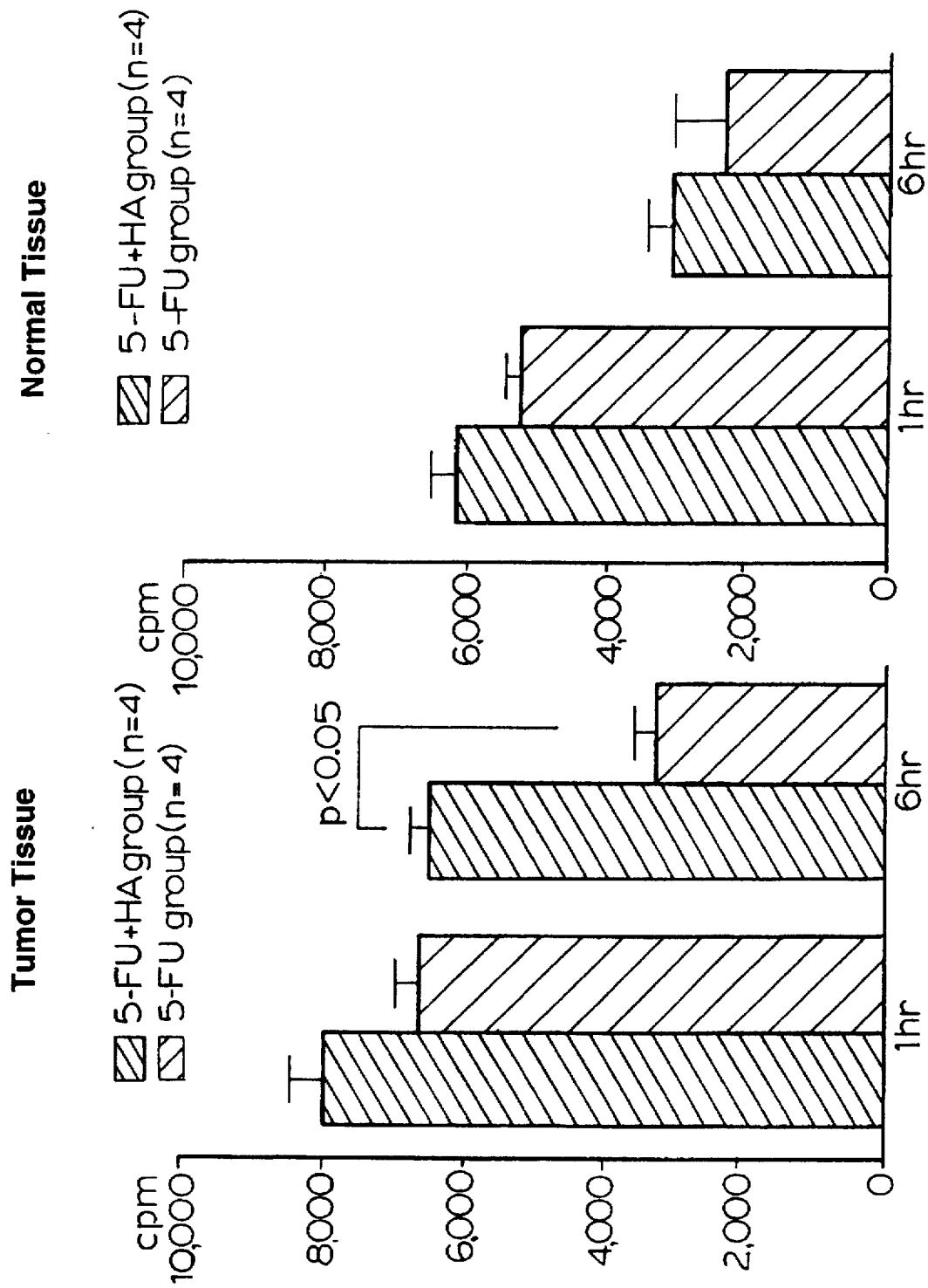
FIG. 11 shows the results of the anti-cancer agent 5-fluoracil when administered alone and when administered with HA at varying times for tumor skin and normal skin, respectively.
Figure 12:
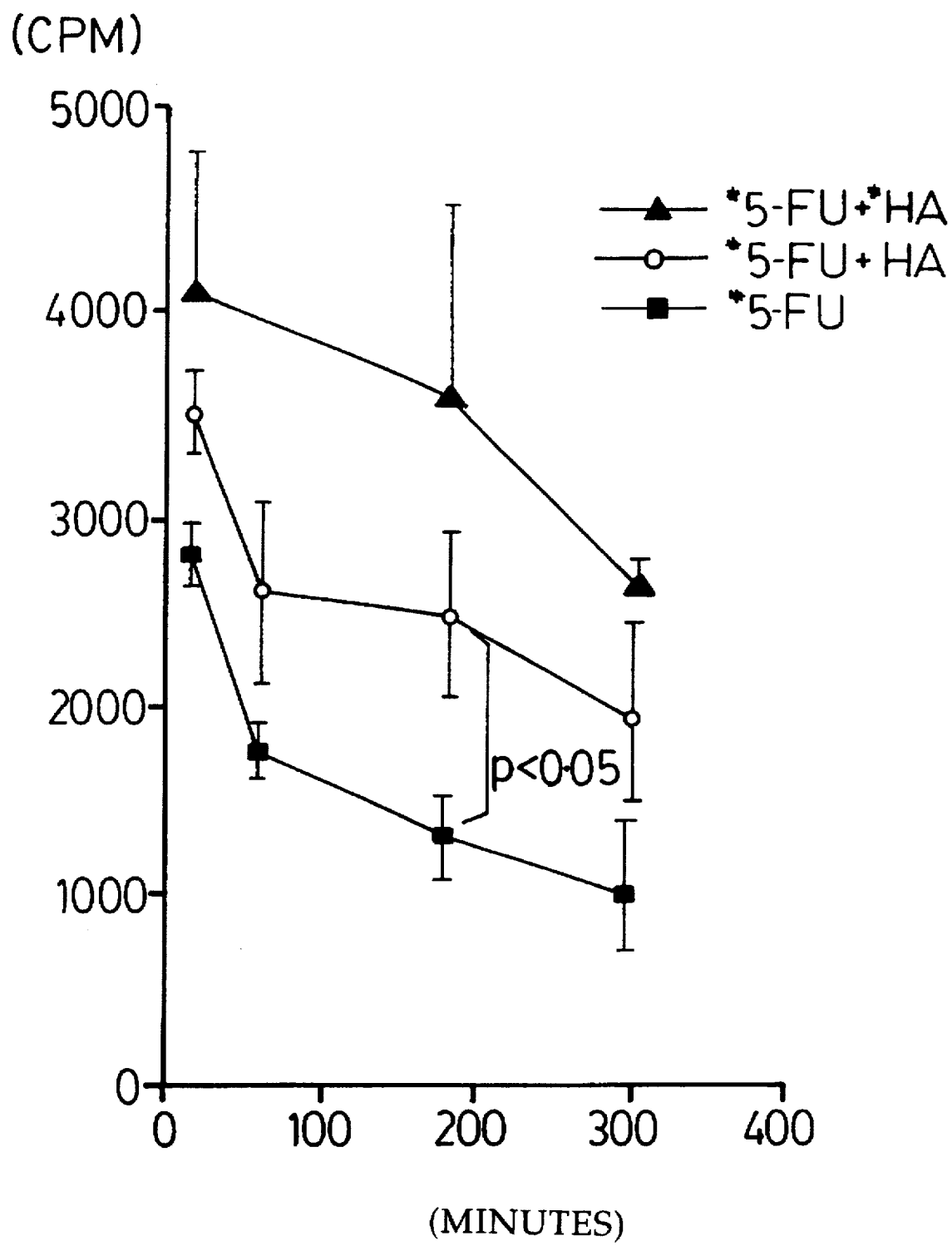
FIG. 12 shows the radioactivity in tumour tissue.

Photographs were taken of patients with basal cell carcinoma FIGS. 4–9 photographs, and of mice with tumors induced in the skin of the hind legs (FIG. 10 photographs). The patients were treated by using combinations of NSAIDS, (non-steroidal anti-inflammatory drugs) and hyaluronic acid (including sodium hyaluronate) according to the invention (3% diclofenac in 2.5% sodium hyaluronate gel base). Each of the six sets of Figures made up of photographs of the different persons include a legend describing or explaining each picture appropriately labelled. The mice had tumours induced in the skin of their hind legs and dosage amounts (2 ml) of Novatrone (10 mg. per dosage amount) (MITOXANTRONE (™) and 2.5% sodium hyaluronate were applied (rubbed onto) the skin at the site of the pathology. The tumours reduced in size clearly illustrating the percutaneous delivery of the medicine by the hyaluronic acid. (See FIG. 10).

The following additional comments are made with respect to the patients.

With respect to R.W. and FIG. 8, the reader will note in FIGS. 8a and 8c the patient suffered from basal cell carcinoma on his back (FIG. 8c) and his temple (FIG. 8a). Because of the age of the individual (86) the basal cell carcinoma on his back could not be reached by him for application of the medication. Thus the basal cell carcinoma in 8c remained untreated and grew (see FIG. 8d). However, the portion indicated in 8a on his temple could be reached and after application of the basal cell carcinoma formulation to the temple and forehead the results are as in 8b; the basal cell carcinoma is disappearing. Thus, the gentlemen's own method of treatment acted as a control.

Figure 7A:
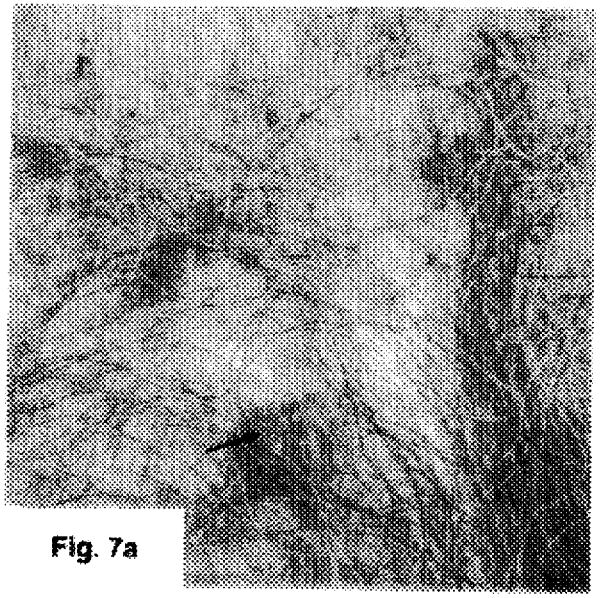
FIGS. 7a–7d show the response of basal cell carcinoma in a 64 year old male patient to treatment with NSAIDs and HA gel.
Figure 7B:
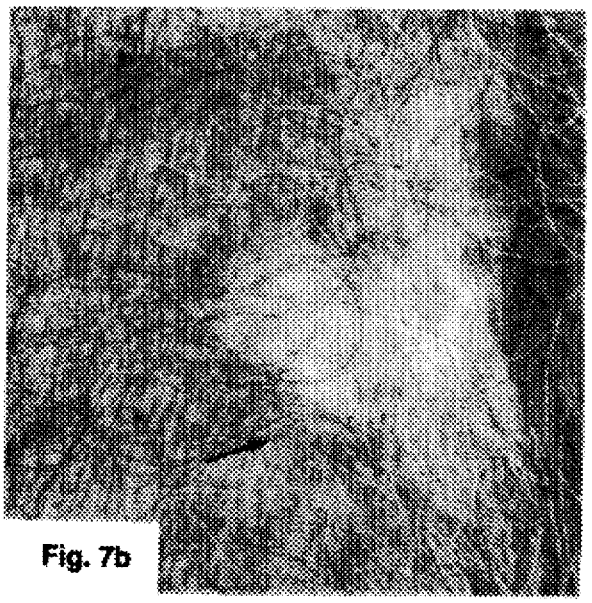
Figure 7C:
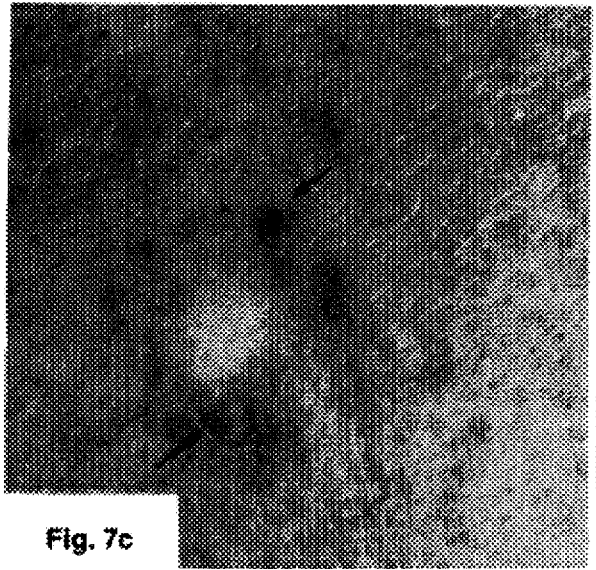
Figure 7D:
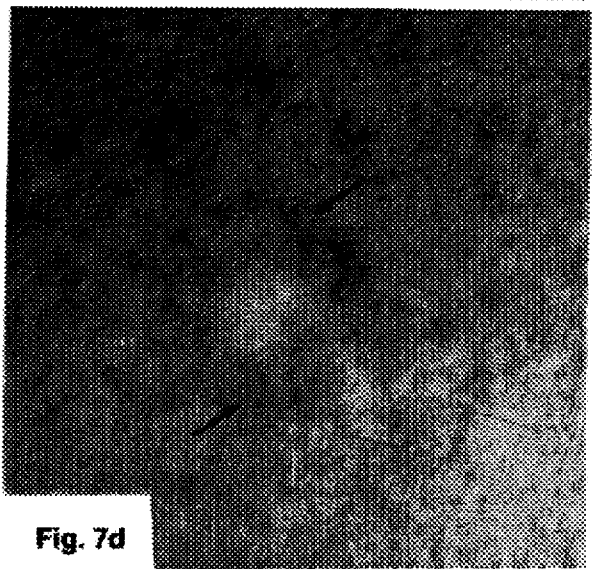

With respect to R.F. and FIGS. 7, two areas of basal cell carcinoma in need of treatment are shown by the arrows in FIGS. 7a and 7c and the results are shown in FIGS. 7b and 7d as indicated by the arrows after treatment with Applicant's invention.

With respect to H.A., male, and FIGS. 6, FIG. 6a indicates two areas of basal cell carcinoma close-ups of which are shown in FIG. 6c. After treatment with the NSAIDS and HA gel three times a day for the period between Jan. 26, 1992 and Mar. 16, 1992 the basal cell carcinoma is clearing as per FIGS. 6b and 6d.

Figure 5A:
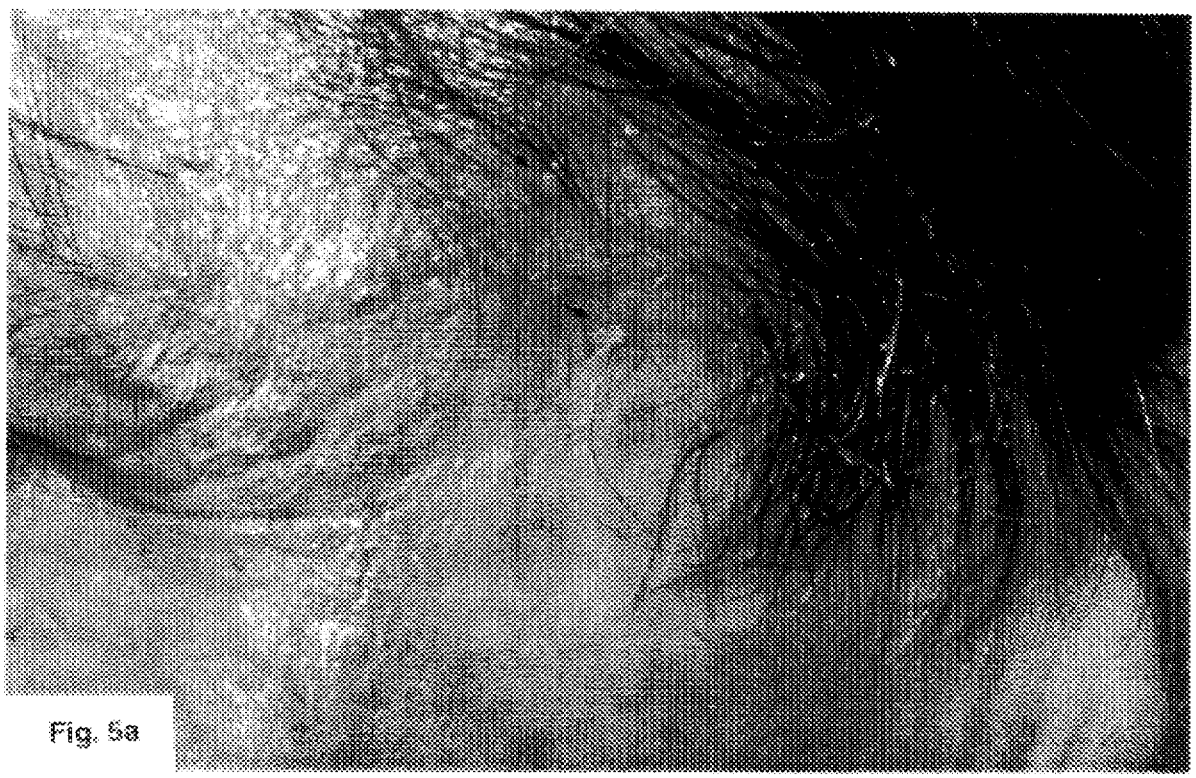
FIGS. 5a and 5b show the response of basal cell carcinoma in a 45 year old male patient to treatment with NSAIDs and HA gel.
Figure 5B:
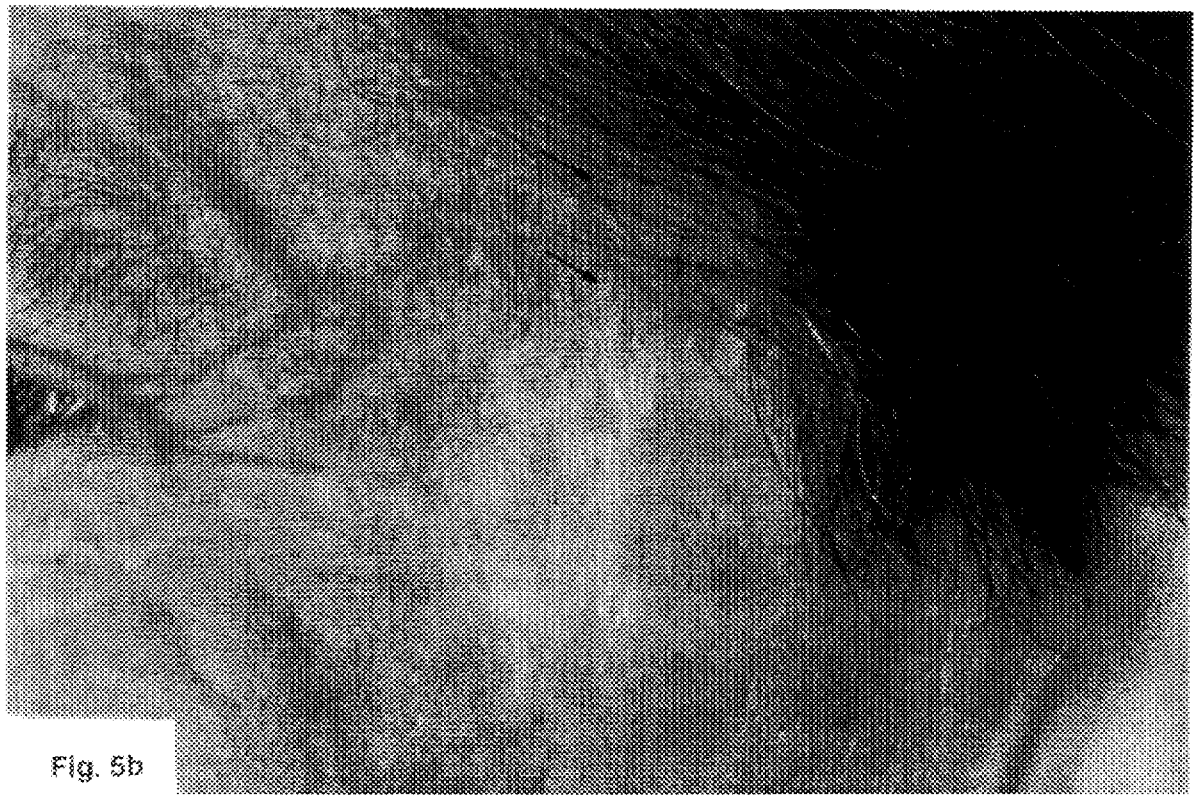

The same is true with respect to male M.F. and FIGS. 5 which appears clear in the photographs (see FIG. 5a and the response shown in FIG. 5b).

Figure 4A:
FIGS. 4a and 4b show the response of basal cell carcinoma in an 82 year old male patient to treatment with NSAIDs and HA gel.
Figure 4B:

With respect to male, W.D. and FIGS. 4, the upper lesion in FIG. 4a (indicated by the upper arrow) is gone after treatment with Applicant's invention (See FIG. 4b) and the two lower lesions in FIG. 4a are well on their way to disappearing (See FIG. 4b).

With respect to female D and FIG. 9, the lesion was left untreated for a long period and gradually encompassed her eye. Surgery could not be undertaken without jeopardizing the eye. By applying Applicant's invention (dosage amounts) over a prolonged period, the basal cell carcinoma has constantly decreased in size.

With respect to FIG. 10, (10a) shows mice having tumors in the skin induced in their hind legs. After continuous applications to the shaved hind legs having the tumors in the skin by rubbing in dosage amounts by Applicant's invention, the tumors have decreased in size.

The effect of Hyaluronic acid as a drug carrier of anticancer agent (5-FU) 5-Fluoracil was also studied.

(Intratumour injection study)

B. EXPERIMENTAL MODEL (2)
 1. Method and Material
  a. Animal: Fisher 344 rat, male 200–250 g
  b. Tumor model Fisher Bladder Carcinoma Tumor (2 mm viable tumor fragment) was transplanted subcutaneously on the right frank by trocar
  c. Treatment was started when tumor size is about 1.5 cm. (2 weeks after implantation.)
 1. These drugs were administrated by intratumor injection. (right frank)

At the same time, injection into normal skin (left frank) was carried out similarly.

Group A: H-5-FU 5 mg/kg+saline /0.3 ml (i.t.)
Group B: H-5-FU 5 mg/kg+HA 15 mg/kg /0.3 ml (s.c.)

3H-FU without or with HA was injected as a single dose (0.3 ml) into the center of the tumor (on the right frank) with a 30 gause needle. At the same time, injection into normal skin (on the left frank) was carried out similarly.

The tumor and skin was then removed at different times (1h, 6hr) for counting radioactivity of the remaining content in the tissue.

2. Result

All the results were expressed as Mean+S.E.

Conclusion

1. In 5-FU_HA group radioactivity was accumulated and retained in the tumor tissue for a long period, whereas rapid clearance was demonstrated in normal tissue. (skin)

2. In 5-FU group, radioactivity immediately disappeared from the tumor or the normal tissue by diffusion, primarily into blood capillaries.

---- 5FU can traverse freely between the interstitial space and blood capillary.

The Effect of Hyaluronic Acid as a Drug Carrier in Target Cancer Chemotherapy

A. EXPERIMENTAL MODEL (1) Intravenous Injection)

1. Method and Material
   a. Animal: Fisher 344 rat, male
      200–250 g
   b. Tumor model
      Fisher Bladder Carcinoma Tumor (2 mm viable tumor fragment) was transplanted subcutaneously on the right frank by trocar
   c. Treatment was started when tumor size is about 1.5 cm. (2 weeks after implantation.) ... tumor weight:1.0±0.3 g The drug was administered Intravenously (through the penile vein)
      Group A: 5-FU 20 mg/kg (3H-5-FU30µCi)+saline
      Group B: 5-FU 20 mg/kg (3H-5-FU30µCi)+HA 15 mg/kg
      Group C: 5-FU 20 mg/kg (3H-5-FU30µCi)+HA 15 mg/kg+(3H-HA30µCi)

2. Sample Collection
   a. accumulation of ADR, 5-FU in tumor tissue and liver
   (1). Tumor was surgically removed (and blood was collected) at *predeterminated time after drug administration. Tumor weight was measured (and blood was centrifuged to obtain a plasma sample.)
      * 15 min, 60 min, 3 hr, 4 hrs, ... after drug administration. Liver was removed for radioactivity counting at the same time.
   (2). Radioactivity level in tumor tissue was counted, using a liquid scintillation counter.

3. Conclusion

Radioactivity in Tumor Tissue and Liver

|        |                    |         | Tumor      | Liver        |
|--------|--------------------|---------|------------|--------------|
| 15 min | 3H – 5FU           | (n = 6) | 2810 ± 165 | 18680 ± 625  |
|        | 3H – 5FU + HA      | (n = 6) | 352 ± 190  | 23593 ± 1460 |
|        | 3H – 5FU + 3H – HA | (n = 4) | 4087 ± 681 | 32060 ± 2145 |
| 60 min | 3H – 5FU           | (n = 3) | 1751 ± 149 | 5451 ± 841   |
|        | 3H – 5FU + HA      | (n = 4) | 2599 ± 489 | 8265 ± 1849  |
| 3 hrs  | 3H – 5FU           | (n = 6) | 1493 ± 227 | 2230 ± 449   |
|        | 3H – 5FU + HA      | (n = 6) | 2512 ± 449 | 2897 ± 340   |
|        | 3H – 5FU + 3H – HA | (n = 4) | 3606 ± 929 | 6977 ± 1633  |
| 5 hrs  | 3H – FU            | (n = 3) | 853 ± 129  | 1129 ± 70    |
|        | 3H – 5FU + HA      | (n = 3) | 1981 ± 479 | 1754 ± 248   |
|        | 3H – 5FU + 3H – HA | (n = 3) | 2168 ± 163 | 3018 ± 325   | mean ± S.E.
HA: 15 mg/kg (30 µCi/kg)
5-FU: 20 mg/kg (30 µCi/kg)

1. Radioactivity in tumor tissue in 5-FU + HA group is higher than that in 5-FU group. There is significant difference (p > 0.05, ANOVA) between with and without HA at 3 hrs after injection. The high intratumor concentration was retained for a prolonged time in 5-FU + HA group. (This retention was confirmed by the intratumor injection study.)

2. These results teach that HA can enhance 5-FU uptake in tumor tissue. This phenomenon results from HA distribution (in tumor tissue HA may be lost from the extracellular matrix) and the vascular uniqueness of tumor tissue (hyperpermiability of tumor vessels to macromolecular drug, HA).

As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A topically administrable pharmaceutical composition comprising a therapeutically effective amount of a drug which inhibits prostaglandin synthesis, and an amount of a form of hyaluronic acid sufficient to transport the composition through the skin into the epidermis or dermis where the composition remains until discharged via the lymphatic system, wherein (a) the drug is 1–5% by weight of the composition, and (b) the form of hyaluronic acid is 1–3% by weight of the composition, has a molecular weight greater than about 150,000 daltons and less than 750,000 daltons, and is selected from the group consisting of hyaluronic acid and salts thereof.

2. The composition of claim 1, wherein the drug is 3% by weight of the composition, and the form of hyaluronic acid is about 2.5% by weight of the composition.

3. The composition of claim 1 or 2 which further comprises a solubilizer for the drug.

4. The composition of claim 1 wherein the drug is a non-steroidal anti-inflammatory drug (NSAID).

5. The composition of claim 1 wherein the drug is an anti-cancer drug.

6. The composition of claim 1 wherein the drug is novantrone.

7. The composition of claim 4 wherein the NSAID is selected from the group consisting of diclofenac, diclofenac sodium, indomethacin, naproxen, (±) tromethamine salt of ketrolac, ibuprofen, piroxicam, propionic acid derivatives, acetylsalicylic acid, and flunixin.

8. The composition of claim 4 which further comprises a pharmaceutical excipient suitable for topical administration, wherein the NSAID is about 3% by weight of the composition, and the form of hyaluronic acid is about 2.5% by weight of the composition.

9. The composition of claim 8 wherein the NSAID is diclofenac sodium.

10. The composition of claim 9 wherein the excipient comprises a solubilizer for the drug.

11. The composition of claim 1 wherein the form of hyaluronic acid has a molecular weight greater than about 600,000 daltons and less than 750,000 daltons.

12. The composition of claim 1 in the form of a gel.

13. The composition of claim 1 in the form of a cream.

14. The composition of claim 1 in the form of a lotion.

15. The composition of claim 1 wherein the form of hyaluronic acid is sodium hyaluronate.

16. The composition of claim 7 wherein the NSAID is diclofenac sodium.

* * * * * the (12) EX PARTE REEXAMINATION CERTIFICATE (8840th)

United States Patent
Falk et al.

(10) Number: US 5,792,753 C1
(45) Certificate Issued: Feb. 7, 2012

(54) COMPOSITIONS COMPRISING HYALURONIC ACID AND PROSTAGLANDIN-SYNTHESIS-INHIBITING DRUGS

(75) Inventors: Rudolf Edgar Falk, Toronto (CA); Samuel Simon Asculai, Toronto (CA)

(73) Assignee: Jagotec AG, Muttenz (CH)

Reexamination Request:
No. 90/011,315, Dec. 6, 2010

Reexamination Certificate for:
Patent No.: 5,792,753
Issued: Aug. 11, 1998
Appl. No.: 08/018,508
Filed: Feb. 17, 1993

Related U.S. Application Data

(63) Continuation-in-part of application No. 07/675,908, filed on Jul. 3, 1991, now Pat. No. 6,069,135, and a continuation-in-part of application No. 07/838,675, filed on Feb. 21, 1992, now Pat. No. 5,639,738, which is a continuation-in-part of application No. 07/675,908, filed on Jul. 3, 1991.

(51) Int. Cl.
| | |
|---|---|
| A61K 9/00 | (2006.01) |
| A61K 31/19 | (2006.01) |
| A61K 31/192 | (2006.01) |
| A61K 31/196 | (2006.01) |
| A61K 31/185 | (2006.01) |
| A61K 31/44 | (2006.01) |
| A61K 31/455 | (2006.01) |
| A61K 31/403 | (2006.01) |
| A61K 31/405 | (2006.01) |
| A61K 31/407 | (2006.01) |
| A61K 31/5415 | (2006.01) |
| A61K 31/715 | (2006.01) |
| A61K 31/728 | (2006.01) |
| A61K 45/06 | (2006.01) |
| A61K 47/00 | (2006.01) |
| A61K 47/36 | (2006.01) |
| A61K 45/00 | (2006.01) |
| A61K 31/726 | (2006.01) |

(52) U.S. Cl. ............... 514/54; 514/23; 514/62; 536/53; 536/55.2; 536/88; 536/123.1

(58) Field of Classification Search ............... None
See application file for complete search history.

(56) References Cited

To view the complete listing of prior art documents cited during the proceeding for Reexamination Control Number 90/011,315, please refer to the USPTO's public Patent Application Information Retrieval (PAIR) system under the Display References tab.

*Primary Examiner* — Dwayne Jones

(57) ABSTRACT

A topically administrable pharmaceutical composition is disclosed which comprises a therapeutically effective amount of a drug which inhibits prostaglandin systhesis, and an amount of a form of hyaluronic acid sufficient to transport the composition through the skin into the epidermis or dermis where the composition remains until discharged via the lymphatic system, wherein (a) the drug is 1-5% by weight of the composition, and (b) the form of hyaluronic acid is 1-3% by weight of the composition, has a molecular weight greater than about 150,000 daltons and less than 750,000 daltons, and is selected from the group consisting of hyaluronic acid and salts thereof.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-5 and 7-16 is confirmed.

New claims 17-36 are added and determined to be patentable.

Claim 6 was not reexamined.

*17. The composition of claim 1, wherein the drug is 3% by weight of the composition.*

*18. The composition of claim 17, wherein the drug is a non-steroidal anti-inflammatory drug (NSAID).*

*19. The composition of claim 18, wherein the NSAID is diclofenac sodium.*

*20. The composition of claim 19, further comprising a preservative.*

*21. The composition of claim 20, wherein the preservative is benzyl alcohol.*

*22. The composition of claim 19, further comprising a solubilizer.*

*23. The composition of claim 22, wherein the solubilizer is benzyl alcohol.*

*24. The composition of claim 12, wherein the drug is 3% by weight of the composition.*

*25. The composition of claim 24, wherein the drug is diclofenac sodium.*

*26. The composition of claim 25, further comprising a preservative.*

*27. The composition of claim 26, wherein the preservative is benzyl alcohol.*

*28. The composition of claim 20, further comprising a solubilizer, wherein the solubilizer is methoxypolyethylene glycol 350.*

*29. The composition of claim 27, further comprising a solubilizer, wherein the solubilizer is methoxypolyethylene glycol 350.*

*30. The composition of claim 29, wherein the benzyl alcohol is 1% by weight of the composition, and the methoxypolyethylene glycol 350 is 20% by weight of the composition.*

*31. The composition of claim 21, wherein the benzyl alcohol is 1% by weight of the composition.*

*32. The composition of claim 27, wherein the benzyl alcohol is 1% by weight of the composition.*

*33. The composition of claim 26, further comprising a solubilizer.*

*34. The composition of claim 33, wherein the preservative is benzyl alcohol and the solubilizer is methoxypolyethylene glycol 350.*

*35. The composition of claim 34, further comprising water.*

*36. The composition of claim 35, wherein the water is less than about 75% by weight of the composition.*

* * * * *

(12) EX PARTE REEXAMINATION CERTIFICATE (9560th)
United States Patent
Falk et al.

(10) Number: US 5,792,753 C2
(45) Certificate Issued: Mar. 13, 2013

(54) COMPOSITIONS COMPRISING HYALURONIC ACID AND PROSTAGLANDIN-SYNTHESIS-INHIBITING DRUGS

(75) Inventors: Rudolf Edgar Falk, Toronto (CA); Samuel Simon Asculai, Toronto (CA)

(73) Assignee: Jagotec AG, Muttenz (CH)

Reexamination Request:
No. 90/012,073, Dec. 28, 2011

Reexamination Certificate for:
Patent No.: 5,792,753
Issued: Aug. 11, 1998
Appl. No.: 08/018,508
Filed: Feb. 17, 1993

Reexamination Certificate C1 5,792,753 issued Feb. 7, 2012

Related U.S. Application Data

(63) Continuation-in-part of application No. 07/675,908, filed on Jul. 3, 1991, and a continuation-in-part of application No. 07/838,675, filed on Feb. 21, 1992, now Pat. No. 5,639,738, which is a continuation of application No. 07/675,908, filed on Jul. 3, 1991, now Pat. No. 6,069,135.

(51) Int. Cl.
| | |
|---|---|
| A61K 9/00 | (2006.01) |
| A61K 31/19 | (2006.01) |
| A61K 31/44 | (2006.01) |
| A61K 31/185 | (2006.01) |
| A61K 31/192 | (2006.01) |
| A61K 31/196 | (2006.01) |
| A61K 31/403 | (2006.01) |
| A61K 31/405 | (2006.01) |
| A61K 31/407 | (2006.01) |
| A61K 31/455 | (2006.01) |
| A61K 31/715 | (2006.01) |
| A61K 31/726 | (2006.01) |
| A61K 31/728 | (2006.01) |
| A61K 31/5415 | (2006.01) |
| A61K 45/00 | (2006.01) |
| A61K 45/06 | (2006.01) |
| A61K 47/36 | (2006.01) |
| A61K 47/0047 | (2006.01) |

(52) U.S. Cl. ............. 514/54; 514/23; 514/53; 514/55.2; 514/62; 514/88; 514/123.1

(58) Field of Classification Search ........................ None
See application file for complete search history.

(56) References Cited

To view the complete listing of prior art documents cited during the proceeding for Reexamination Control Number 90/012,073, please refer to the USPTO's public Patent Application Information Retrieval (PAIR) system under the Display References tab.

*Primary Examiner* — Gary Kunz

(57) ABSTRACT

A topically administrable pharmaceutical composition is disclosed which comprises a therapeutically effective amount of a drug which inhibits prostaglandin systhesis, and an amount of a form of hyaluronic acid sufficient to transport the composition through the skin into the epidermis or dermis where the composition remains until discharged via the lymphatic system, wherein
  (a) the drug is 1-5% by weight of the composition, and
  (b) the form of hyaluronic acid is 1-3% by weight of the composition, has a molecular weight greater than about 150,000 daltons and less than 750,000 daltons, and is selected from the group consisting of hyaluronic acid and salts thereof.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 and 7-16 is confirmed.

Claims 5, 6 and 17-36 were not reexamined.

\* \* \* \* \*